(12) United States Patent
McGrath et al.

(10) Patent No.: US 8,741,592 B2
(45) Date of Patent: *Jun. 3, 2014

(54) METHODS OF SCREENING AN AGENT FOR AN ACTIVITY IN AN ISOLATED EYE OF A TELEOST

(71) Applicant: Phylonix Pharmaceuticals, Inc., Cambridge, MA (US)

(72) Inventors: Patricia McGrath, Cambridge, MA (US); Wen Lin Seng, Westborough, MA (US)

(73) Assignee: Phylonix Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/734,271

(22) Filed: Jan. 4, 2013

(65) Prior Publication Data

US 2013/0281320 A1 Oct. 24, 2013

Related U.S. Application Data

(63) Continuation of application No. 13/037,104, filed on Feb. 28, 2011, now Pat. No. 8,367,364, which is a continuation of application No. 12/137,509, filed on Jun. 11, 2008, now Pat. No. 7,897,363.

(60) Provisional application No. 60/934,455, filed on Jun. 12, 2007.

(51) Int. Cl.
*C12Q 1/34* (2006.01)

(52) U.S. Cl.
USPC .......................................................... 435/18

(58) Field of Classification Search
USPC ............................ 435/18; 424/9.2; 800/3, 20
See application file for complete search history.

(56) References Cited

U.S. PATENT DOCUMENTS

| | | | |
|---|---|---|---|
| 6,299,858 B1 * | 10/2001 | Serbedzija et al. | 424/9.2 |
| 6,656,449 B1 | 12/2003 | Serbedzija et al. | |
| 7,176,189 B2 | 2/2007 | Baranowitz | |
| 7,482,507 B2 * | 1/2009 | Serbedzija et al. | 800/13 |
| 7,897,363 B2 * | 3/2011 | McGrath et al. | 435/18 |
| 8,367,364 B2 * | 2/2013 | McGrath et al. | 435/18 |
| 2002/0187921 A1 | 12/2002 | Rubeinstein | |
| 2005/0079577 A1 | 4/2005 | Ashkenazi et al. | |
| 2006/0123487 A1 | 6/2006 | Serbedzija et al. | |

FOREIGN PATENT DOCUMENTS

WO WO 2008/154641 A1 12/2008

OTHER PUBLICATIONS

International Search Report and Written Opinion, PCT/US2008/066760, "Methods of Screening an Agent for an Activity in an Isolated Eye of a Teleost," dated Aug. 20, 2008.
Response to Rule 312 Communication, U.S. Appl. No. 12/137,509, dated Jan. 6, 2011.
Notice of Allowance, U.S. Appl. No. 12/137,509, dated Oct. 28, 2010.
Office Action, U.S. Appl. No. 12/137,509, dated Apr. 2, 2010.
International Preliminary Report on Patentability and Written Opinion, PCT/US2008/066760, "Methods of Screening an Agent for an Activity in an Isolated Eye of a Teleost," dated Dec. 30, 2009.
Supplementary European Search Report, EP 08 77 0876, "Methods of Screening an Agent for an Activity in an Isolated Eye of a Teleost," dated Oct. 25, 2010.
Hashiguchi, M., et al., "Nodal/Bozozok-independent induction of the dorsal organizer by zebrafish cell lines," *Developmental Biology*, 321(2): 387-396 (Jul. 4, 2008).
Riley, B., et al., "Characterization of harpy/Rcal/cmil mutants: patterning in the absence of cell division," *Developmental Dynamics: An Official Publication of the American Association of Anatomists*, 239(3): 828-843 (Feb. 3, 2010).
Nadauld, L.D., et al., "Dual roles for adenomatous polyposis coli in regulating retinoic acid biosynthesis and Wnt during ocular development," *Proceedings of the National Academy of Sciences of the United States of America*, 103(36): 13409-13414 (Sep. 5, 2006).
Office Action, U.S. Appl. No. 13/037,104, dated Feb. 14, 2012.
Notice of Allowance & Fees Due, U.S. Appl. No. 13/037,104, dated Feb. 14, 2012.

* cited by examiner

*Primary Examiner* — Ralph Gitomer
(74) *Attorney, Agent, or Firm* — Hamilton, Brook, Smith & Reynolds, P.C.

(57) ABSTRACT

The present invention provides methods of screening an agent for an activity in an isolated organ, e.g., eye, from a teleost, e.g., zebrafish. Methods of isolating eyes from zebrafish are provided. Methods of screening an agent for an ocular activity in the isolated eye are provided. Methods of screening an agent for an ocular activity in a model of ocular disease or disorder are provided. Methods of screening an agent for an ocular activity in the isolated eye and for screening the agent for cell death and/or toxic activity in the eye or other organ or tissue are provided. The invention further provides high throughput methods of screening agents for an activity in isolated eyes of zebrafish in multi-well plates.

27 Claims, 9 Drawing Sheets

SEQUENCE LISTING

<160> NUMBER OF SEQ ID NOS: 10

<210> SEQ ID NO 1
<211> LENGTH: 21

```
<212> TYPE: DNA
<213> ORGANISM: Artifical Sequence
<220> FEATURE:
<223> OTHER INFORMATION: Synthetic zebrafish specific primer - HIF left

<400> SEQUENCE: 1
gacgtggaag gttcttcact g                                              21

<210> SEQ ID NO 2
<211> LENGTH: 21
<212> TYPE: DNA
<213> ORGANISM: Artificial Sequence
<220> FEATURE:
<223> OTHER INFORMATION: Synethic zebrafish specific primer - HIF right

<400> SEQUENCE: 2
tcaagaggtc atctggctca t                                              21

<210> SEQ ID NO 3
<211> LENGTH: 20
<212> TYPE: DNA
<213> ORGANISM: Artificial Sequence
<220> FEATURE:
<223> OTHER INFORMATION: Synethic zebrafish specific primer - FGEF left

<400> SEQUENCE: 3
gtaaaggctg cccacatacc                                                20

<210> SEQ ID NO 4
<211> LENGTH: 20
<212> TYPE: DNA
<213> ORGANISM: Artifical Sequence
<220> FEATURE:
<223> OTHER INFORMATION: Synthetic zebrafish specific primer - VGEF
      right

<400> SEQUENCE: 4
gctttgactt ctgcctttgg                                                20

<210> SEQ ID NO 5
<211> LENGTH: 20
<212> TYPE: DNA
<213> ORGANISM: Artificial Sequence
<220> FEATURE:
<223> OTHER INFORMATION: Synethic zebrafish specific primer - IGF left

<400> SEQUENCE: 5
agtgatgccc gcattaaaac                                                20

<210> SEQ ID NO 6
<211> LENGTH: 20
<212> TYPE: DNA
<213> ORGANISM: Artifical Sequence
<220> FEATURE:
<223> OTHER INFORMATION: Synthetic zebrafish specific primer - IGF right

<400> SEQUENCE: 6
tctgtgcaaa cgatcctgtc                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic zebrafish specific primer - PEDF left

<400> SEQUENCE: 7
```

```
-continued agctatcaat gggagcgtct                                              20

<210> SEQ ID NO 8
<211> LENGTH: 20
<212> TYPE: DNA
<213> ORGANISM: Artificial Sequence
<220> FEATURE:
<223> OTHER INFORMATION: Synethic zebrafish specific primer - PEDF right

<400> SEQUENCE: 8
ctccaccagc aagaatctga                                              20

<210> SEQ ID NO 9
<211> LENGTH: 20
<212> TYPE: DNA
<213> ORGANISM: Artificial Sequence
<220> FEATURE:
<223> OTHER INFORMATION: Synethic zebrafish specific primer - PGK left

<400> SEQUENCE: 9
gcctctgtgg tttctcaagg                                              20

<210> SEQ ID NO 10
<211> LENGTH: 20
<212> TYPE: DNA
<213> ORGANISM: Artificial Sequence
<220> FEATURE:
<223> OTHER INFORMATION: Synethic zebrafish specific primer - PGK right

<400> SEQUENCE: 10
aggcctctgt ggtttctcaa                                              20
```

METHODS OF SCREENING AN AGENT FOR AN ACTIVITY IN AN ISOLATED EYE OF A TELEOST

RELATED APPLICATIONS

This application is a continuation of U.S. application Ser. No. 13/037,104, filed Feb. 28, 2011 now U.S. Pat. No. 8,367,364, which is a continuation of U.S. application Ser. No. 12/137,509, filed Jun. 11, 2008, now U.S. Pat. No. 7,897,363, which claims the benefit of U.S. Provisional Application No. 60/934,455, filed Jun. 12, 2007. The entire teachings of the above applications are incorporated herein by reference.

GOVERNMENT SUPPORT

This invention was supported by grants from the National Institutes of Health (Grant Nos. 1R43EY016254-01, and 1R44EY015335-02). The U.S. Government may have certain rights in this invention.

INCORPORATION BY REFERENCE OF MATERIAL IN ASCII TEXT FILE

This application incorporates by reference the Sequence Listing contained in the following ASCII text file being submitted concurrently herewith:

a) File name: 32621003006SEQLIST.txt; created Jan. 3, 2013, 2.40 KB in size.

BACKGROUND OF THE INVENTION

The identification of therapeutic or prophylactic compounds that may be useful for treating or preventing ocular diseases and disorders while exhibiting low toxicity and/or side effects is a focal point of drug discovery and development. Evaluation of the potential impact of drug candidates on human and animal health is a major component of the risk/benefit assessment. A number of cell-based in vitro efficacy and toxicity screens have been developed; these screens, however, do not permit evaluation of the therapeutic and toxic effects of a compound in vivo on an intact animal. Notably, cell-based-assays are designed at the molecular and cellular levels. As a result, determining the impact of a compound of interest on higher levels of cellular organization, such as on an intact eye, or during eye (ocular) development, requires whole animal testing. In addition, current screens do not permit the assessment of compound effects on other potential target cells, tissues and organs of an animal together with those effects on the eye, simultaneously or over time. Thus, there is a need for cost-effective, comprehensive methods for screening compounds for in vivo ocular activity.

Zebrafish are used as a small animal model in which to screen compounds for biological activity such as, for example, angiogenesis activity, cell death activity, and/or toxic activity. (See, e.g., U.S. Pat. Nos. 6,299,858 and 6,656,449, the disclosures of which are incorporated herein in their entirety for all purposes.) Compared with conventional animal models, zebrafish provide several advantages, including, for example, short assay times, easy animal maintenance, need for smaller quantities of compounds, single dosing of compounds, ease of administration of compounds, quantitative assays, ease of obtaining a statistically significant number of animals per test, and suitability for large-scale screening of compounds (See, e.g., Norrby, *J. Cell. Mol. Med.* 10:588-612, 2006; U.S. Pat. Nos. 6,299,858 and 6,656,449). The present invention relates to the use of zebrafish and other teleosts to screen agents for ocular activity, as well as for cell death and/or toxic activity in target tissues and/or organs from a whole, live animal in vivo.

BRIEF SUMMARY OF THE INVENTION

The invention provides a method of analyzing an eye from a teleost. The method comprises: contacting the teleost with an enzyme capable of dissociating the eye from the teleost; and analyzing the dissociated eye. Optionally, the method further comprises contacting the teleost with an agent, and analyzing a response to the agent in the dissociated eye. Optionally, the method further comprises collecting the dissociated eye by filtration or density gradient centrifugation. Optionally, the enzyme is a collagenase, a dispase, a trypsin, a chymotrypsin, or a hyaluronidase. Optionally, the teleost is in a well of a multi-well plate. Optionally, the method further comprises removing the teleost body from the well before the analyzing step. Optionally, the agent is an inducer or potential inducer of ocular disease. Optionally, the response indicates whether the inducer or potential inducer induces the disease. Optionally, the teleost has or is susceptible to an ocular disease and the agent is an inhibitor or potential inhibitor of ocular disease. Optionally, the first and second agents are administered, the first agent being an inducer of ocular disease and the second agent being an inhibitor or potential inhibitor of the disease, and the analyzed response provides an indication whether the second agent inhibits the disease, wherein the first and second agents can be administered in either order or together. Optionally, the response is analyzed using a microplate reader, a high content imaging system, or a microscope. Optionally, the isolated eye is contained on a slide following isolation of the eye from the teleost. Optionally, the analyzing step comprises detecting a target biomolecule. Optionally, the target biomolecule is a protein or mRNA. Optionally, the analyzing step is performed on the isolated eye in situ. Optionally, the response to the agent comprises an increase or decrease in angiogenesis. Optionally, the response to the agent comprises an increase or decrease in blood vessel formation. Optionally, the blood vessels are visualized by staining of the eye with a vessel-specific antibody. Optionally, the teleost is an embryo, larva, or adult. Optionally, the teleost is a zebrafish, medaka, Giant rerio, or puffer fish. Optionally, the teleost is a wildtype, mutant or transgenic teleost. Optionally, the agent is administered to the teleost by dissolving the agent in media used for culturing the teleost. Optionally, the agent is administered to the teleost by injecting the agent into the teleost. Optionally, the agent is a small molecule, nucleic acid, nucleic acid analog, peptide, protein, glycoprotein, carbohydrate, lipid, or glycolipid. Optionally, the agent is a member of a library of agents is screened for an ocular activity in the isolated eyes of a plurality of teleosts. Optionally, analyzing the response to the agent comprises assessing the isolated eye for a morphological change. Optionally, the morphological change comprises a change in size, shape, pigmentation, color, or structure of the eye. Optionally, the morphological change comprises a change in blood vessel structure. Optionally, assessing the morphological change comprises acquiring an image of the isolated eye. Optionally, the acquired image is a digital image and assessment of the morphological change comprises computer-based analysis of the digital image. Optionally the agent induces ocular neovascularization in the teleost. Optionally, the agent that induces ocular neovascularization in the teleost is $CoCl_2$ or Penicillamine. Optionally, the method further comprises surgically cutting the conjunctiva and then burning the sclera of the teleost to induce ocular scaring; and wherein the analyzing step comprises determining whether the agent reduce scarring of the sclera relative to a control teleost not treated with the agent; wherein the cutting step and the administering step can be performed in either order or together.

The present invention relates generally to methods of screening an agent for an activity in an eye of a teleost. In some embodiments, the activity is an ocular or ophthalmologic activity. In other variations, the activity is a cell death or toxic activity. The method generally includes contacting the teleost with the agent, isolating an eye from the teleost, and measuring a response to the agent in the isolated eye, the response being an indication that the agent has the activity.

Typically, the eye is isolated by contacting the teleost with an enzyme that is capable of dissociating the eye from the teleost, thereby facilitating separation of the eye from the teleost, and collecting the separated eye. The collecting step can include, for example, filtration or density gradient centrifugation. Particularly suitable enzymes include, e.g., collagenases, such as, for example, bacterial collagenases (e.g., collagenase Type I, collagenase Type II, collagenase Type III, or collagenase Type IV) or mammalian collagenases. In certain variations of the method, the collagenase is incubated with the teleost or the eye of the teleost at a concentration of between about 15 U/ml and about 150 U/ml. Suitable incubation times include times of between about 30 minutes and about 16 hours. In some methods, the collagenase is incubated with the teleost at a temperature of between room temperature. (RT) and about 37° C. In a specific embodiment, bacterial collagenase Type II is incubated with the teleost or the eye of the teleost at a concentration of 150 U/ml for 45 minutes at 37° C. In other variations, an enzyme other than a collagenase is used to dissociate an organ from a teleost. Some such enzymes include, for example, a dispase, a trypsin, a chymotrypsin, and a hyaluronidase.

In some variations, the teleost is a teleost model for an ocular disease or disorder. Some such models include, for example, choroidal neovascularization (CNV) that occurs in an advanced form of age-related macular degeneration (AMD) in human, corneal neovascularization, or ocular scarring that occurs post-surgery for glaucoma. In some embodiments, the method generally comprises contacting the teleost with an agent that induces a phenotype in the teleost that mimics the ocular disease or disorder, contacting the teleost with the agent, isolating an eye from the intact body of the teleost, and detecting the response to the agent in the isolated eye. In other embodiments, the method generally comprises performing microsurgery on the teleost to induce a phenotype in the teleost that mimics the ocular disease, disorder, or post-surgery complication, contacting the teleost with the agent, isolating an eye from the intact body of the teleost, and detecting the response to the agent in the isolated eye.

In certain embodiments, the step of contacting the teleost with the agent to be screened for the activity, is performed while the teleost is contained in a first vessel (e.g., a culture plate or well of a multi-well plate) and the step of measuring the response in the isolated eye is performed while the isolated eye is contained in a second vessel (e.g., a culture plate or well of a multi-well plate). In such embodiments, the teleost eye is typically transferred to the second vessel following its isolation from the teleost body. In some variations in which a plurality of eyes are isolated from a plurality of teleosts, the teleosts are contained in the first vessel and at least some of the isolated eyes are transferred to the second vessel, optionally after dissociating the eyes from the teleosts. In certain alternative variations, at least some of isolated eyes are transferred to a plurality of other vessels. For example, in a specific embodiment, each isolated eye is transferred to a separate vessel for measuring the response on each eye individually; in other specific embodiments multiple isolated eyes are transferred to each of a plurality of vessels.

As indicated above, the teleost and/or isolated eye can be contained in a well of a multi-well plate (e.g., a well of a multi-well tissue culture plate). Suitable wells include, for example, those of a 6-, 24-, or 96-well plate. Particularly suitable, such as, e.g., for high throughput screens and/or with embryonic teleosts, are microtiter wells (e.g., microtiter wells of a 96- or 388-well microtiter plate). In such embodiments, the contacting step can include adding the agent to the well. Further, where the isolated eye is contained within a microtiter well, the response can be detected using a microplate reader.

In some alternative embodiments, the isolated eye is placed on a non-multi-well substrate for measuring the response. In a specific variation, the isolated eye is placed on a slide (e.g., glass), such as, for example, a depression slide. In yet other embodiments, the isolated eye is suspension in a solution for measurement of the response. In these variations; the response can be measured using, for example, a flow cytometer or a large particle dispenser.

In other variations, a plurality of teleosts is contacted with the agent. The plurality of teleosts can be contained within a plurality of wells (e.g., microtiter wells) of one or more multi-well plates. In such embodiments, the contacting step can include adding the agent to each of the wells. At least some of the plurality of wells can contain a different concentration of the agent. In certain embodiments, each of the wells contains a single teleost from among the plurality of teleosts, or each of the wells contains multiple teleosts from among the plurality of teleosts.

In yet other variations, the method includes contacting a plurality of teleosts with a plurality of agents such that at least some of the plurality of teleosts is contacted with a different agent. The plurality of teleosts can be contained within a plurality of wells (e.g., microtiter wells) of one or more multi-well plates. In such embodiments, the contacting step can include adding the agents to the wells so that some of the plurality of wells contains a different agent. In certain embodiments, each of the wells contains a single teleost from among the plurality of teleosts, or each of the wells contains multiple teleosts from among the plurality of teleosts.

In certain embodiments, where a plurality of eyes are isolated from a plurality of teleosts, such plurality of eyes can also be contained in a plurality of wells (e.g., microtiter wells) of one or more multi-well plates. Each of the wells can contain a single eye from among the plurality of eyes, or each of the wells can contain multiple eyes from among the plurality of eyes.

In some embodiments of the method, the activity in the isolated eye is angiogenesis or blood vessel formation. The angiogenesis or blood vessel formation activity can be decreased or can be increased in response to the agent. The blood vessels can be visualized by light microscopy after alkaline phosphatase staining of the teleost. In such variations, the teleost is optionally bleached after staining with alkaline phosphatase. The blood vessels can be also visualized by fluorescence microscopy after immunostaining with a vessel-specific monoclonal antibody. In some such variations, the teleost is incubated with a vessel-specific monoclonal antibody (e.g., Phy-V) conjugated with Alexa 488 or with an unlabelled primary vessel-specific monoclonal antibody (e.g., Phy-V) and a rhodamine-conjugated secondary antibody.

The teleost can be of any developmental stage, including embryo, larva, or adult. Suitable teleosts include zebrafish, medaka, Giant rerio, or puffer fish. Zebrafish embryos or adult zebrafish are particularly suitable. In some methods, the teleost is a wild-type strain. Alternatively, the teleost can contain a mutation in a selected gene, such as, for example, a gene associated with an ocular disorder or disease. In certain embodiments, the teleost is transgenic.

A variety of means can be used to contact a teleost with the agent. In some methods, the agent is administered to the teleost by dissolving the agent in media containing the teleost. The agent can be dissolved in media before or after adding the teleost to the media. In other variations, the agent is administered to the teleost by injecting the agent into the teleost or into the eye to be isolated. In certain embodiments, the agent is administered to the teleost in conjunction with a carrier. The carrier can be, for example, a solvent, a lipid, or a peptide.

A variety of different types of agents can be tested for activity using the present methods. In certain embodiments, the agent can be a small molecule, a nucleic acid, a peptide, a protein, a glycoprotein, a carbohydrate, a lipid, or a glycolipid. In specific variations in which the agent is a nucleic acid, the nucleic acid is a DNA or RNA; in other specific variations, the nucleic acid is an siRNA or a morpholino. In some embodiments, a library of agents is screened for activity in the isolated eye. Suitable libraries include small molecule libraries, nucleic acid libraries, and peptide libraries.

In certain embodiments in which the method is a method of screening an agent for an activity in a teleost model of an ocular disease or disorder, the teleost is contacted with an agent that induces a disease or disorder in the teleost, where the ocular activity being assessed is indicative of the disease or disorder. In some such variations, the response measured in the teleost is indicative of a therapeutic or protective effect against the disease or disorder. Contacting the teleost with the disease-inducing agent can be performed before, at the same time as, or after contacting of the agent with the agent being screened for the ocular activity. In specific embodiments, the teleost is contacted with a compound that induces a phenotype in the teleost that mimics ocular or choroidal neovascularization (CNV), such as that observed in age-related macular degeneration (AMD). In some variations, the compound that induces the CNV phenotype is $CoCl_2$ or Penicillamine. In certain exemplary embodiments, the compound that induces the CNV phenotype is contacted with the teleost at 24 hours post-fertilization (hpf). The teleost can be contacted with the agent to be screened for an activity on CNV before, at the same time as, or after the teleost is contacted compound that induces the CNV phenotype.

In other embodiments in which the method is a method of screening an agent for an activity in a teleost model of an ocular disease or disorder, microsurgery is performed on the teleost to induce a phenotype in the teleost that mimics ocular scarring which occurs post-surgery for glaucoma. These embodiments generally include surgically cutting the conjunctiva and then burning the sclera to induce the ocular scarring phenotype. The teleost can be contacted with the agent to be screened for an activity on ocular scarring before, at the same time as, or after conjunctiva is cut and the sclera is burned.

In certain embodiments, the method of screening an agent for an ocular or ophthalmologic activity in an enzymatically isolated eye from a teleost further includes screening the agent for cell death and/or toxic activity in the eye or ocular tissue of the teleost. Such variations generally include detecting a measure of the cell death and/or toxic activity in the isolated eye of the teleost. Accordingly, the method includes contacting the teleost with the agent; isolating an eye from the teleost; measuring a first response to the agent in the isolated eye, the first response being an indication that the agent has the ocular activity; and measuring a second response to the agent in the isolated eye, the second response being an indication that the agent has the cell death and/or toxic activity.

In yet other embodiments, the method of screening an agent for an ocular or ophthalmologic activity in an eye of a teleost further includes screening the agent for cell death and/or toxic activity in at least one other organ or tissue of the teleost. These variations generally include detecting a measure of the cell death and/or toxic activity in at least one organ or tissue of the teleost other than the eye. Accordingly, the method includes contacting the teleost with the agent; isolating an eye from the teleost; measuring a first response to the agent in the isolated eye, the first response being an indication that the agent has the ocular activity; and measuring a second response to the agent in at least one other organ or tissue of the teleost, the second response being an indication that the agent has the cell death and/or toxic activity. In some methods, the cell death and/or toxic activity is detected before isolating the eye of the teleost.

In other embodiments of the method, measuring the response to the agent comprises assessing the isolated eye for a morphological change (e.g., a morphological defect). The morphological change to be assessed can include, for example, a change in size, shape, pigmentation, color, or structure of the eye. In a specific embodiment, a change in blood vessel structure is assessed. Measuring morphological changes can include, for example, acquiring an image of the isolated by using any of various microscopic methods. In one particular embodiment, a digital image of the isolated eye is acquired and the method includes computer-based analysis of the digital image.

In some variations, ocular activity to be detected is indicative of a disease or disorder in the teleost eye and the screening method is a method of determining whether an agent induces the disease or disorder in the teleost and wherein the ocular activity is indicative of a disease or disorder. In some such variations, a plurality of agents are screened for the ocular activity indicative of the disease or disorder.

In yet other variations, the method is a method of screening an agent for a protective or therapeutic effect against a disease or disorder in an eye of a teleost. Such embodiments typically comprise the method of contacting the teleost with a first agent that induces the disease or disorder in the teleost; contacting the teleost with a second agent; isolating an eye from the teleost; and measuring a response to the agent in the isolated eye, wherein the response is indicative of whether the second agent has a protective or therapeutic effect against the disease or disorder. Contacting the teleost with the disease-inducing agent can be performed before, at the same time as, or after contacting of the teleost with the second agent to be screened for a therapeutic or protective effect. In a particular variation of the method, a plurality of agents are screened for the protective or therapeutic effect against the disease or disorder.

In still other embodiments, the method of screening is compatible with automated screening devices (e.g., high throughput screening using multi-well plates). In certain variations, the agent is screened in high throughput in multi-well plates for an ocular or ophthalmologic activity in an isolated eye of a teleost, and is optionally for cell death and/or toxic activity in an isolated eye of a teleost or in at least one other organ or tissue of the teleost. Teleosts can be contacted with agents by adding the agents to microtiter wells containing the teleosts. When using a plurality of microtiter wells such as with a microtiter plate, the same agent can be tested for activity using different concentrations of the same agent in different wells, and/or different agents can be tested for activity, such as with each well containing a different agent. Each microtiter well can contain a single teleost or isolated eye or multiple teleosts or isolated eyes.

This invention results, in part, from the insight that enzymatic treatment, such as, e.g., with a collagenase, can be used to dissociate the eyes from an intact body of a teleost without laborious manual dissection and deleterious effect on the isolated eyes. Using enzymatic treatment, the eyes and the body of zebrafish remain generally intact. For example, using enzymatic treatment with a collagenase, the eyes and the body of zebrafish remain intact (see FIG. 1), with only ~10% zebrafish having remnants of eye blood vessels remaining in the eye socket in the detached body.

A further understanding of the nature and advantages of the inventions herein may be realized by reference to the detailed description of the specification and the associated figures.

Definitions

Unless defined otherwise, all technical and scientific terms used herein have the same meaning as commonly understood by those of ordinary skill in the art to which this invention belongs. The following references provide a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991), the following terms and phrases have the meanings ascribed to them unless specified otherwise. Although any methods and materials similar or equivalent to those described herein can be used in the practice or testing of the present invention, the preferred methods and materials are described. For purposes of the present invention, the following terms and phrases are intended to have the following general meanings as they are used herein.

The terms "a," "an," and "the" include plural referents unless the context clearly dictates otherwise.

The term "subject" includes an animal. The term "animal" includes a vertebrate animal, such as a vertebrate fish. Vertebrate fish include teleosts, such as, e.g., zebrafish, medaka, Giant rerio, and puffer fish. The term "teleost" means of or belonging to the Teleostei or Teleostomi, a group consisting of numerous fishes having bony skeletons and rayed fins. Teleosts include, for example, zebrafish, medaka, Giant rerio, and puffer fish.

The term "larva" or "larval" means the stage of any of various animals, including vertebrate animals, such as vertebrate fishes (including teleosts, such as, e.g., zebrafish, medaka, Giant rerio, and puffer fish), between embryogenesis and adult.

"Ocular activity" and "ophthalmologic activity" are synonymous. Ocular activity or ophthalmologic activity in reference to a subject refers to activity associated with visual function within, or originating within, a subject, particularly within an eye or ocular tissue (e.g., lens, retina, cornea, blood vessels) of a subject. Ocular activity of an agent is the ability of the agent to affect (e.g., induce, enhance, inhibit, delay or prevent) an ocular activity in the eye of a subject. For example, the ocular activity of an agent includes the ability of the agent to induce, enhance, inhibit, delay or prevent symptom(s) and/or sign(s) of ocular disease and/or normal physiological process(es) occurring within the eye. The activity of the agent can be manifested in the eye or other ocular tissue (e.g., lens, retina, cornea, blood vessels) in a subject.

The term "symptom" or "clinical symptom" refers to a subjective evidence of a disease, such as decreased vision, as perceived by the patient. A "sign" refers to objective evidence of a disease as observed by a physician.

"Angiogenesis activity" or "angiogenic activity" in reference to an agent is the ability of the agent to induce, enhance, inhibit, delay or prevent the formation or outgrowth of blood vessels or lymph vessels. Angiogenesis activity or angiogenic activity in reference to a subject refers to activity associated with angiogenesis within a subject or organ(s) or tissue(s) of a subject or originating from within a subject or organ(s) or tissues(s) of the subject.

"Anti-angiogenesis activity" or "anti-angiogenic activity" in reference to an agent is the ability of the agent to inhibit, delay, prevent, or greatly reduce the formation or outgrowth of blood or lymph vessels, or destroy such vessels during sprouting or outgrowth. Anti-angiogenesis activity or anti-angiogenic activity in reference to a subject refers to activity associated with anti-angiogenesis within a subject or organ(s) or tissue(s) of a subject or originating from within a subject or organ(s) or tissues(s) of the subject.

An "effect on angiogenesis activity" or "effect on angiogenic activity" refers to the way in which an agent acts upon or influences angiogenesis or angiogenic activity in a subject. Such effects include an ability to induce, enhance, delay or inhibit angiogenesis or angiogenic activity in the subject, as indicated or manifested by, for example, a clinical manifestation, characteristic, symptom, or event that occurs or is observed in, associated with, or peculiar to angiogenesis of tissues or organs in a subject.

An "effect on anti-angiogenesis activity" or "effect on anti-angiogenic activity" refers to the way in which an agent acts upon or influences anti-angiogenesis or anti-angiogenic activity in a subject. Such effects include an ability to induce, enhance, delay or inhibit anti-angiogenesis or anti-angiogenic activity in the subject, as indicated or manifested by, for example, a clinical manifestation, characteristic, symptom, or event that occurs or is observed in, associated with, or peculiar to angiogenesis of tissues or organs in a subject.

"Cell death activity" in reference to an agent is the ability of the agent to induce, enhance, inhibit, delay or prevent the death of one or more cells within a subject or organ(s) or tissue(s) of a subject or originating from within a subject or organ(s) or tissues(s) of the subject. Cell death activity in reference to a subject refers to activity associated with the death of cells within a subject or organ(s) or tissue(s) of a subject or originating from within a subject or organ(s) or tissues(s) of the subject.

"Apoptotic activity" or "apoptosis activity" in reference to an agent is the ability of the agent to induce, enhance, inhibit, delay or prevent apoptosis. Apoptotic activity or apoptosis activity in reference to a subject refers to activity associated with the death of cells within a subject or organ(s) or tissue(s) of a subject or originating from within a subject or organ(s) or tissues(s) of the subject.

The term "necrotic activity" or "necrosis activity" in reference to an agent is the ability of the agent to induce, enhance, inhibit, delay or prevent necrosis. Necrotic activity or necrosis activity in reference to a subject refers to activity associated with the necrosis of cells within a subject or organ(s) or tissue(s) of a subject or originating from within a subject or organ(s) or tissues(s) of the subject.

An "effect on cell death activity" refers to the way in which an agent acts upon or influences cell death activity in a subject. Such effects include an ability to induce, enhance, delay or inhibit cell death activity in the subject, as indicated or manifested by, for example, a clinical manifestation, characteristic, symptom, or event that occurs or is observed in, associated with, or peculiar to death of cells in a subject.

An "effect on apoptotic activity" refers to the way in which an agent acts upon or influences apoptotic activity in a subject. Such effects include an ability to induce, enhance, delay or inhibit apoptotic activity in the subject, as indicated or manifested by, for example, a clinical manifestation, characteristic, symptom, or event that occurs or is observed in, associated with, or peculiar to apoptosis of cells in a subject.

An "effect on necrotic activity" refers to the way in which an agent acts upon or influences necrotic activity in a subject. Such effects include an ability to induce, enhance, delay or inhibit necrotic activity in the subject, as indicated or manifested by, for example, a clinical manifestation, characteristic, symptom, or event that occurs or is observed in, associated with, or peculiar to necrosis of cells in a subject.

The term "gene" is used broadly to refer to any segment of DNA associated with a biological function. Thus, genes include coding sequences and/or the regulatory sequences required for their expression. Genes also include non-expressed DNA segments that, for example, form recognition sequences for other proteins.

The terms "nucleic acid" or "nucleic acid segment" refer to a deoxyribonucleotide or ribonucleotide and polymer thereof which is in either single- or double-stranded form. Unless specifically limited, the term encompasses nucleic acids containing known analogues (synthetic and naturally occurring) of nucleotides, which have similar binding properties as the reference nucleic acid and are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., 1991, *Nucleic Acid Res.* 19:5081; Ohtsuka et al., 1985, *J. Biol. Chem.* 260:2605-2608; Rossolini et al., 1994, *Mol. Cell. Probes* 8:91-98). The term nucleic acid is used interchangeably with gene, cDNA, and mRNA encoded by a gene.

The terms "nucleic acid" or "nucleic acid segment" also refer to oligonucleotides, either single- or double-stranded that are used in the art to down-regulate or "knock-down" expression of a gene. Such nucleic acids or nucleic acid segments include, for example and not for limitation, nucleic acids containing the four bases (A, G, C or U for ribonucleotides and A, G, C or T for deoxyribonucleotides) or analogues or derivatives (synthetic and naturally occurring) thereof, which have similar binding properties as the reference nucleic acid, morpholinos, small inhibitory RNA (siRNA), and the like. Morpholinos, which are chemically modified deoxyribonucleotides that display similar binding properties but are resistant to metabolism compared to standard oligonucleotides by virtue of their morpholino rather than ribose backbone, have been used in zebrafish (see U.S. Pat. No. 6,867,349 and Ekker and Larson, *Genesis* 30:89-93, 2001). siRNA is a double-stranded RNA which induces mRNA degradation after being processed by an RNA-induced silencing complex to an anti-sense RNA and hybridizing to its target gene sequences (see Fire et al., *Nature* 391: 806-811, 1998).

The term "isolated nucleic acid" or "isolated nucleic acid segment" means a single- or double-stranded nucleic acid (e.g., an RNA, DNA, or a mixed polymer), which is substantially separated from other genome DNA sequences as well as proteins or complexes such as ribosomes and polymerases, which naturally accompany a native sequence. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule. An "isolated polypeptide" or protein carries a similar meaning with the polypeptide or protein being substantially separated from any cellular contaminants and components naturally associated with the protein in vivo.

The terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid, as well as to naturally occurring amino acid polymers.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

A "chimeric molecule" refers to a linked molecule obtained after conjugation of two or more different types of molecules (e.g., lipids, glycolipids, peptides, proteins, glycoproteins, carbohydrates, nucleic acids, natural products, synthetic compounds, an organic molecule, or an inorganic molecule).

The term "normal blood vessel formation" refers to the typical, usual, or natural process of forming or producing blood vessels in a subject.

The term "gene expression profile" or "gene expression pattern" means a profile or pattern based on the detection of mRNA for each gene to be included in the profile or pattern. mRNA can be detected at a particular time or under a particular condition(s), mRNA is extracted from cells, tissues, organs, or an entire organism of interest and detected. The amount or level of mRNA for a particular gene can be determined quantitatively.

The term "protein expression profile" or "protein expression pattern" means a profile or pattern based on the detection of a protein. The protein can be detected at a particular time or under a particular condition(s). Protein is extracted from cells, tissues, organs, or an entire organism of interest and detected. The amount or level of protein can be determined quantitatively.

The term "agent" includes any element, compound, or entity, such as, e.g., pharmaceutical, therapeutic, pharmacologic, environmental or agricultural pollutant or compound, aquatic pollutant, cosmeceutical, drug, toxin, natural product, synthetic compound, or chemical compound. Agents include known or potential inducers of an ocular disease as well as agent that have known or potential activity useful in therapeutically or prophylactically treating ocular disease.

The term "natural compound" includes a molecule isolated, extracted, or purified from a plant, animal, yeast, bacterium, or other microorganism. A natural compound includes, e.g., among other things, organic molecules belonging to the broad biochemical classes of peptides, proteins, glycoproteins, nucleic acids, carbohydrates, lipids, fats, glycolipids, as well as more complex molecules which comprise, e.g., elements of more than one of these basic biochemical classes.

The term "synthetic compound" includes a molecule synthesized de novo or produced by modifying or derivatizing a natural or existing synthetic compound.

"Developmental defect" means a deficiency, imperfection, or difference in the development of a tissue, organ, or other bodily component of an animal relative to normal development. Such a defect is identified as a change, difference, or lack of something necessary or desirable for completion or proper operation in the development of a tissue, organ, or other bodily component of the animal as compared with normal development of the component. Developmental defects include, for example, the failure of organ to develop properly, excess or reduced cell proliferation as compared to normal cell proliferation, and the mispositioning or malfunctioning of an organ or tissue.

Generally, the nomenclature used hereafter and the laboratory procedures in cell culture, molecular genetics, and nucleic acid chemistry described below are those well known and commonly employed in the art. Standard techniques such as described in Sambrook et al., MOLECULAR CLONING: A LABORATORY MANUAL (Cold Spring Harbor Laboratory, Cold Spring Harbor, N.Y., 2nd ed. 1989) and CURRENT PROTOCOLS IN MOLECULAR BIOLOGY, Vols. 1-3 (Virginia Benson Chanda ed., John Wiley & Sons, 1994-1998), each of which is incorporated herein by reference in its entirety for all purposes, are used for recombinant nucleic acid methods, nucleic acid synthesis, cell culture, and transgene incorporation, e.g., electroporation, injection, ingestion, and lipofection. Electroporation techniques utilize a pulse of high electrical current to introduce molecules of interest into cells, tissues, or organisms. Lipofection employs lipid-like cationic molecules that interact strongly with cell membranes, destabilizing them locally, thereby allowing DNA and RNA entry into cells. Generally, oligonucleotide synthesis and purification steps are performed according to the specifications.

The term "transgenic" in reference to an organism or animal includes those organisms or animals that have developed from a fertilized egg containing a foreign gene inserted into a chromosome. Such transgenic organisms and animals carry the foreign gene insert in every cell. Transgenic organisms and animals are created by using known techniques (see, e.g., Sambrook, supra and BIOCHEMISTRY WITH CLINICAL CORRELATIONS (T. Devlin ed., 3d ed. 1992), which is incorporated herein by reference in its entirety for all purposes). Transgenic organisms and animals can be used to study different aspects of the foreign gene, including the analysis of DNA regulatory elements, expression of proteins during differentiation, tissue specificity, and the potential role of oncogene products on growth, differentiation, and the induction of tumorigenesis. A "transgene" is a gene, in original or modified form, that has been introduced into an organism or animal that does not naturally have such gene. A "mosaically expressing transgene" is a transgene that is expressed randomly in a subset of the cells of the transgenic organism or animal. An "exogenous gene" is a gene from an organism or animal that does not belong to the species into which the gene has been introduced. A "transient transgenic animal" is transgenic animal which carries an introduced gene that is not inserted into a chromosome.

The term "founder fish" refers to, the fish from which a line of fish is generated. Usually, a founder fish is an individual fish which carries a unique mutation and which is used to generate progeny that also carry the mutation.

A "physiological activity" in reference to an organism is defined as any normal processes, functions, or activities of a living organism.

A "prophylactic activity" is an activity of an agent that, when administered to a subject who does not exhibit signs or symptoms of a disease or exhibits only early signs or symptoms of a disease decreases or prevents the risk in the subject of developing pathology or developing further pathology and or inhibits or delays the development of pathology or further pathology. A "therapeutic activity" is defined as any activity of an agent that reduces or eliminates pathological signs or symptoms or inhibits worsening of signs or symptoms when administered to a subject exhibiting the pathology. The term "therapeutically useful" in reference to an agent means that the agent is useful in reducing or eliminating pathological signs or symptoms of a pathology or disease. Prophylactic or therapeutic activity means an agent exhibits that activity in a screening system that indicates that the agent is or may be useful in the prophylaxis or treatment of a disease, particularly by the methods of the present agent. Agents can be described as having such activity notwithstanding that further testing may be required to establish prophylactic or therapeutic utility for in treatment of a in humans disease.

The term "toxic activity" is defined as any activity of an agent that has a detrimental or undesired effect on a normal physiological state (e.g., normal physiological function or morphology) or aggravates a disease state when administered to a subject. A detrimental or undesired effect on a normal physiological state can be, for example, at any one or more of the molecular, biochemical, cellular, histological, organic, or systemic levels of physiology. In the particular context of toxic activity as it relates to morphological changes, toxic activity can include, for example, a change in size, shape, pigmentation, color, or structure (such as, e.g., of an organ or tissue). Accordingly, toxic activity can include, for example, any of a variety of structurally-related defects (e.g., in the case of defects in vessel structure, a toxic activity can include, for example, edema or hemorrhage). A detrimental or undesired effect on a normal physiological state can include, for example, inducement of or increase in cell death activity.

DETAILED DESCRIPTION OF THE INVENTION

I. General

Figure 1:
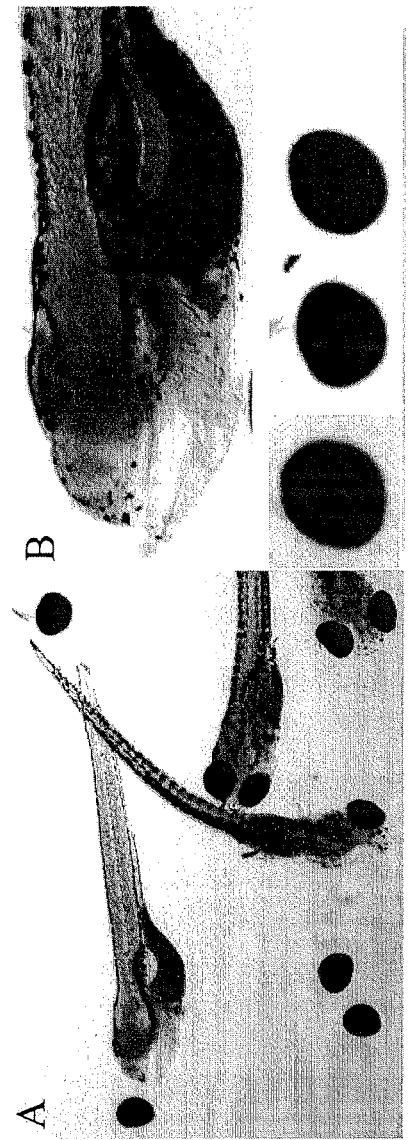
FIG. 1 shows removal of eyes from 5 dpf zebrafish using collagenase treatment. Zebrafish were treated with 150 U/ml collagenase for 45 minutes at 37° C. The eyes were removed by gentle pipetting (A). Both the isolated eyes and zebrafish remain intact (B).

The present invention is generally directed to methods of screening an agent for an activity in an isolated eye of a teleost. Following treatment of a teleost with an agent in vivo, an eye of the teleost is isolated and evaluated for the presence or absence of a response indicating an activity. Advantages of using isolated eyes for screening for an activity in a teleost include, for example, the ability to focus on the agent's activity in the eye without interference from other organs or tissues, as well as greater sensitivity and/or specificity of readouts of experimental assays when the eye is separated from the remaining organs and tissues of the animal.

An agent can be evaluated for an ocular or ophthalmologic activity in the eye of a teleost, including, for example, a desired (e.g., therapeutic or prophylactic) activity, or for a cell death or toxic activity. Optionally, an agent is evaluated for multiple activities (including, e.g., desired and undesired activities). For example, an agent can be evaluated for at least two activities in an isolated eye. The multiple activities can, for example, at least two activities selected from an ocular activity, a cell death activity, and a toxic activity. Alternatively, an agent can be evaluated for an activity in the eye of the teleost (e.g., an ocular or ophthalmologic activity) and at least one other activity (e.g., a cell death or toxic activity) in at least one other organ or tissue of the teleost. In such variations, the teleost can be evaluated for the second activity either before or after separation of the eye from teleost.

This Section of the application discusses general considerations in screening an agent for an activity in an isolated eye of a teleost. Section II discusses additional considerations for screening an agent for an activity in an isolated eye of a teleost model of an ocular disease or disorder. Section III describes methods of isolating an eye from a teleost (Section III). Section IV describes methods of screening an agent for cell death and/or toxic activity in a teleost. Section V describes high throughput screening methods using teleosts are described. Each of these methods can be used in conjunction with screening an agent for an ocular or ophthalmologic activity in accordance with the present invention.

A. Animal Models

The methods of the present invention, which are directed to screening agents for an ocular or ophthalmologic activity, are generally applicable for use in teleosts. Particularly suitable teleosts include, for example, zebrafish (*Danio rerio*), Medaka, Giant rerio, and puffer fish. Teleosts offer important advantages over other animal model systems for use in screening methods. First, these teleosts are vertebrates whose genetic makeup is more closely related to that of man than are other models, such as the *Drosophila* and nematode. Zebrafish are amenable to genetic screening for visual defects, because they can be bred and maintained with minimal resources and because their sophisticated visual system develops rapidly. Zebrafish have color vision mediated by red, green, blue, and UV-sensitive cone photoreceptors. They also have scotopic vision mediated by rod photoreceptors. Photoreceptor outer segments appear at 55 hours ostfertization and by 3 days postfertilization (dpf) zebrafish have rudimentary visual function. By 5 dpf photoreceptors have developed sufficiently to screen for visual behavior, although rod function is not distinguishable from cone function until 2 weeks postfertilization. All essential components of human form and organ development are mimicked in these teleosts and the morphological and molecular bases of tissue and organ development are either identical or similar to other vertebrates, including man. (See Chen and Fishman, Development 123:293-302, 1996; and Granato and Nusselien-Volhard, Cur. Op. Gen, Dev. 6:461-468, 1996.) As a result, these teleosts serve as an excellent model for the study of vertebrate development and human disease states.

Second, these teleosts provide advantageous animal models because their embryos are very transparent. Given the transparency of the embryo, angiogenesis activity, cell death activity (e.g., apoptosis and necrosis), and toxic activity produced by administered agents can be detected and diagnosed much more rapidly than in non-transparent animals. These activities can also be detected in the more mature larval and adult forms of the zebrafish, though somewhat less readily as such forms become progressively less optically clear. These activities can also be detected in vivo in all three forms or in cells thereof in vitro. By contrast, the mouse, which is commonly used as an animal model system, is an opaque animal and does not allow a similar rapid or in vivo assessment of phenotypic or developmental changes, including those associated with cell death, angiogenesis, or toxicity, in whole animal or whole organs or tissues. Significantly, precursor tissues and components of the brain, eyes, heart, and musculature of these teleosts are detected and visualized much more easily and quickly in the transparent teleosts than in other systems, including other vertebrate systems (such as the mouse) by a variety of detection techniques, including, e.g., light microscopy, fluorescence microscopy, colorimetry, chemiluminescence, digital imaging, microplate reader techniques, or in situ hybridization of RNA. High content imaging systems (HCS) from e.g., GE, Cellomics or Molecular Devices are particular useful in the methods of the invention.

Another important advantage of teleosts over other animal models is that teleosts develop much more rapidly than do other animal models. In general, the body plan, organs, tissues, and other systems of teleosts develop much more rapidly than do such components in other vertebrate model systems (e.g., the mouse). The entire vertebrate body plan of the zebrafish, for example, is typically established within 24 hours. A functioning cardiovascular system is evident in the zebrafish within the first 24 hours of development. (See Stainier and Fishman, *Trends Cardiovasc. Med.* 4:207-212, 1994.) Many of the remaining organs of the zebrafish, including the kidney and vasculature, are established within 48 hours of development. By 72 hours of development, the zebrafish has a functional hemispheric eye, along with fully faulted gut and liver. (See Schmitt and Dowling, *J. Comp. Neurol.* 344:515-536, 1994; Li et al., *Dev. Dyn.* 218:175-188, 2000; and Soules and Link, *BMC Dev. Biol.* 5:12-27, 2005.) The hatched zebrafish embryo nearly completes morphogenesis within 120 hours of development, thereby making it highly accessible to manipulation and observation and amenable to high-throughput automated observation and detection procedures.

Figure 9:
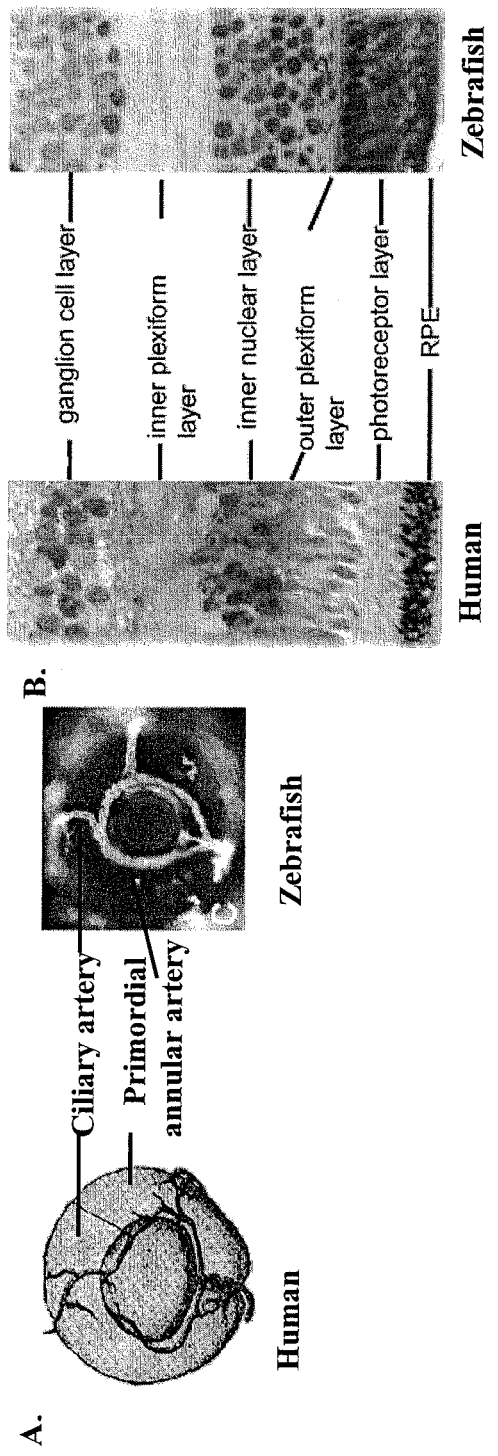
FIG. 9 shows that eye development in humans and zebrafish is similar. (A) Early vasculature. Illustration of 10 mm human (left) embryo eye and zebrafish (right) embryo eye stained with a endothelial vessel-specific monoclonal antibody, Phy-V (Phylonix) 2 days post-fertilization (dpf). (B) Retina structure. The layers of neuronal and photoreceptor cells are arranged in a similar pattern in humans (left) and zebrafish (right) (see Goldsmith and Harris, Semin. Cell Dev. Biol, 14:11-18, 2003).

The morphogenesis of the zebrafish eye is similar in many respects to that of other vertebrates (FIG. 9). (See Schmitt and Dowling, supra; Li et al., supra; and Soules and Link, supra.) In addition, there are several genetic mutants in zebrafish known in the art that display altered eye development, as well as experimentally-induced eye abnormalities (Li et al., supra). Zebrafish are useful models for studying the genetics and biology of visual disorders and diseases, for example, glaucoma and retinal degeneration. (See McMahon et al., *Comp. Biochem. Physiol. C. Toxicil. Pharmacol.* 138:343-350, 2004; Goldsmith and Harris, supra; Goldsmith, *Neuroreport.* 12:A73-A77, 2001.)

The zebrafish eye develops at early stages and visual behavior has been monitored as early as 48 to 96 hours post-fertilization (hpf). The optic primordium appears at ~12 hpf and the first ganglion cells appear at 30 hpf Cones begin to develop at 60 hpf. Furthermore, the architecture of the zebrafish eye is strikingly similar to the structure of the human eye (see FIG. 9 and Goldsmith and Harris, *Semin. Cell. Dev. Biol.* 14:11-8, 2003). The laminar arrangement of the various cell types in the retina consists of orderly rows of cells separated by layers of their synaptic processes. A single tract of axons connects the retina with the rest of the brain. The hyaloid vasculature surrounding the lens and the developing choroid vasculature at the back of the eye are present by 2 days post-fertilization (dpf). The choroidal vascular plexus is well formed and the hyaloid vessels appear to have regressed by 5 dpf (Isogai et al., *Dev. Biol.* 230:278-301, 2001). The zebrafish anterior segment is established very rapidly and rudimentary structures of the anterior segment are present by 3 dpf. Extensive growth and morphogenesis occurs until 1 month when the eye reaches its mature form (see Soules and Link, supra). The zebrafish adult cornea, which is fully formed at 6 months post-fertilization (mpf), is approximately 20 µm thick and contains all five major layers found in the human cornea: the epithelium, Bowman's layer, stroma, Descemet's membrane, and endothelium (see Zhao et al., *Invest. Ophthalmol. Vis. Sci.* 47:4341-4348, 2006). The zebrafish conjunctiva and sclera develop in the mature form with the zebrafish anterior segment and cornea growth, which provides an anatomical foundation to establish a scarring area between the conjunctiva and sclera or in the sclera, similar to human scar formation after GFS.

The pharmacologic activity of an agent (ocular or ophthalmologic activity, optionally together with cell death and/or toxic activity) and responses indicating these activities can be monitored in whole teleosts and/or in vivo or in cells thereof in vitro over time, a procedure not possible or readily practiced with other animal embryos which develop in utero, such as the mouse. Moreover, the effects of an agent on the whole teleost embryo or on more than one system (e.g., cardiovascular system, enteric system, and musculature system), organ (e.g., eye), or tissue can be detected simultaneously using transparent teleosts. The persistence of such effects can be monitored by using simple visualization methods and over selected time intervals. By comparison, it is extremely difficult to detect and assess developmental and phenotypic changes in organs, tissues, and systems (such as inhibition or enhancement of angiogenesis, cell death or toxic activity due to an agent) over time in animals which develop in utero. Mouse embryos, for example, must be removed from the mother—a labor intensive procedure—before an assay can be performed.

Teleosts also offer the advantage that agents to be evaluated for toxic effects can be administered directly to the developing teleost. Direct introduction of candidate compounds is hindered in animals which develop in utero, such as the mouse embryo. Further, the teleost embryo is an intact, self-sustaining organism. It is different from a mouse embryo, for example, which because it is physically removed from its mother's womb, it is not self-sustaining or intact; a mouse embryo would function more as an "organ" culture or the like.

Zebrafish assays are much less expensive than mouse assays. A single mating of a zebrafish produces 100-200 eggs. Inbred strains are available and thousands of zebrafish can be raised inexpensively in a small room of aquaria. Moreover, teleost eggs, including those of the zebrafish, are externally fertilized. Teleost embryos (such as zebrafish) can survive by diffusion of oxygen from the water and nutrients from the yolk and thus even the absence of the entire circulatory system is well tolerated during early development. (See Weinstein et al., *Nature Med.* 1:1143-1147, 1995.)

Additionally, single whole teleost embryos can be maintained in vivo in fluid volumes as small as 100 microliters for the first six days of development. Intact live embryos can be kept in culture in individual microtiter wells or multi-well plates. Test compounds can be added directly to the medium in which the fish is immersed. Compounds permeate the intact embryo directly, making this multi-well format particularly attractive for high throughput and automated compound screening. Both therapeutic activities and side effects (e.g., cell death and toxicity) of a drug can be assayed in the teleost simultaneously in vivo.

The teleosts used with the screening methods of the invention are typically early-stage teleost embryos; however, transparent larval or adult teleosts can also be used. Wild-type strains of teleosts are usually employed. Wild-type strains are typically maintained for about one year, after which time fertility decreases. Mutant strains of teleosts (such as zebrafish) can be used to assess, e.g., the interaction between therapeutic agents and specific genetic deficiencies. The teleost can contain a mutation in a selected gene (e.g., associated with an ocular disease or disorder). The mutation can be a heritable mutation, including, e.g., a heritable mutation associated with a developmental defect in the eye. The teleost can also be transgenic.

B. Agents to be Screened

A variety of agents from various sources can be screened for enhancing or inhibiting an ocular or ophthalmologic activity, cell death activity, and/or toxic activity, by using the methods of the present invention. Agents to be screened can be naturally occurring or synthetic molecules. Agents to be screened can also obtained from natural sources, such as, e.g., marine microorganisms, algae, plants, fungi. Alternatively, agents to be screened can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Agents can include, for example, pharmaceuticals; therapeutics; ocular toxicants (e.g., cobalt chloroid); environmental, agricultural, or industrial agents; pollutants; cosmeceuticals; drugs; organic compounds; lipids; nucleic acids; glucocorticoids; antibiotics; peptides; proteins; sugars; carbohydrates; chimeric molecules.

Combinatorial libraries can be produced for many types of compounds that can be synthesized in a step-by-step fashion. Such compounds include polypeptides, proteins, nucleic acids, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of compounds can be constructed by the encoded synthetic libraries (ESL) method described in WO 95/12608 (Affymax), WO 93/06121 (Affymax), WO 94/08051 (Columbia University), WO 95/35503 (Pharmacopeia), and WO 95/30642 (Scripps), each of which is incorporated herein by reference in its entirety for all purposes. Peptide libraries can also be generated by phage display methods. See, e.g., WO 91/18980 (Devlin). Compounds to be screened can also be obtained from governmental or private sources, including, e.g., the National Cancer Institute's (NCI) Natural Product Repository, Bethesda, Md., the NCI Open Synthetic Compound Collection, Bethesda, Md., NCI's Developmental Therapeutics Program, or the like.

C. Administration of Agents

Agents to be screened for an effect on ocular or ophthalmologic activity, cell death activity, and/or toxic activity can be administered to the teleost by adding the agent directly to the media containing the live teleost. Alternatively, the agent can first be dissolved in the media and the live teleost submerged in the media subsequently. Such approaches have been used to introduce anesthetics and other chemicals to fish embryos. See, e.g., M. Westerfield, THE ZEBRAFISH BOOK: A GUIDE FOR THE LABORATORY USE OF ZEBRAFISH (3d, ed. 1995), which is incorporated herein in its entirety for all purposes. Agents can also be administered to the teleost by using microinjection techniques in which the agent is injected directly into the live teleost. For example, agents can be injected into either the yolk or body of a teleost embryo or both.

Agents can also be administered to teleosts by electroporation, lipofection, or ingestion or by using biolistic cell loading technology in which particles coated with the biological molecule are "biolistically" shot into the cell or tissue of interest using a high-pressure gun. Such techniques are well known. (See, e.g., Sambrook et al., supra; Chow et al., Amer. J. Patha 2(6):1667-1679, 1998.)

Agents can be administered alone, in conjunction with a variety of solvents (e.g., dimethylsulfoxide or the like) or carriers (including, e.g., peptide, lipid or solvent carriers), or in conjunction with other compounds.

Agents can be administered to the teleost before, at the same time as, or after administration of a dye used for detection of the response in the animal indicating a specific activity (e.g., ocular or ophthalmologic activity and/or toxic activity). Optionally, a plurality of agents can be administered to the same teleost(s), together or serially.

D. Administration of Dyes

A dye used in methods of screening agents for an activity (e.g., ocular or ophthalmologic activity, cell death activity, and/or toxic activity) can be administered to the teleost by adding the agent directly to the media containing the live teleost. Alternatively, the dye can first be dissolved in the media and the live teleost submerged in the media subsequently. (See, e.g., Westerfield, supra.) Dyes can also be administered to the teleost by using microinjection techniques in which the dye is injected directly into the live teleost. Dyes can be injected into either the yolk or body of a teleost embryo or both.

Dyes can be administered alone, in conjunction with a variety of solvents (e.g., dimethylsulfoxide or the like), or in conjunction with other dyes. Dyes can be administered to the teleost before, at the same time as, or after administration of a dye used for detection of the response in the teleost indicating a specific activity (e.g., ocular or ophthalmologic activity, cell death activity, and/or toxic activity). When fluorescent dyes are used (e.g., unsymmetrical cyanine dye, such as a quinolium dye) for detection of an activity (e.g., cell death activity), the dye is preferably administered prior to administration of the agent.

E. Detecting Agent Activity and Responses in Teleosts

Generally, an administered agent is assessed for an activity by measuring a response in an isolated eye (and/or in at lease one other organ or tissue of the teleost) associated with or otherwise indicative of the activity. A response can be determined by e.g., a change in the level of a molecule (e.g., a protein) or a process relative in a an eye treated with the agent relative to a historical or contemporaneous control eye not treated with the agent. Measurement of a response can be qualitative (i.e., response is present or absent) or quantitative (the degree of the response is measured). A response to an agent can include, for example, a physiological change (e.g., an increase or decrease in a physiological, cellular, or biochemical process) in the isolated eye or teleost, including, e.g., a change in mRNA levels or in protein expression; a change in cell-surface marker expression; a change in proliferation, differentiation, or migration of cells; a change in cellular viability; a morphological change in a tissue or organ; a changes in cell signaling; a metabolic change; and the like. In certain embodiments, the detection of a response includes the detection of a target biomolecule, such as, for example, a target protein, mRNA, lipid, or the like. The particular response to be detected varies according to the activity for which an agent is screened.

A variety of techniques can be used together or separately to generate a signal and to detect and assess the effects of an agent on ocular or ophthalmologic activity, cell death activity, and/or toxic activity of an agent. Signals can be generated by, for example, in situ hybridization, antibody staining of specific proteins (e.g., antibody markers that label angiogenic, vessel formation in teleosts, including Phy-V, terminal deoxyuridine nucleotide end labeling to detect dead or dying cells), and the like. Responses indicating ocular or ophthalmologic activity, cell death activity, and/or toxic activity can be detected by, e.g., visual inspection, colorimetry, fluorescence microscopy, light microscopy, digital interference contrast (DIC) microscopy, chemiluminescence, digital image analyzing, standard microplate reader techniques, fluorometry, including time-resolved fluorometry, visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube. Responses can be discriminated and/or analyzed by using pattern recognition software. Agents are identified and selected using the screening methods according to the activities and responses they produce.

Changes in the distribution of a protein both spatially and temporally, including a complete absence of a protein, can be detected and protein expression profiles can be generated. Changes in a level of an enzyme or enzymatic activity within the intact teleost can also be detected by various means, including, e.g., use of streptavidin (avidin) conjugated reporter enzyme to detect naturally biotinylated carboxylase enzymes in the liver, gut, and digestive tube of animals.

F. Automated Methods

In addition to manual screening methods, the present invention also provides methods for rapid screening of agents for activities, such as ocular or ophthalmologic activity and/or toxic activity, using automated procedures. Such automated methods can be readily performed by using commercially available automated instrumentation and software and known automated observation and detection procedures. Multi-well formats are particularly attractive for high throughput and automated compound screening. Screening methods can be performed, for example, using a standard microplate well format, with a whole zebrafish embryo in each well of the microplate. This format permits screening assays to be automated using standard microplate procedures and microplate readers to detect enhancement or inhibition of angiogenesis activity in the zebrafish embryos in the wells. A microplate reader includes any device that is able to read a signal from a microplate (e.g., 96-well plate), including fluorometry (standard or time-resolved), luminometry, or photometry in either endpoint or kinetic assays. Using such techniques, the effect of a specific agent on a large number of teleosts (e.g., teleost embryos) in vivo can be ascertained rapidly. In addition, with such an arrangement, a wide variety of agents can be rapidly and efficiently screened for their respective effects on the cells, tissues or organs of teleosts contained in the wells.

Sample handling and detection procedures can be automated using commercially available instrumentation and software systems for rapid reproducible application of dyes and agents, fluid changing, and automated screening of target compounds. To increase the throughput of a compound administration, currently available robotic systems (e.g., BioRobot 9600 from Qiagen, Zymate from Caliper, or Biomek from Beckman-Coulter Instruments)—most of which use the multi-well culture plate format—can be used. The processing procedure involves a large number of fluid changes that must be performed at defined timepoints. Non-automated throughput is typically 5 microtiter plates per investigator (400 teleost embryos and 20 compounds) per week based on using a 96-well plate with 1 embryo per well and screening 2 concentrations with 10 embryos per concentration. Using currently available fluid handling hardware (e.g., Bodhan Automation, Inc., Caliper) and our standard sample handling procedures, 50-100 plates per day (4800-9600 teleost embryos and 200-400 compounds) can be processed. Incorporation of commercially available fluid handling instrumentation significantly reduces the time frame of manual screening procedures and permits efficient analysis of many agents, including libraries of agents.

G. Other Considerations

The methods of the present invention are amenable to any of a variety of screening formats. As previously described above, the present methods can be performed, e.g., using a multi-well format. In certain variations of this embodiment, one or more intact teleost(s) are cultured (and treated with one or more agents, as appropriate to any specific embodiment) in one or more wells of a multi-well plate, such as a microtiter plate (or multiple teleosts cultured and treated in wells of a plurality of multi-well plates). Following culture and treatment with an agent, eyes are dissociated from the teleost(s) as described herein. The isolated eyes are typically transferred to an appropriate vessel or substrate for further processing and evaluation to determine one or more activities or responses induced by the agent in the eye(s). For example, in some embodiments, the isolated eyes are transferred to one or more wells of a second multi-well plate (or second plurality of multi-well plates). Optionally, the isolated eyes are transferred in such a manner as to preserve the relationship between eyes and wells. That is, the second multi-well plate has corresponding wells to the wells of the first multi-well plate and the eyes are transferred such that corresponding wells contain the same eye(s) before and after transfer.

In some alternative variations, teleosts are cultured and treated in a larger (e.g., non-multi-well) vessel (e.g., a non-multi-well culture flask) and, following dissociation of eyes, isolated eyes are transferred to appropriate vessel(s) or substrate(s) for evaluation. For example, the isolated eyes can be transferred to wells of one more multi-well plate(s), to a second non-multi-well vessel, or placed on one or more substrates such as, e.g., one or more slide(s).

Alternatively, eye(s) can be analyzed in the same well(s) in which they are isolated. Optionally, the body(ies) of the teleost(s) can be removed before analyzing the eyes.

Treatments can be performed on each of one or more teleosts cultured singly in individual wells of a multi-well plate (e.g., microwells of a microplate) or, in some alternative embodiments, a plurality of teleosts can be treated in larger wells (e.g., wells of a 6-well or 24-well plate) or other larger (e.g., non-multi-well) vessels. Teleosts can be cultured in a volume of culture medium from 50-1000, 50-500, 50-250, 100-500, or 100-250 µl of culture medium per well (depending in part on the type of multi-well plate and size of the wells, and number of zebrafish per well). In some embodiments, about 30 or more teleosts are treated together in the same well or other culture vessel.

Depending on the nature of the activities or responses to be evaluated in the isolated eye and/or teleost, additional processing (e.g., additional fixation steps and/or staining procedures) can be performed on the eye following isolation. For example, in some embodiments, an intact teleost can be fixed following administration of an agent as part of a procedure for measuring a response or activity (e.g., an antibody or enzymatic-based staining procedure). The eye of the teleost can then be isolated as described herein, followed by additional processing steps for detection of the response or activity (e.g., staining with a labeled antibody specific for a protein marker of interest). In certain alternative embodiments, the intact teleost is processed up to the point at which no further substantial processing of the isolated eye is needed, other than removal of the eye as described herein and detection of an appropriate signal (e.g., fluorescence or chemiluminescence) using appropriate instrumentation.

In addition, when screening for multiple activities of an agent, where at least one activity is an activity to be screened in the eye (e.g., ocular or ophthalmologic activity) and at least one activity in at least one other organ or tissue of the teleost, the activity to be assayed in the at least one other organ or tissue of the teleost can be evaluated either before or after isolation of the eye from the teleost. For example, in some embodiments, where isolation of the eye leaves other organs or tissues substantially non-intact, the detection of the activity in the at least one other organ or tissue can be carried out before isolation of the eye. In certain other variations where the teleost body remains substantially intact following separation of the eye, the activity in the at least one or organ or tissue can be performed either before or after eye isolation.

II. Screening Agents for an Activity in an Isolated Eye of a Teleost Model for Ocular Disease A. Teleosts as Animal Models for Ocular Diseases and Disorders Teleosts, such as, e.g., zebrafish, can be used as a model to screen for agents for an ocular or ophthalmologic activity (e.g., therapeutic or prophylactic) in the isolated eye of a teleost in which the phenotype of a human ocular disease or disorder has been mimicked, as well as to screen agents or toxic and/or cell death activities in a teleost or teleost eye. Examples of ocular diseases or disorders specific for the eye for which therapeutic and/or prophylactic treatments are desired are provided in Table I, infra These and other ocular conditions can be mimicked in the teleost (e.g., zebrafish) using a variety of tools available in the art, including, for example, available mutants, gene knockdown tools, and/or treatments. Mutant or transgenic fish can be used, e.g., as models for toxicity, or models for protection, depending on the mutation or transgene inserted. Transgenic fish containing transgenes with genes expressed in the eye, or knockouts of such genes are particularly useful, as are mutants in genes expressed in the eye. Optionally, transgenes include a gene expressed in the eye linked to its own or other promoter preferentially expressed in the eye (see e.g., EP 1 456 375). Treatments for inducing an ocular condition include, e.g., microsurgical treatment or treatment with a compound, such as a toxicant or a drug. (A compound-induced condition in a teleost, for generating a model of a disease or disorder, is also referred to as a chemical phenocopy for that disease or disorder.) Exemplary zebrafish models for choroidal neovascularization (CNV) induced by $CoCl_2$ treatment (one of the phenotypes observed in an advanced form of age-related macular degeneration (AMD)) and ocular scarring induced by microsurgery (such as occurs, e.g., following surgery for glaucoma) are further described in Examples 1 and 2, infra

TABLE I

Ophthalmic Diseases Specific for the Eye

| Blindness | Retinal Diseases | Other Eye Diseases & Disorders |
|---|---|---|
| Cataracts | Macular dystrophies | Choroidal hemorrhage |
| Glaucoma | Choroidal dystrophies | Proliferative vitreoretinopathy |
| Age-related macular degeneration (AMD) | Congenital stationary night blindness | Posterior segment ocular trauma |
| Trachoma | Hereditary vitreoretinopathics | Distant trauma with posterior segment effects |
| Corneal opacity | Hypertensive retinopathy | Light toxicity and laser burns |

TABLE I-continued

Ophthalmic Diseases Specific for the Eye

| Blindness | Retinal Diseases | Other Eye Diseases & Disorders |
|---|---|---|
| Diabetic retinopathy | Retina arterial obstruction | Toxic retinopathies |
| Retinitis pigmentosa and related disorders | Venous obstructive disease of the retina | Persistent fetal vasculature syndrome |
| | Retinopathy of prematurity | Intraocular tumors |
| | Ocular ischemic syndrome | Uveitis and other intraocular inflammations |
| | Hemoglobinopathies | Neuro-ophthalmic diseases |
| | Coats' disease and retinal telangiectasia | External diseases |
| | Radiation retinopathy and papillopathy | Extraocular muscle problems |
| | Proliferative retinopathies | Refractive errors |
| | Retinal arterial macroaneurysms | |
| | Choroidal neovascularization (CNV) | |
| | Degenerative myopia | |
| | Central serous chiororoetinopathy | |
| | Macular hole | |
| | Epiretinal membrane | |
| | Vitreomacular traction syndrome | |
| | Cystoid macular edema | |
| | Coexistent optic nerve and macular abnormalities | |
| | Angioid streaks | |
| | Peripheral retinal lesions | |
| | Retinal breaks | |
| | Rhegmatogenous retinal detachment | |
| | Serous detachment of the neural retina | |

1. Age-Related Macular Degeneration

Age-related macular degeneration (AMD) is the leading cause of blindness in adults over 60, affecting more than 50 million people worldwide (Klein et al., Am J. Ophthalmol. 137:486, 2004). AMD begins with characteristic yellow deposits in the retina, called drusen. Drusen are thought to be fatty waste products from the photoreceptor cells. Early AMD is associated with thinning of the macula and the appearance of drusen in the macula area. Most people with early AMD have good vision; however, persons with drusen may develop advanced AMD, which is associated with profound vision loss, which can be gradual or sudden. "Hard" drusen is common in aging eyes, and does not necessarily lead to AMD, whereas irregular and ill-defined "soft" drusen often indicates vision problems in the near future.

AMD, which is responsible for profound vision loss, has two forms: dry and wet. The "dry" form is an early form of AMD, thought to progress into a more advanced "wet" form. Central geographic atrophy, a dry form of AMD, causes vision loss through loss of photoreceptors and cells supporting the photoreceptors in the central part of the eye. The wet form of AMD is associated with sudden vision loss due to abnormal blood vessel growth (i.e., choroidal neovascularization) under the macula.

The choroidal neovascularization zebrafish model discusses in the examples provides a model of the wet form of human AMD.

Mutations in the zebrafish ELOVL4 gene cause an early onset autosomal dominant form of macular degeneration (Investigative Ophthalmology and Visual Science. 2003;

44:2841-2850). A transgenic zebrafish expressing a mutant ELOVL4 in the photoreceptors is being studied as a model of the human condition.

2. Glaucoma

Figure 7:
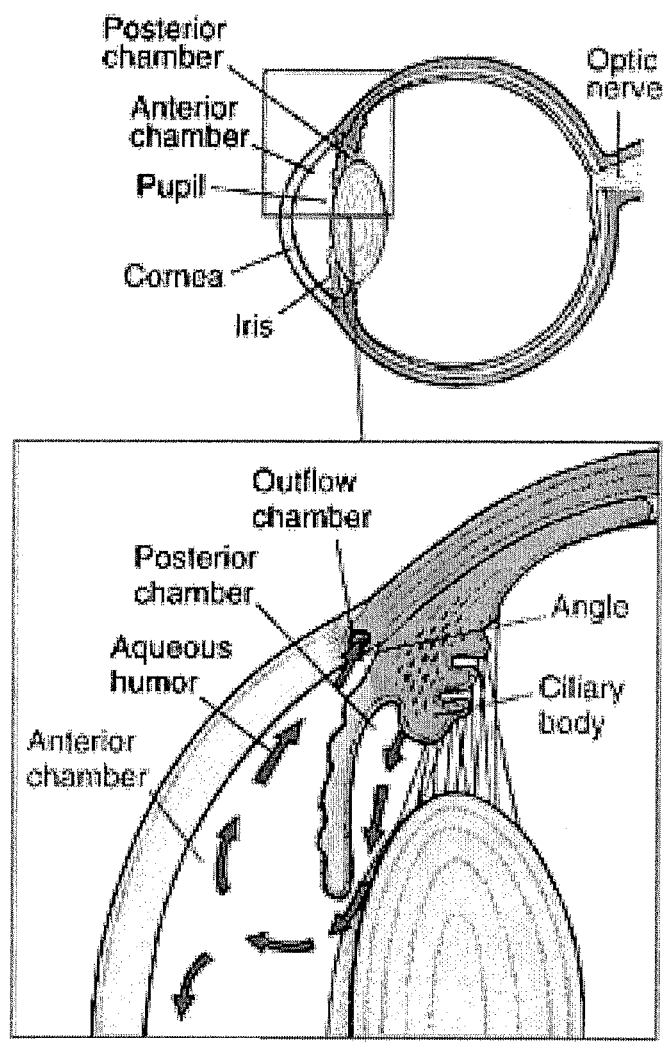
FIG. 7 shows normal fluid drainage from the eye. Fluid produced in the ciliary body behind the iris (posterior chamber) passes into the front of the eye (anterior chamber), and drains through the drainage canals (anterior angle and trabecular meshwork).

Background on Glaucoma. There are two types of primary glaucoma: open-angle glaucoma and angle-closure glaucoma. FIG. 7 shows normal fluid drainage—fluid is produced in the ciliary body behind the iris (posterior chamber), passes into the front of the eye (anterior chamber), and then drains through the drainage canals (anterior angle and trabecular meshwork). The most common form of glaucoma is primary open-angle glaucoma, where the aqueous fluid that normally circulates in the front portion of the eye is blocked from flowing out of the eye through the drainage system. This process causes the pressure inside the eye to increase, which can damage the optic nerve and lead to vision loss. Most people who develop primary open-angle glaucoma notice no symptoms until their vision is impaired. In angle-closure glaucoma, the iris may completely close off the drainage angle, abruptly blocking the outflow of aqueous fluid leading to increased IOP or optic nerve damage. In acute angle-closure glaucoma, there is a sudden increase in IOP due to the buildup of aqueous fluid. This condition is critical because optic nerve damage and vision loss can occur within hours. Symptoms include nausea, vomiting, seeing haloes around light, and eye pain. Angle closure glaucoma can result in a rapid increase in the IOP when drainage of the fluid stops.

Incidence of Glaucoma. Glaucoma is a common visual disorder characterized by elevated or abnormal intraocular pressure (IOP) and optic neuropathy. After cataracts, glaucoma is the second leading cause of vision loss worldwide and the third leading cause of blindness after age-related macular degeneration and cataracts in the United States. It is estimated that 65 million people are affected by glaucoma worldwide and that over 2 million Americans have the disease (see Quigley, Br. J. Ophthalmol. 80:389-393, 1996; Munoz and West, Br. J. Ophthalmol. 86:498-504, 2002; Quigley and Broman, Br. J. Ophthalmol. 90:262-267, 2006). In humans, there are three primary forms of glaucoma: 1) congenital/hereditary; 2) primary open angle; and 3) primary angle closure. According to epidemiological information in the World Health Organization's global data bank on blindness, primary open angle glaucoma was judged to be responsible for three million cases of blindness, primary angle closure glaucoma was responsible for two million cases, and congenital glaucoma was responsible for 200,000 cases, totaling 5.2 million cases of blindness. This represents 15% of global blindness (see Thylefors and Negrel, Bull. World Health Organ. 72:323-326, 1994). In the United States, approximately 2-3% of Caucasians and 8-10% of African-Americans will acquire glaucoma during their life-times (see Quigley and Vitale, Invest. Ophthalmol. Vis. Sci, 38:83-91, 1997). Treatment of glaucoma is an important therapy for preventing blindness and new animal models and improved methods for drug screening are urgently needed.

Figure 8:
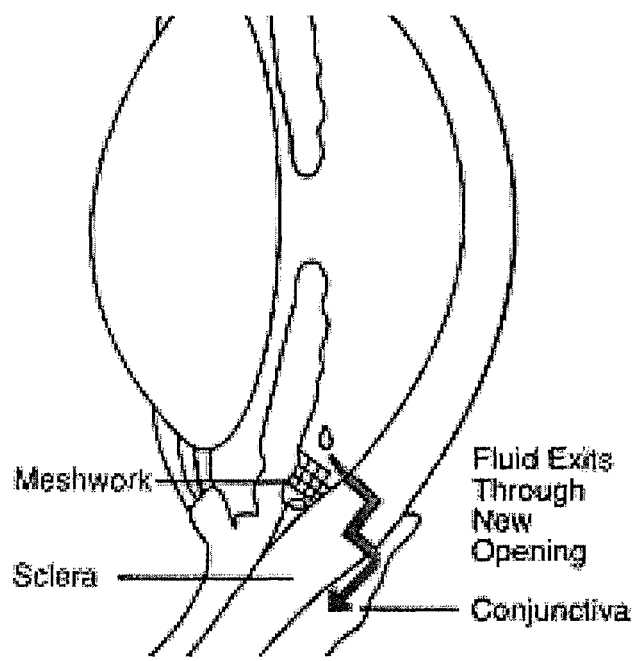
FIG. 8 shows that trabeculectomy improves fluid drainage. Trabeculectomy builds a new channel in the trabecular meshwork so that fluid can drain to decrease IOP in glaucoma.

Trabeculectomy and Glaucoma Filtration Surgery (GFS). Lowering IOP has been shown to be effective in reducing optic nerve damage. In congenital/hereditary and primary open angle glaucomatous patients, when medication fails to adequately control IOP, GFS may be performed. In primary angle closure glaucomatous patients, GFS (trabeculectomy or laser surgery) may be performed immediately to lower TOP if there is a clear diagnosis; post GFS, especially post trabeculectomy, scars form rapidly in the eye. Trabeculectomy, the most common form of GFS, prevents or reduces damage to the optic nerve by creating a fistula through the sclera at the limbus into the anterior chamber thereby reducing IOP. This procedure permits aqueous humor to drain into the subconjunctival space, creating an elevated bleb of Tenon's capsule and conjunctiva. Aqueous in the bleb is eventually reabsorbed by surrounding tissue. In this procedure, a small incision is made in the sclera of the eye and a flap of tissue is left to cover the incision, allowing slow release of fluid from inside the eye to the outer layer through the new channel (see FIG. 8). A significant complication with GFS is fibroblast and fibrovascular proliferation that results in scar formation. Without the use of anti-scarring agents, most GFS fails after 1 year. Based on records from the National Hospital Discharge Survey and the National Survey of Ambulatory Surgery (see Hall et al., Advance Data from Vital and Health Statistics, no. 316, 1998; Owings et al., Vital and Health Statistics, 13:132, pp. 33-113, 1998), there were an estimated 145,000 trabeculectomy surgeries performed in the United States in 1996 and at least a 30% increase is expected by 2008. Overall success rates for trabeculectomy range from 24-75%. This variability results from scarring on the conjunctiva that can effectively close the fistula within the first year after surgery. Long-term failure of GFS results in repeat surgery and is generally the result of excessive subconjunctival scarring that develops at the surgical site. In most cases, this failure is caused by a wound healing response at the level of the episclera and the deep fibrovascular layers of Tenon's capsule that evoke a permanent increase of outflow resistance or even complete occlusion. Pulse labeling studies in non-human primates indicate that the major proliferative stage of the wound healing response occurs during the first 2 weeks after surgery (see Jordan et al., Br, J. Ophthalmol. 87:870-875, 2003). Fibroblasts have been identified as the primary cell type which produces new tissue surrounding the scleral flap and these cells have been shown to play an essential role in wound healing in other locations of the body. New anti-fibroblastic drugs are under development to influence and modify the wound healing response following GFS.

The Process of Scarring. After surgery, wound healing occurs. Wound healing, which ordinarily starts immediately after surgery, takes places in three stages: inflammation, proliferation, and maturation. During the inflammation stage, platelets, macrophages, and leukocytes infiltrate the wound site and release cytokines and growth factors, which are required during the proliferation stage. Repair takes place during the proliferation stage; re-epithelialization, collagen deposition, and angiogenesis begin to repair destroyed tissue and provide oxygen, nutrients, and to form granulation tissue. In the final maturation stage, proteases degrade excessive collagen at the wound site to complete tissue repair. Although granulation is classically assigned to the proliferation stage, angiogenesis begins immediately upon wounding and persists throughout the healing process. During the three stages of the healing process, fibroblast cells and new vessels comprised of endothelial cells (angiogenesis) proliferate, which results in scar formation in the surgical area.

Current Anti-Scarring Agents. Current anti-scarring agents include anti-fibroblastic and anti-metabolic drugs. Only a few drugs have been used clinically to influence and modify the wound healing response following filtering surgery. Both steroidal and nonsteroidal anti-inflammatory drugs, which are inhibitors of the arachidonic acid pathway, limit fibroblast activity and reduce inflammation. Corticosteroids are routinely used after GFS to suppress the initial inflammatory response following surgical trauma. Corticosteroids applied in the early postoperative period have potential anti-fibroblastic potential effects. Corticosteroids inhibit synthesis of inflammatory mediators via the lipo-oxygenase and cyclo-oxygenase pathways by blocking the enzyme phospholipaseA2. This process reduces vascular permeability and chemotaxis and decreases granulocyte and mast cell degranulation and fibrin formation. 5-Fluorouracil (5-FU, an anti-metabolite drug) has been used during trabeculectomy to delay wound healing and, hence, to improve the success of surgery. As a pyrimidine analogue, it is metabolized into cytotoxic metabolites which in turn are incorporated into DNA and RNA, causing cell cycle arrest and apoptosis by inhibiting DNA-synthesis. 5-Fluorouracil acts selectively on the synthesis phase of the cell cycle (e.g., S-phase specific). Therefore, short exposure is sufficient to inhibit fibroblast proliferation. Mitomycin-C is another anti-metabolite wound healing agent that has been used to enhance the outcomes of GFS and it is used during trabeculectomy, like 5-Fluorouracil, but Mitomycin-C is not cell cycle dependent. Mitomycin-C selectively interrupts DNA replication and thus inhibits mitosis and protein synthesis. It has been shown to inhibit proliferation of cultured animal and human subconjunctival fibroblasts, but not to prevent fibroblast attachment or migration. Anti-fibroblastic and anti-metabolic drugs have shown effects in reducing IOP in eyes undergoing primary trabeculectomy, however, complications have limited their application in clinical GFS. Short term complications involve corneal epitheliopathy which recover well with time. Long time complications involve thin and cystic blebs, endophthalmitis, iridocyclitis, late bleb leaks, bleb encapsulation, cataract, prolonged hypotony, epitheliopathy and blebitis.

Transforming growth factor-β2 (TGF-β2) has been shown to be a potent stimulator of scarring in the eyes and it has been shown to be involved in the pathogenesis of cataracts, proliferative vitreoretinopathy, and conjunctival scarring. TGF-β2 is the most potent growth factor in the aqueous for stimulating conjunctival fibroblast function. Elevated levels of this isoform of TGF-βs are found in the aqueous of glaucomatous eyes compared with normal eyes (see Cordeiro et al., *Invest. Ophthalmol. Vis. Sci.* 40:2225-2234, 1999; Cordeiro et al., *Invest. Ophthalmol. Vis. Sci.* 40:1975-1982, 1999). These findings suggest that neutralizing the effects of TGF-β2 may reduce conjunctival scarring after GFS (Daniels et al, *Am. J. Pathol.* 163:2043-2052, 2003). Anti-TGF-β2 antibodies block TGF-β2 function to inhibit scar formation after GFS. For example, Lerdelimumab, a novel human monoclonal antibody that was isolated and developed in vitro by antibody phage display technology, exhibits high affinity and specificity for the active form of TGF-β and has been designed for therapeutic use (Mead et al., *Invest. Ophthalmol. Vis. Sci.* 44:3394-3401, 2003; Akhurst, *Curr. Opin. Investig. Drugs* 7:513-521, 2006).

To evaluate agent activity against ocular scarring, including for identification of new anti-scarring agents that inhibit proliferative scarring after, e.g., GFS, new, convenient animal models for ocular scarring are needed. In accordance with the methods described herein, any of various agents can be screened for activity against ocular scarring in teleosts such as, e.g., zebrafish. Such agents can, for example, include agents as discussed above as well as derivatives or analogs thereof, or other agents such as, e.g., agents from compound libraries (e.g., synthetic or recombinant peptide libraries, combinatorial compound libraries, and the like).

Analogous procedures can be used to test agents for activity useful in treating glaucoma in zebrafish having mutants associated with Glaucoma. Glaucoma represents a heterogeneous group of optic neuropathies, with different genetic bases. Glaucoma can be inherited as a mendelian autosomal-dominant or autosomal-recessive trait, or as a complex multifactorial trait. Three major types of glaucoma have been reported: primary open angle glaucoma (POAG), primary acute closed angle glaucoma (PACG) and primary congenital glaucoma (PCG), as well as a few others associated with developmental abnormalities. Defects in three genes—Myocilin, Optineurin and CYP1B1 result in Mendelian transmission of glaucoma. Single nucleotide polymorphisms in these and other genes associated with glaucoma provide useful models for analyzing glaucoma. With zebrafish, forward and reverse genetic approaches can be combined to identify critical genetic interactions required for normal and pathological events in the development and maintenance of the eye (McMahon, *Comp Biochem Physiol C. Toxicol Pharmacol* 138 (3): 343-50. (2004): Asch (1998), *J Neurochem* 71(1): 20-32; Kay (2001) *Neuron* 30(3): 725-36; Becker (2004) *Mol Cell Neurosci* 26(3): 376-89; Cheng, (2006) *Mech Dev* 123(3): 252-63). Vesicular transporters mediate the packaging of neurotransmitters into synaptic vesicles and can therefore control the amount of neurotransmitter released into the synaptic cleft. The mutation of a vesicular glutamate transporter found in the retinal ganglion cells (RGCs) of zebrafish alters both the synaptic transmission and connectivity between RGCs and their targets, limiting the transfer of visually evoked activity from RGCs and degrading behaviors that depend on high-acuity vision. Zebrafish with mutated or altered expression of the vesicular glutamate transporter provide models for study of glaucoma (Demas, et al. *Neuron* 53(1): 4-6. (2007); Smear (2007); *Neuron* 53(1): 65-77)).

3. Cataracts

Cataracts typically progress slowly to cause vision loss and are potentially blinding if untreated. A cataract is caused by development of an opacity in the crystalline lens of the eye or in its envelope which lies behind the iris and the pupil. Although the exact cause for cataracts is still unknown, cataracts is thought to develop from a variety of reasons, including long-term ultraviolet exposure, secondary effects of diseases such as diabetes, or simply due to advanced age. They are usually a result of denaturation of lens proteins. Genetic factors are often a cause of congenital cataracts and positive family history may also play a role in predisposing someone to cataracts at an earlier age, a phenomenon of "anticipation" in pre-senile cataracts. Physical injuries to the eye can also cause cataracts. During the early development of senile cataract, myopia (near-sightedness) is caused by the increased strength of the crystalline lens and the gradual yellowing and opacification of the lens and may reduce the perception of blue colors. Moreover, with time, the cataract cortex liquefies to form a milky white fluid in a Morgagnian Cataract, and can cause severe inflammation if the lens capsule breaks.

A number of zebrafish mutations are available to provide models for screening agents for activity useful in treating cataracts. Zebrafish with a cloche mutant, both the clochem39 and clocheS5 alleles, have defects in hematopoiesis and blood vessel development, provide a models system for study of lens cataracts. Quantitative examination of the living zebrafish lens by confocal microscopy shows significant increases in lens reflectance. Histological analysis reveals retention of lens fiber cell nuclei owing to impeded terminal differentiation. Proteomics identified γ-crystallin as a protein that was substantially diminished in cloche mutants. Crystallins are the major structural proteins in mouse, human and zebrafish lens. Defects in crystallins have previously been shown in mice and humans to contribute to cataracts. Overexpression of exogenous αA-crystallin can rescue the cloche lens phenotype, including solubilization of γ-crystallin, increased lens transparency and induction of lens fiber cell differentiation. Taken together, these results demonstrate that zebrafish with cloche mutants can be used as models of cataracts. Vihtelic, *Dev Dyn* 233(1): 52-65 (2005); Semina, (2006) *Dev Biol* 299(1): 63-77.

4. Other Zebrafish Mutants Associated with Ocular Disease (a) Ocular Syndromes

Mutant strains of zebrafish are available with unique deficits at various stages of the visual pathway, including lens degeneration (bumper), melanin deficiency (sandy), lack of ganglion cells (lakritz), ipsilateral misrouting of axons (belladonna), optic-nerve disorganization (grumpy and sleepy), inner nuclear layer or outer plexiform layer malfunction (noir, dropje, and possibly steifftier), and disruption of retinotectal impulse activity (macho and blumenkohl) (Neuhauss et al., (2003) *Doc Ophthalmol* 107(1): 71-8). Mutants with abnormally large or small eyes or severe wiring defects frequently exhibit no discernible behavioral deficits. Blind mutants that display outer-retina dystrophy, the single-most common cause of inherited blindness in zebrafish can also be readily obtained. A zebrafish fade out mutant provides a genetic model for studying hermansky-pudlak syndrome that is a group of autosomal recessive disorders characterized by oculocutaneous albinism and platelet storage pool deficiency with these disorders of retinal pigment epithelium of the eye Neuhauss, *J Neurosci* 19(19): 8603-15 (1999). Two recessive zebrafish mutants oval and elipsa that mutants share the syndromic phenotype of outer retinal dystrophy in conjunction with cystic renal disorder. These mutants may serve as accessible animal models of human outer retinal dystrophies, including oculo-renal diseases, and show the general usefulness of a behavioral genetic approach to study visual system development in the model vertebrate zebrafish (Bahadori (2003) *Eur J Neurosci* 18(6): 1377-86).

(b) Retinal Degenerative Diseases

A shrunken head (shr(m33)) mutation isolated as part of a large scale mutagenesis screen provides a model to study retinal cell death was studied in mutant zebrafish (*Danio rerio*) which undergo inherited degeneration of the retina. Goldsmith (2003), *Semin Cell Dev Biol* 14(1): 11-8. Behavioral screening for nightblindness mutants in zebrafish revealed three new loci that cause dominant photoreceptor cell degeneration and provide a model for this disorder (Maaswinkel (2005). *Mech Ageing Dev* 126(10): 1079-89)). Two zebrafish mutants, ebony and ivory, allow modeling of benefits of neighborhood on photoreceptor survival in retinal degenerative diseases (Goldsmith (2003a). *J Neurobiol* 57(3): 235-45); Kennedy, (2007) *Invest Ophthalmol Vis Sci* 48(2): 522-9)). The XOPS-mCFP transgene causes selective degeneration of rods without secondary loss of cones in animals up to 7 months of age (*Invest Ophthalmol Vis Sci* 46(12): 4762-71). Zebrafish with a red-blind mutant, partial optokinetic response b (pob), exhibit eye movements in response to rotating black and white stripes illuminated with white light, but do not move their eyes when the stripes are illuminated with red light providing a model for color blindness. Physiological, immunohistochemical, and in situ hybridization analyses of pob retinas showed a selective loss of red-sensitive cones at 5 days postfertilization (dpf) (Brockerhoff, et al. *J Neurosci* 17(11): 4236-42 (1997) Maaswinkel, *J Neurocytol* 32(9): 1107-16 (2003)).

(c) Eye Morphology and Visual Behavior

The mutation of thokh/rx3 or receptor protein-tyrosine phosphatase alpha knock-down in zebrafish causes loss of eyes (Loosli (2003) *EMBO Rep* 4(9): 894-9); Allwardt (2001) *J Neurocytol* 30(6): 493-501; Vihtelic (2002), *Vision Res* 42(4): 535-40; Neuhauss (1999), *J Neurosci* 19(19): 8603-15; Neuhauss, (2003) *Doc. Ophthalmol.* 107, 71-78)). Zebrafish possess three classes of chromatophores that include iridophores, melanophores, and xanthophores. Mutations that lack one or two classes of chromatophores have been isolated or genetically constructed. Using a behavioral assay based on visually mediated escape responses, the visual response of fully and partially pigmented zebrafish was measured. Screening pigments in the retina play a role in the regulation of behavioral visual responses and are necessary for avoiding "scatter" under bright light conditions. Also, inactivation of the zebrafish homologue of Chx10 by antisense oligonucleotides causes eye malformations similar to the ocular retardation phenotype (Barabino, *Mech Dev* 63(2): 133-43. (1997); Kainz, (2003), *J Comp Neurol* 463(3): 265-80).

(d) Ocular Motility Disorders

Zebrafish with a mutant termed belladonna serve as a behavioral model for congenital nystagmus caused by axonal misrouting. A large fraction of homozygous zebrafish mutant belladonna (bel) larvae display a reversed optokinetic response (OKR) that correlates with failure of the retinal ganglion cells to cross the midline and form the optic chiasm (Huang et al, *J Neurosci* 26(39): 9873-80. (2006)). The congenital fibrosis syndromes (CFS), including congenital fibrosis of the extraocular muscles (CFEOM) and Duane syndrome (DS), are rare congenital strabismus syndromes that present with nonprogressive restrictive ophthalmoplegia with or without ptosis. Although historically believed to result from primary extraocular muscle (EOM) fibrosis, these disorders result from distinct, but analogous, developmental defects of the oculomotor (nIII), trochlear (nIV), and abducens (nVI) nuclei. Three inherited CFEOM phenotypes (CFEOM1-3) and have mapped each phenotype to a distinct genetic locus (FEOM1-3). Individuals with CFEOM1 are born with bilateral ptosis and both eyes fixed in a downward position with absent upgaze and aberrant horizontal gaze. This disorder maps to the FEOM1 locus on chromosome 12cen. Neuropathology studies of CFEOM1 reveal the absence of the superior division of oculomotor nerve and its corresponding alpha motor neurons in the midbrain, with abnormalities of target EOMs. These neuropathology findings parallel those previously identified in Duane syndrome, in which there is an absence of nVI and the abducens nerve. Individuals with CFEOM2 are born with bilateral ptosis and exotropia. This atypical form of CFEOM maps to the FEOM2 locus on chromosome 11q13 and results from mutations in ARIX (PHOX2A).(6,7) ARIX encodes a homeodomain transcription factor protein previously shown to be required for nIII/nIV development in mouse and zebrafish. These findings support the hypothesis that the congenital fibrosis syndromes result from parallel defects in nIII, nIV, and nVI nuclear development. Zebrafish with mutations in the CFEOM genes can thus provide insight into the unique features of the extraocular lower motor neuron axis in health and disease (Baier, *Curr Opin Neurobiol* 10(4): 451-5 (2000); Engle (2002) *Ann N Y Acad Sci* 956: 55-63; Krauss et al. 2003: *Vision Res* 43(11): 1273-82)).

(e) Ocular Development

Ocular development involves modulated cellular proliferation in the optic vesicle, the complex spatiotemporal pattern of central retinal neurogenesis, the emergence of spatial order among the photoreceptors, the genetic controls of cell fates, and the genetic mechanisms underlying retinal stratification. Organogenesis results from a succession of complex processes including induction, patterning, specification, morphogenesis, and differentiation. Transcription factors including Pax6, Optx2, and Crx play important roles at different developmental stages of oculogenesis and are ultimately important in cell fate decisions. Mutations of these factors induce ocular developmental anomalies in humans, including aniridia, anophthalmia, and Leber congenital amaurosis (Easter, *Results Probl. Cell. Differ.* 40: 346-70 (2002); Malicki, *Vision Res* 42(4): 527-33 (2002)). The Egr1 gene plays an important role in zebrafish embryonic oculogenesis. Ocular structures including lens and retina were primitive and lacked appropriate differentiation. Such arrested retinal and lenticular development in Egr1 morphants resulted in microphthalmos (Hu, et al, *Mol Vis* 12: 1250-8 (2006)). The Pax6 genes of both vertebrates and invertebrates are expressed in the developing eye and in the central nervous system. These genes encode transcription factors with two DNA-binding domains, an N-terminal paired domain and a homeodomain separated by a flexible linker region. Ectopic eye structures are obtained upon targeted expression of Drosophila, squid, ascidian or mouse Pax6 genes in various imaginal disc primordia of Drosophila. Pax6 cDNA from zebrafish was cloned and the cloning of a novel Pax6 homolog from zebrafish denoted Pax6.2. The coding sequences of the two genes show 82% identity whereas the deduced amino acid sequences are 95% identical with complete conservation of the paired- and homeodomains. The embryonic expression patterns of Pax6.1 and Pax6.2 reveal both overlapping and discrete expression domains suggesting a division of labor between these two very similar gene products during development of brain and eye structures. Both Pax6.1 and Pax6.2 can act as transcriptional activators with Pax6.2 being more efficient than Pax6.1 (Nornes, et al, *Mech Dev* 77(2): 185-96 (1998)). Characterization of a chromosome 8q21.2-q22.1 segmental deletion in a patient with chorioretinal coloboma revealed elements of nonallelic homologous recombination and non-homologous end joining. This genomic architecture extends the range of chromosomal rearrangements associated with human disease and indicates that a broader spectrum of human chromosomal Tearrangements may use coupled homologous and nonhomologous mechanisms. The segmental deletion encompasses GDF6, encoding a member of the bone-morphogenetic protein family, and that inhibition of gdf6a in a model organism accurately recapitulates the proband's phenotype. The spectrum of disorders generated by morpholino inhibition and the more severe defects (microphthalmia and anophthalmia) observed at higher doses illustrate the key role of GDF6 in ocular development, which underscores the value of integrated clinical and molecular investigation of patients with chromosomal anomalies (Asai-Coakwell, et al. *Am J Hum Genet* 80(2): 306-15 (2007)).

(f) Visual System Development

Genetic analysis in zebrafish has been instrumental in identifying genes necessary for visual system development and function, Gross et al., *Genetics* 170(1): 245-61 (2005). A large-scale retroviral insertional mutagenesis screen, identified 315 different genes whose mutation resulted in obvious phenotypic defects by 5 days postfertilization was completed. Each of these mutants provides a model through which the formation, function, or physiology of individual organ systems can be studied. Forty of these mutants resulted in defects in eye development and/or visual function. The mutants have been divided into the following phenotypic classes that show defects in: (1) morphogenesis, (2) growth and central retinal development, (3) the peripheral marginal zone, (4) retinal lamination, (5) the photoreceptor cell layer, (6) the retinal pigment epithelium, (7) the lens, (8) retinal containment, and (9) behavior. The affected genes in these mutants highlight a diverse set of proteins necessary for the development, maintenance, and function of the vertebrate visual system, Gross et al. supra. Also zebrafish EK strain is a suitable in vivo vertebrate model system for analyzing the teratogenic effect of ethanol during vertebrate visual system morphogenesis as it relates to both cyclopia and fetal alcohol syndrome (Bilotta, *Neurotoxicol Teratol* 24(6): 759-66 (2002) Arenzana *Neurotoxicol Teratol* 28(3): 342-8 (2006) (Bilotta, *Neurotoxicol Teratol* 24(6): 759-66 (2002); Arenzana, *Neurotoxicol Teratol* 28(3): 342-8 (2006).

(g) Retinal Cell Development

Several molecules, such as growth factors and neurotrophic factors, are required both for the differentiation of specific retinal cell types and the long-term cell survival of all retinal neurons. As diffusible factors, these molecules act non-cell-autonomously. The loss of function phenotype for dazed (dzd), a gene that acts cell-autonomously for retinal cell survival and affects the differentiation of rod photoreceptors and the Muller glia. By 3 days after fertilization, dazed mutant embryos have small eyes and slight heart edema. Acridine orange staining indicated a significant degree of retinal cell death occurring by 48 hr after fertilization, and histological analysis revealed that dying cells were found in the inner and outer nuclear layers and near the marginal zones. Although molecular and morphological differentiation of the inner retina and cone photoreceptors occurred, rod photoreceptors failed to differentiate beyond a small patch in the ventral retina and rod precursors failed to respond to exogenously added retinoic acid, which normally potentiated rod differentiation. Mosaic analysis indicated that the dazed gene acts cell-autonomously for rod production and cell survival, as dazed clones failed to produce rods outside the ventral patch and dazed cells were not maintained in wild-type hosts. Raising mutants under constant light resulted in severe retinal degeneration, whereas raising embryos under constant darkness did not provide any additional protection from cell death. Behavioral analysis showed that a subpopulation of adult fish that were heterozygous for the dazed mutation had elevated visual thresholds and were night blind, suggesting that dazed may also be required for long-term dim-light vision. Taken together, these results suggest a role for the dazed gene in rod and Muller cell development and overall retinal cell survival and maintenance (Perkins, et al. *Dev Dyn* 233(2): 680-94 (2005)). The other report showed that, in a large scale screen for genetic defects in zebrafish embryogenesis, 49 mutations were identified affecting development of the retina (Malicki, et al. *Development* 123:263-73 (1996)). A genetic screen of mutant zebrafish was initiated to identify fish with abnormal visual responses but no obvious gross morphologic defects. The zebrafish visual mutant no optokinetic response c (nrc) is a possible model for human retinal disease. nrc has defects in photoreceptor synaptic transmission and light adaptation (Van Epps, et al. *Invest Ophthalmol Vis Sci* 42(3):868-74 (2001)). To facilitate the identification, and characterization of mutations affecting the retina and photoreceptors in the zebrafish, a transgene expressing green fluorescent protein (GFP) fused to the C-terminal 44 amino acids of *Xenopus rhodopsin* under the control of the 1.3-kb proximal *Xenopus opsin* promoter was inserted into the zebrafish genome. GFP expression was easily observed in a ventral patch of retinal cells at 4 days postfertilization (dpf). Between 45-50% of the progeny from the F1, F2, and F3 generations expressed the transgene, consistent with a single integration event following microinjection. Immunohistochemical analysis demonstrated that GFP is expressed exclusively in rod photoreceptors and not in the UV, blue, or red/green double cones. Furthermore, GFP is localized to the rod outer segments with little to no fluorescence in the rod inner segments, rod cell bodies, or rod synapse regions, indicating proper targeting and transport of the GFP fusion protein. Application of exogenous retinoic acid (RA) increased the number of GFP-expressing cells throughout the retina, and possibly the level of expressed rhodopsin. When bred to a zebrafish rod degeneration mutant, fewer GFP-expressing rods were seen in living mutants as compared to wild-type siblings. This transgenic line facilitates the search for recessive and dominant mutations affecting rod photoreceptor development and survival as well as proper rhodopsin expression, targeting, and transport and agents affecting any of these processes (Perkins, et al., *Vis Neurosci* 19(4): 257R-264R. (2002)).

(h) Ciliary Body

The forkhead C1 (FOXC1) transcription factor is involved in the development and regulation of several organs, including the eye, where FOXC1 alterations cause iris, trabecular meshwork and corneal anomalies. The fibroblast growth factor 19 (FGF19) locus is a gene potentially regulated by FOXC1. FGF19 is a direct target of FOXC1 in the eye. FOXC1 positively regulates FGF19 expression in corneal and periocular mesenchymal cells in cell culture and in zebrafish embryos. Through the FGFR4 tyrosine kinase, FGF19 promotes MAPK phosphorylation in the developing and mature cornea. During development, loss of either FOXC1 or FGF19 results in complementary, but distinct, anterior segment dysgeneses. This study reveals an important role for FOXC1 in the direct regulation of the FGF19-FGFR4-MAPK pathway to promote both the development and maintenance of anterior segment structures within the eye (Tamimi, et al., *Hum Mol Genet* 15(21: 3229-40. (2006)). Mutations in FOXC1 or FGF19 are thus useful in providing zebrafish models of ciliary body disorders.

B. Screening for Agent Activity in a Teleost Model of Ocular Disease

An agent can be screened for a desired ocular or ophthalmologic activity (e.g., a therapeutic or prophylactic activity) in an isolated eye, and/or an undesired activity (e.g., a cell death and/or toxic activity) in an isolated eye or other organ or tissue of the teleost. An agent is administered to a teleost in vivo. The teleost is typically a model for an ocular disease or disorder including any of the models described in the present application. An eye is isolated from the teleost, and a response in the eye is measured, indicating an activity.

Typically, the activity is a therapeutic or prophylactic activity against one or more symptoms of the ocular disease or disorder, or against one or more physiological correlates of the disease or disorder. For example, in the case of a teleost model for choroidal neovascularization (CNV), a phenotype observed in advanced age-related macular degeneration (AMD), the response to be measured can be, for example, the inhibition of abnormal blood vessel growth or angiogenesis, indicating, e.g., a therapeutic or prophylactic activity of the agent against an underlying pathology of AMD. In the case of a teleost model for a scarring process, such as that associated with, e.g., glaucoma filtration surgery (GFS), the response to be measured can be, for example, the inhibition of fibroblast activity (e.g., inhibition of fibroblast proliferation or collagen deposition), inhibition of inflammation (e.g., inhibition of inflammatory mediators or of leukocyte infiltration into the wound site), or inhibition of angiogenesis, indicating, e.g., an ability of the agent to modify the wound healing process.

Other activities for agents can also be screened in a teleost model of an ocular disease or disorder, including, for example, cell death and/or toxic activity. Such other activities can also be measured in an isolated eye, including, for example, simultaneously with measurement of an ocular or ophthalmologic activity in the eye. Alternatively, an agent can be screened for an activity (e.g., ocular or ophthalmologic) in the eye of a teleost model for an ocular disease or disorder as well as for a second activity (e.g., cell death and/or toxic activity) in at least one other organ or tissue of the teleost.

As discussed previously, an ocular disease or disorder can be mimicked in the teleost using a variety of tools available in the art, including, for example, available mutants, gene knockdown tools, and/or treatments (e.g., chemical phenocopies for a disease or disorder). In some embodiments, treatment with a compound is used to induce a disease phenotype (for example, in the case of teleost models for choroidal neovascularization, mimicking certain aspects of age-related macular degeneration, $CoCl_2$ treatment can be used to induce abnormal blood vessel growth and angiogenesis). An agent to be screened for an activity can be administered, e.g., before induction with a disease-condition-inducing compound (such as to test for the ability of the agent to prevent, delay, or decrease incidence of a disease condition in a teleost before disease-inducing conditions are present), or after induction with a disease-inducing-compound (such as to test for the ability of an agent to rescue the teleost from an established disease phenotype). Administration of an agent can also be performed simultaneously with a disease-condition-inducing compound. Similarly, when a surgical procedure is used to mimic a disease condition, administration of an agent be performed before, after, or contemporaneously with the surgical treatment.

III. Isolating Eyes

An eye can be isolated an any point during the development or treatment of the particular disease or disorder depending on the particular screening purpose. For example, when an effect of an ocular toxicant on an eye is to be evaluated, the eye can be isolated following exposure of the teleost to the ocular toxicant. When an agent is to be screened for a therapeutic or prophylactic activity against a disease condition in the teleost (e.g., screened for a protective effect against an ocular toxicant), the eye is isolated following treatment of the teleost with the potential therapeutic or prophylactic agent. Isolation of teleost eyes in accordance with the present invention is further described below.

A. Advantages of Using Isolated Eyes in Screening Assays

Currently, conventional methods of drug screening using small model organisms or tissue culture cells are performed in a high throughput format where intact live organisms (e.g., zebrafish embryos) or tissue culture cells are subjected to drug screening in multi-well plates. Screening, methods can be performed using a standard microplate well format, with a whole animal in each well of the microplate. This format allows screening assays to be automated using standard microplate procedures and microplate readers to detect enhancement or inhibition of biological activity in the whole animal in the wells. A microplate reader includes any device that can be facilitated to read a signal from a microplate (e.g., 96-well or 384-well plate, or the like), including fluorometry, luminometry, or photometry in either endpoint or kinetic assays. Using such techniques, the effect of a specific agent on a large number of small animals can be rapidly ascertained.

The conventional method of drug screening using a whole animal is, however, limited when one focuses on an activity specifically in the eye. In such a situation, the markers for targeting the activity often not only bind to a target in the eye but also other regions of the body. Thus, signals can emanate from other regions of the body as well as from other animals occupying in the same well. This approach results in a highly unspecific intensity. The conventional method of drug screening using an intact animal therefore entails laborious extra steps of normalizing the intensity of the activity detected by performing manual dissection of the eye from the intact body. Manual dissection of the eye can be time consuming, extremely difficult, and prone to cause physical damages to the sample. Thus, it is rate-limiting for the high throughput format, defeating the purpose of rapid screening. Furthermore, the conventional drug screen using tissue cultured cells is limited in that it provides no information regarding a potential drug's efficacy on the eye as a whole organ.

The use of isolated eyes provides certain advantages for screening an agent for an ocular activity. Such advantages include, for example, the ability to focus on the agent's activity in the eye without interference from other organs or tissues, as well as greater sensitivity and/or specificity of readouts of experimental assays when the eye is separated from the remaining organs and tissues of the animal. Another advantage is that the use of isolated eyes facilitates analysis of the back of the eye, which is not easily visualized in an intact teleost, even in transparent embryonic or larval forms. Visualization of the back of the eye is particularly important with respect to several eye diseases, including, for example, choroidal neovascularization in advanced age-related macular degeneration (AMD) and diabetic retinopathy (DR), two of the most common and poorly treated back-of-the-eye diseases.

B. Isolating Eyes from Teleosts

In accordance with the present methods, an intact eye is removed from a teleost. In certain embodiments, eyes are removed by contacting the teleost with an enzyme that is capable of dissociating the eye from an intact body of the teleost, thereby facilitating separation of the eye from the intact body of the teleost, and collecting the separated eye. The use of enzymatic treatment for isolating intact eyes has various advantages over conventional, surgical approaches for isolating intact eyes. For example, enzymatic treatment can dissociate eyes from an intact body of a teleost (e.g., a zebrafish) without laborious manual dissection and/or deleterious effects on the isolated eyes Enzymatic treatment for isolating intact eyes as described herein is also amenable to a multi-well (e.g., microtiter) format (see Section V, infra).

Particularly suitable enzymes for use in accordance with the present invention include, for example, various collagenases, which degrade collagen-containing connective tissues and can be used in the methods described herein to isolate intact eyes from vertebrate organisms. Collagenases cleave helical collagen fibrils, major components of extracellular connective tissues such as blood vessel, bone, tendon, skin (for review, see Harper, *Annu. Rev. Biochem.* 49:1063-1078, 1980). True collagenase may simultaneously cleave across all three chains of the triple-helical structure or attack a single strand. Mammalian collagenases cleave collagen in its native triple-helical conformation at a specific site giving rise to 2 fragments representing ¾ and ¼ lengths of the tropocollagen molecule (see Woolley et al., *Eur. J. Biochem.* 54:611-622, 1975; Gross et al., *Biochem, Biophys, Res. Commun.* 61:605-612, 1974). After fragmentation, the pieces tend to uncoil into random coil polypeptides, known as gelatin.

Collagenases from mammalian sources have been previously reported. (See, e.g., Bauer et al., *Biochem. Biophys. Res. Commun.* 64:232-240, 1975; Brady, *J. Clin. Invest,* 56:1175-1180, 1975; Huang and Abramson, *Biochim, Biophys. Acta* 384:484-492, 1975; Sakamoto et al., *Biochem. Biophys. Res. Commun.* 63:172-178, 1975; Wahl et al., *Science* 187:261-263, 1975; Wooley et al., *Eur. J. Biochem.* 50:437-444, 1975; Fujiwara et al., *Biochem. Biophys. Res. Commun.* 60:166-171, 1974; Gross et al., *Biochem. Biophys. Res. Commun.* 61:605-612, 1974; Werb and Burleigh, *Biochem. J.* 137:373-385, 1974; Woessner and Ryan, *Biochim. Biophys. Acta* 309:397-405, 1973; Tokoro et al., *Biochim. Biophys. Acta* 258:289-302, 1972; Vaes, *Biochem. J.* 126: 275-289, 1972; Donoff et al., *Biochem. Biophys. Acta* 227: 639-653, 1971; Eisen et al., *Proc. Natl. Acad. Sci. USA* 68:248-251, 1971.

Bacterial collagenases usually purified from invasive strains bacteria are also employed to isolate cells from a tissue or tissues from an organ. Bacterial enzymes differ from mammalian collagenases in that they cleave many sites along the helix (Seifter and Harper, 1971). Particular enzymatic activities of bacterial collagenases have correlated with the tissues from which the cells were obtained (or with the uses to which the cells are put), and as a result of the correlations several formal types have been established. Bacterial collagenase Type I, which contains average amounts of assayed activities (collagenase, caseinase, clostripain, and tryptic activities), is generally recommended for fat, adrenal, and liver cells. Collagenase Type II, which contains greater clostripain activity, is generally used for heart, bone, muscle, thyroid, cartilage, and liver cells. Collagenase Type III, which contains low proteolytic activity, is usually used for mammary and fetal cells. Collangenase Type IV, which contains low tryptic activity, is commonly used for islets and other applications where receptor integrity is crucial.

Bacterial collagenase has been used to isolate pancreatic islet cells for the experimental transplantation of islet cells to alleviate diabetic symptoms (Barker, 1975). Intact parenchymal cells from rat liver tissue have also been isolated (Seglen, 1973; Berry and Friend, 1969; Howard et al., 1967). Kitabchi et al. (1971) isolated rat adrenal cells and Czech and Fain (1971) isolated fat cells. DeOca and Malinin (1975) reported on the isolation of primary cell cultures from human kidney.

U.S. Pat. No. 6,238,922 discusses a method for using collagenase to dissociate neural stem cells from neural stem cell cultures where collagenase treatment results in an increased cell viability and an increased number of proliferated neural stem cells over time. U.S. Pat. No. 6,946,293 discusses methods for isolating a substantially pure population of viable pancreatic progenitor cells. U.S. Pat. No. 6,376,244 discusses methods for producing a decellularized organ or part of an organ using collagenase. U.S. Pat. No. 7,045,349 discusses an islet separation technology which incorporates an automated method, automated control methodology, process control interface, and automated apparatus to isolate pancreatic islets in a tissue suspension in physiologic process solution. U.S. Pat. No. 5,952,215 discusses an enzyme composition (purified collagenase and an endoprotease) and its use for isolating cells or cell clusters from tissues. U.S. Pat. No. 6,815,203 discusses methods of promoting dedifferentiation of pancreatic cells, methods of obtaining pancreatic islet cells from the dedifferentiated pancreatic cells, and methods of treating a subject having a disorder characterized by insufficient pancreatic islet function by administering pancreatic islet cells obtained by these methods.

The conventional collagenase usage, however, focuses on isolation of cells or tissues from organs. In the present methods, a collagenase or other suitable enzyme capable of dissociating an eye from a teleost is used to isolate an intact organ, namely, an intact eye, from animals. Suitable enzymes besides collagenases that can be used in the methods of the invention include, for example, dispase, trypsin, chymotrypsin, and hyaluronidase.

For removing intact eyes, enzyme concentration, treatment time, and temperature can be optimized as needed. Such parameters can vary according to any particular usage. For example, suitable enzyme concentrations can vary according to treatment times and/or incubation temperature, and vice versa (e.g., lower concentrations of enzyme and/or lower incubation temperatures can be used with longer incubations times and vice versa). Particularly suitable concentrations of collagenase typically range from between about 15 U/ml and 150 U/ml. Enzyme incubation temperature is typically between room temperature and about 37° C. Lower concentrations of enzyme or lower temperatures result in slower enzymatic reaction time. Thus, for removing intact eyes, enzyme concentration, treatment time, and temperature can be optimized according to the need and particular usage.

For example, using relatively higher enzyme concentrations (e.g., about 75 U/ml to about 150 U/ml), treatment times at 37° C. are typically between about 15 minutes and about 4 hours, more typically between about 30 minutes and about 2 hours. In a specific embodiment, collagenase is used at a concentration of 150 U/ml for 45 minutes at 37° C. In some alternative embodiments, using relatively lower enzyme concentrations (e.g., about 15 U/ml), treatment times at 37° C. are typically greater than about 4 hours.

Incubation periods greater than about 4 hours are also usually required when using incubation temperatures less than 37° C. Generally, incubation periods and temperature can be varied between about 4 hours and about 16 hours and between room temperature and about 36° C. For example, in one specific variation, teleosts are treated with 15 U/ml collagenase at 32° C. for 10 hours. In other embodiments, room temperature treatment with collagenase is performed using an enzyme concentration of 15 U/ml or greater at an incubation period of about 16 hours or less (e.g., at 15 U/ml for 16 hours, or at 50 U/ml for 10-12 hours); typically, at enzyme concentrations of greater than 15 U/ml, the duration of incubation at room temperature is shorter than 16 hours. Preferably, with room temperature treatments, relatively higher enzyme concentrations are used (greater than about 15 U/ml such as, e.g., between about 50 U/ml and about 150 U/ml, or between about 75 U/ml and about 150 U/ml) at relatively longer incubation periods (e.g., between about 4 hours and about 12 hours, or between about 4 hours and about 10 hours).

Enzymatic treatment of a teleost in accordance with the present methods dissociates intact eyes from other organs and tissues of the teleost. Dissociation of intact eyes from the teleost body can be further facilitated by, e.g., gentle pipetting. In certain embodiments, the teleost body is substantially digested by the enzymatic treatment, such that portions of the teleost other than the eye do not remain substantially intact. One particularly suitable enzyme for use in digesting the teleost body while leaving a dissociated eye intact include is dispase. For example, 60 U/ml collagenase and 2 U/ml dispase can be used to treat the zebrafish for about 2 hours at 37° C. In such a condition, the eyes can be dissociated from the body, but the teleost body does not remain completely intact. In alternative variations, the teleost remains substantially intact following removal of the eyes, thereby allowing for subsequent analysis of responses or activities in other organs and tissues of the teleost. In some embodiments for obtaining both a dissociated eye and a body that are substantially intact, collagenase is used in the absence of a second enzyme that promote digestion of the teleost body (e.g., in the absence of dispase). For example, collagenase can be used as generally described above (e.g., at concentrations between about 15 U/ml and about 150 U/ml; temperatures between room temperature and 37° C.; at incubation periods ranging from 15 minutes to overnight), but in the absence of dispase or other enzyme that promotes digestion of the teleost body. In one specific variation for obtaining both a dissociated eye and a substantially intact body, 150 U/ml collagenase is used for 45 minutes at 37° C. in the absence of dispase.

Once dissociated from an intact body of a vertebrate by enzymatic treatment, the dissociated eye(s) can be collected by, for example, filtration or density gradient centrifugation. In certain embodiments, after treatment of one or more vertebrates with an appropriate enzyme for dissociating eyes, resulting in a pool of eyes, cellular debris, and other vertebrate-body-derived components, a sample of isolated eyes can be obtained from the pool by a density centrifugation, a common technique routinely employed to separate particles in a dense solution or density gradient based on the individual densities or mass over size ratios. For example, a solution (e.g., sucrose) can be prepared such that a gradient of densities is available for particles to pass through or float upon. A density gradient may be continuous or prepared in a stepped manner. In accordance with the present invention, differential centrifugation can also be employed to obtain pure eye samples from other cellular debris or potential contaminants (e.g., enzyme used for dissociating eyes).

In other variations, as noted above, a filtration method is used to isolate one or more dissociated eye(s) from cellular debris or other contaminants following enzymatic treatment. Filtration is an efficient method for the separation of an isolated eye from a mixture comprising the eye and the remaining body and/or large debris after the eye has dissociated from the body. The size of the eye of an adult zebrafish is typically less than 200 μm in diameter. Thus, a net filter of the size between, e.g., about 300 to about 400 μm can be suitable for filtering out the body and larger debris while allowing the eyes to flow through. Typically, nylon filters are compatible with a broad range of solvents. Woven net filters with mesh openings ranging from about 200 to about 400 μm are commercially available (Millipore Corp., MA; Fish Farm Supply Co., On, Canada). The filtration can be achieved by using gravity filter (open system that operates with water column pressure only) with occasional shaking A closed system that operates under pressure (positive pressure or vacuum) can be also employed.

Following separation of an eye from a teleost, the isolated eye can be evaluated for any biological parameter as desired (e.g., evaluated for a physiological, cellular, or biochemical process). For example, in accordance with certain aspects of the present invention, the isolated can be evaluated for the presence or absence of a response to an agent that has been administered to the teleost from which the eye was isolated, as described further herein. The isolated eye can be further processed in accordance with the particular detection method to be used for measuring a response or activity.

For example, the isolated eye can be transferred to a well of a multi-well plate (e.g., a microtiter well of a microtiter plate). Placement of a plurality of isolated eyes in multi-well plates is useful for, e.g., high-throughput screening of agents and is further amenable to various image analysis techniques, such as, e.g., techniques noted in Section I(E), supra. For example, microliter plates are particularly useful in conjunction with detection methods such as, e.g., fluorometry, luminometry, or photometry. Multi-well plates can also be used, for example, in conjunction with a variety of microscopic methods.

Alternatively, an isolated eye is placed on a slide (e.g., a glass slide), which is also useful for various image analysis techniques, particularly microscopic techniques such as, for example, those discussed in Section I(E), supra. For example, an isolated eye placed on a glass slide can be analyzed by, e.g., epifluorescence microscopy, confocal microscopy, and digital interference contrast (DIC) microscopy, to name a few. Placement of isolated eyes on slides is also amenable to, e.g., in situ hybridization for detection of mRNA.

Isolated eyes can also be analyzed in suspension. For example, isolated eyes suspended in a solution can be analyzed using a flow cytometer such as, e.g., those commercially available from Becton Dickenson or Beckman-Coulter. Isolated eyes in suspension can also be analyzed using a large particle dispenser (Union Biometrica, Holliston, Mass.). The use of a flow cytometer or large particle dispenser is particularly amenable to measurement of a response or activity in a single eye. COPAS™ BioSorter™ instruments provide flow cytometry for objects that are too large for traditional cytometers (e.g., the isolated teleost eyes). These systems sort and dispense objects based on size and fluorescent parameters, allowing sorting of large particles sized from 10 to 1,500 microns. In certain embodiments, a flow cytometer or large particle dispenser is used to measure a response or activity separately in each of a plurality of isolated eyes.

IV. Screening Agents for Ocular Activity and Cell Death and/or Toxic Activity in Zebrafish The methods for screening agents for ocular or ophthalmologic activity can be combined with other methods of the present invention described below, including methods of screening agents for an effect on cell death activity (e.g., apoptosis or necrosis) and/or toxic activity. Because the teleosts used with these methods are transparent, it is possible to assess ocular or ophthalmologic activity in conjunction with cell death activity and/or toxic activity. Responses indicating various activities can also be detected in conjunction with one another, either at separate times or simultaneously.

Such combined methods are useful in assessing multiple affects of an agent on a teleost. The agent may cause both a desired response, such as enhancement or inhibition of an ocular activity, and a toxic (undesired) response. The ability to assess multiple activities and responses in a teleost due to the administration of an agent is of particular benefit in identifying potential therapeutic compounds and assessing their side effects. For example, one difficulty associated with identifying compounds that can be used as therapeutics in treatment of an eye disease or disorder is that some compounds may also have deleterious effects on extra-ocular tissues or organs. A combination screen for assessing ocular activity and cell death activity and/or toxic activity of an agent would be useful in identifying those agents that are useful for treating eye diseases or disorders, but that induce apoptosis or necrosis, or are toxic, elsewhere. Dose levels of the agent effective to promote a particular ocular activity without promoting cell death activity and/or toxic activity can be ascertained.

Multiple activities/responses can be monitored in the whole teleost or in one or more tissues or organs of the teleost. Such activities and responses can be monitored over time and at predetermined time intervals. A variety of techniques can be used together or separately to analyze multiple activities and responses, including, e.g., fluorescence microscopy, light microscopy, digital image analyzing, standard microplate reader techniques (colorimetry, fluorometry, including time-resolved fluorometry, and chemiluminescence), in situ hybridization, antibody staining of specific proteins, changes in protein distribution temporally and spatially within the animal, changes in a level of enzymatic activity in the whole teleost, or tissues, organs or cells of the teleost. Furthermore, the response can be discriminated and/or analyzed by using pattern recognition software.

In one aspect, the invention provides a method of screening an agent for an increase or decrease in an ocular or ophthalmologic activity as described above and further including screening the agent for an ability to enhance or inhibit cell death activity by detecting a response in the teleost indicating an enhancement or inhibition of cell death activity. The cell death activity can be detected in the eye of the teleost or in at least one other tissue or organ of the teleost. Such methods are useful, e.g., in identifying contra indications to therapeutic or prophylactic value of a compound.

In one aspect, the present invention provides a method of screening an agent for an increase or decrease in an ocular or ophthalmologic activity as described above and further including screening the agent for an increase or decrease in toxicity by detecting a response in the teleost indicating an increase or decrease in toxic activity. The toxic activity can be detected in the eye of the teleost or in at least one other tissue or organ of the teleost. Such methods are useful, e.g., in identifying contra indications to therapeutic or prophylactic value of a compound.

Methods to screen agents for cell death activity and/or toxic activity in conjunction with screening the agents for angiogenesis activity in vivo in a teleost, e.g., zebrafish, have been described. See U.S. Pat. Nos. 6,299,858 and 6,656,449, the disclosures of which are incorporated herein in their entirety for all purposes. The same or similar methods can be used in accordance with the present invention to screen agents for an ocular or ophthalmologic activity and for cell death activity and/or toxic activity in the same teleost in vivo. Particularly suitable methods of screening for cell death and/or toxic activity in a teleost, and which can be used with the present invention, are summarized below.

A. Methods of Screening Agents for Cell Death Activity

Cell death activity is the ability or capacity of an agent to enhance, stimulate, inhibit, or block cell death in an animal, tissue, organ, or cell in response to administration of an agent. Cell death activity is assessed relative to contemporaneous and/or historical control teleosts (or tissues, organs, or cells thereof) to which the agent has not been administered. Such methods are useful for, e.g., screening an agent for its ability to trigger, enhance, suppress, or eliminate an apoptotic or necrotic process, particularly an agent that has been or is being screened for activity in an eye such as in accordance with the methods provided herein.

Some such methods comprise administering the agent to a whole teleost in vivo and detecting a response in the teleost indicating an effect on cell death activity. In some such methods, the detected response is an increase or initiation of cell death activity. In other methods, the detected response is a decrease or suppression of cell death activity. In some methods, the response is an increase or decrease in apoptotic activity. An effect on apoptotic activity can be measured by detecting a response indicating such an effect; the response can be, for example, an increase or triggering of apoptosis or a decrease or suppression of apoptosis. An increase in apoptotic activity generally comprises an increase in the death of cells in a tissue or organ of the animal. In other embodiments, the response is an increase or decrease in necrotic activity.

The effect of a particular agent on the entire, intact teleost and/or one or more organs, tissues, or systems of the teleost (e.g., the cardiovascular system, the enteric system, and the musculature) can be measured in vivo and, if desired, over a period of time and/or at selected time intervals. Responses in combinations of organs and/or tissues can be detected simultaneously or separately; such analyses can be performed over time at predetermined time intervals.

Cell death activity can be detected in vivo by using at least one of a variety of techniques, including, e.g., fluorescence microscopy, light microscopy, digital image analyzing, or standard microplate reader techniques (colorimetry, fluorometry, including time-resolved fluorometry, and chemiluminescence), antibody staining of proteins, changes in enzyme levels or enzymatic activities in the whole teleost, or tissues, organs or cells of the teleost, and changes in protein distribution temporally and spatially within the animal. The response can also be discriminated and/or analyzed by using pattern recognition software. Thus, for example, an increase in apoptotic or necrotic tissue can be analyzed in a zebrafish by using such techniques.

Fluorescence-based detection techniques and fluorescence microscopy can also be used to detect the effect of an agent on cell death activity in an animal, such as a teleost. For example, teleosts can be stained with a membrane-impermeant, nuclear-staining fluorescent dye which permits detection of cell death activity. A variety of fluorescent dyes can be used. Preferred dyes include those of the unsymmetrical cyanine dye family (such as quinolium dyes, e.g., benzothiazolium-4-quinolium dyes (Molecular Probes)), including derivatives, analogs, and substituted or unsubstituted forms thereof. Such dyes are generally discussed in U.S. Pat. No. 5,658,751, which is incorporated herein by reference in its entirety for all purposes. A number of these dyes are commercially available.

These dyes, including monomeric cyanine dyes (such as benzothiazolium-4-quinolium), cannot pass through intact membranes of cells of live embryos. However, these dyes can enter dead or dying cells whose membranes have become discontinuous or disrupted (a characteristic of cells undergoing cell death, see, e.g., Liepins and Bustamante, supra). Notably, the cytoplasmic blebbing and other properties in the membrane characteristic of a dead, dying cell, or apoptotic cell permit such dyes to enter the cell.

Upon passing through the cell membrane, monomeric cyanine dyes (e.g., benzothiazolium-4-quinolium) intercalate into the DNA of the dead or dying cells. The dense chromatin and nuclear fragmentation provide an ideal environment for dye intercalation and signal amplification (see. Singer, *Biotechnol. Intl.* 1:267-276, 1997). Upon intercalating into the DNA, the dye becomes intensely fluorescent, allowing for rapid detection of the labeled cells using simple fluorescence microscopy. Notably, when concentrated in DNA, the fluorescent signal of benzothiazolium-4-quinolium dye is amplified up to 400 fold (see Serbedzija et al., *J. Neurobiol.* 31:275-282, 1996). The magnitude of the signal serves as a measure of the number of apoptotic or necrotic cells.

Notably, the in vivo methods of screening agents for cell death activity of the present invention provide a more sensitive and accurate detection and measurement of cell death in whole embryos in vivo than permitted by existing approaches. Other fluorescent markers of cell death, such as Acridine Orange, pass through the membranes of cells of live embryos much more readily and fluoresce under a variety of conditions than do monomeric cyanine dyes, such as benzothiazolium-4-quinolium dyes. For example, Acridine Orange fluoresces when bound to nucleic acids and when localized in subcellular compartments such as lysozymes.

Monomeric cyanine dyes (e.g., benzothiazolium-4-quinolium dyes) also provide a higher signal-to-background when bound to nucleic acid. The characteristic emission spectra of monomeric cyanine dyes permit the use of two or more additional fluorescence labels simultaneously in conjunction with the quinolium dye, thereby allowing characterization of multiple types of physiological events within the same or different organs or tissues. Thus, with the methods of the invention described herein, more than one fluorescent dye can be used together for monitoring multiple cellular and/or molecular phenomena in response to an agent administered to the animal in vivo simultaneously over time. Dyes can be selected to have emission bands that match commercially available filter sets such as that for fluorescein or for detecting multiple fluorophores with several excitation and emission bands.

Furthermore, benzothiazolium-4-quinolium dyes are not toxic; thus, apoptotic or necrotic effects in a living teleost to which the dye has been administered can be monitored over a significant time period, without risk that the teleost will be adversely affected by the dye.

The fluorescent dye is typically administered to the teleost by adding the dye to the media containing the teleost. Alternatively, the dye can be injected directly into the teleost. The dye is typically administered prior to administration of the agent to be screened for cell death activity. This procedure provides superior results over existing approaches, because if the dye is added after apoptosis has been induced, the dye is less effective in labeling dead or dying cells. One of the apoptotic mechanisms (e.g., the polymerization of components of intracellular membranes and the plasma membrane) may make it difficult or impossible for the dye to enter the cell. As a result, an apoptosing cell may not be labeled. By applying the dye prior to application of the agent, this problem is avoided. The fluorescence emission of the dyes is monitored by using standard fluorometric techniques, including visual inspection, CCD cameras, video cameras, photographic film, or the use of current instrumentation, such as laser scanning devices, fluorometers, photodiodes, quantum counters, photon counters, plate readers, epifluorescence microscopes, scanning microscopes, confocal microscopes, or by means for amplifying the signal, such as a photomultiplier tube.

Unlike other known dyes which involve laborious labeling procedures (e.g., TUNEL labeling), the benzothiazolium-4-quinolium dyes are particularly suitable for high throughput, automated screening methods. The higher signal-to-noise ratio inherent in these dyes and our superior method of administering the dye prior to administration of the agent to be screened for apoptosis enable automated data acquisition, more accurate quantitation of the collected data (e.g., digital imaging), and the possibility of feature extraction/image segmentation of acquired data. These features allow mapping of the apoptosis signal in space/time dimensions that can be correlated with fate map coordinates of the specific teleost's fate map. Such information permits further characterization of the screened agents.

As noted above, cell death activity can also be detected by digital imaging. Digital imaging is an indispensable tool for biological research due to several advantages when compared to the human eye. Digital imaging involves the collection of images using a charge-coupled device (CCD). The higher sensitivity imaging detector enables one to visualize very low light objects which are not detectable by the unaided human eye. The spectrum sensitivity of the human eye is limited from 400 to 700 nm. In contrast, the spectrum sensitivity range of imaging detectors is more broad, and signals from the range of x-ray to infrared can be detected. Combining digital mapping and pattern recognition software enables the quantification and comparison of multiple data sets and facilitates comparison of contemporaneous and historical controls with experimental teleost animals.

The present invention also provides methods of screening a compound for its effect on cell death activity in vivo in a teleost over time. Such methods comprise administering the compound to the teleost in vivo, detecting a response in the teleost indicating an effect on cell death activity, and further detecting a response in cell death activity in the teleost after a predetermined period of time or time interval. The period of time, which is selected by the practitioner, is typically sufficient for detectable cell death to occur in the presence of the compound. In addition, multiple time points can be examined to detect any pertinent physiological activity. Some such methods further comprise detecting a response in cell death activity after a second predetermined time interval using the detection techniques described herein. Such methods are useful in evaluating the effect of an agent (e.g., chemical compound, drug, environmental agent, agricultural compound, toxin, pharmaceutical, cosmeceutical) on tissues and organs over time in the intact, live teleost.

In yet another aspect, the present invention provides methods of screening an agent for an effect on cell death activity in vivo, as described above, and further including detecting an increase or decrease in cell death activity in more than one tissue or organ of the teleost simultaneously. In some such methods, the increase or decrease in cell death activity is detected simultaneously in more than one tissue or organ at predetermined time intervals. The effect of a particular compound on various cells, tissues, and organs of the embryo can be monitored and assessed over time. Cell death activity in multiple tissues or organs can be detected by using the detection techniques described throughout this specification.

The present invention also provides automated methods of screening a compound for an effect on cell death activity in vivo. The methods of the invention can be performed using a standard microplate well format, with one or more whole teleosts per well of the microplate. This format permits screening assays to be automated using standard microplate procedures and plate readers to detect cell death in the zebrafish in the wells. With this setup, the effect of a specific compound on a large number of teleosts can be ascertained rapidly. In addition, with such format, a wide variety of compounds can be rapidly and efficiently screened for their respective effects on the cells of teleosts (e.g., teleost embryos) contained in the wells. Both sample handling and detection procedures can be automated using commercially available instrumentation and software systems for rapid reproducible application of dyes and compounds and automated screening of target compounds.

The present invention includes screening methods which rely on detecting enzymatic activity associated with apoptosis. In one aspect, the invention provides methods of screening an agent for apoptotic activity which comprise administering the agent to a teleost and detecting a response in the teleost indicating apoptotic activity by detecting the activity of an enzyme (e.g., cleavage of caspase substrate).

Caspase enzymes, for example, are well characterized proteases that function as triggers, effectors, or mediators in a number of apoptotic pathways. The fluorogenic caspase substrate can be introduced to the teleost by a variety of methods, including, e.g., by injection into the teleost, by dissolving the substrate in the medium containing the teleost. The manner of introduction of the substrate depends upon the particular type and nature of reporter substrate design (e.g., small molecule, plasmid). The fluorogenic caspase substrate can be introduced at the time or, after, or, usually, prior to administration of the agent. Caspase activity (e.g., cleavage of caspase substrate) can be measured by using, for example, commercially available colorimetric or fluorometric enzymatic assays or by using antibodies which detect cleaved substrates (e.g., M30 CytoDEATH antibody; Boehringer Mannheim). Specific patterns of embryo dysgenesis result from the inhibition of naturally occurring apoptotic events during development. Inhibition of caspase activity can cause specific morphological effects including tissue malformation. Such methods can be conducted in vivo using whole teleosts or in vitro using cells of the teleost. Such methods are useful for identifying agents having apoptotic activity that may have potential therapeutic or prophylactic use for treating a variety of diseases, such as cancer.

Examples of methods of screening an agent for effects on cell death activity in conjunction with screening the agent for effects on other activities (e.g., angiogenesis activity and/or toxic activity) simultaneously in a teleost in vivo are described in U.S. Pat. Nos. 6,299,858 and 6,656,449, the disclosures of which are incorporated herein in their entirety for all purposes.

B. Toxic Activity Screening Methods

Toxic activity can be assessed relative to contemporaneous and/or historical control teleosts (or teleost tissues, organs, or cells) to which the agent has not been administered. Such methods generally comprise administering the agent to a teleost and detecting a response in the teleost indicating the activity. These methods are useful for, e.g., rapidly, comprehensively, and reproducibly screening for and predicting toxic responses, including harmful and lethal effects on developing organs and tissues in whole teleosts, due to one or more agents, particularly agents that have been or are being screened for activity in an eye such as in accordance with the methods provided herein.

The zebrafish is among the preferred teleosts for these methods. As outlined in detail above, zebrafish offer a number of advantages for toxicity testing, including that zebrafish are transparent (thus facilitating observation and analysis of multiple tissues and organs simultaneously), develop rapidly, are easy and inexpensive to generate and maintain, and amenable to high throughput toxicity screens. In addition, the morphological and molecular bases of tissue and organ development are generally either identical or similar to other vertebrates, including man, and thus toxicity screens of compounds in zebrafish provide relevant information about the effect of compounds in humans. Moreover, we have determined that teleosts exhibit dose-responsiveness to toxicity and thus zebrafish and the toxicity screening methods described herein are useful in determining the effects of particular doses of agents on particular organ and tissue systems and the sensitivity of particular organs and tissues to such doses.

As described above, the compound to be screened can be administered to the teleost by diffusion simply adding it to the media containing the teleost or by microinjection or similar techniques.

The present invention includes in vivo methods for screening agents for a toxic effect or activity on one or more organs (e.g., the kidney, pancreas, cardiovascular system, central nervous system, intestine, liver) or tissues simultaneously or independently. All such methods can be used to screen a wide range of agents and compounds, including, among other things, chemical compounds, pharmaceuticals, therapeutics, environmental and agricultural agents, industrial agents, pollutants, cosmeceuticals, synthetic or natural compounds, drugs, organic compounds, lipids, glucocorticoids, peptides, antibiotics, chimeric molecules, sugars, carbohydrates. These agents and compounds can be screened singly or as mixtures, including complex mixtures.

Toxic effects and activity resulting from administration of a compound to an animal (e.g., teleost) can be indicated by a variety of responses in the animal, including, but not limited to, e.g., molecular changes, genetic mutations, developmental defects, developmental delay, genotoxicity, reproductive toxicity, organ toxicity or dysgenesis, behavioral toxicity, teratogenicity, death of the animal) Responses indicating toxic activity can be detected in the whole teleost or in at least one tissue or organ of the teleost. The response can be detected in multiple tissues and organs simultaneously or separately over time at predetermined time intervals. For example, the response can be detected in at least two different tissues, at least two different organs, or in at least one organ and at least one tissue.

A variety of techniques can be used together or separately to generate a signal (e.g., in situ hybridization, antibody staining of specific proteins) and to detect and assess responses (e.g., colorimetry, fluorescence microscopy, light microscopy, digital image analyzing, standard microplate reader techniques, fluorometry, including time-resolved fluorometry, and chemiluminescence, visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube.

The methods for screening agents for toxic activity described herein can be combined with other methods of the present invention, including methods of screening agents for an ocular activity (see Section II) and cell death activity (see supra). As noted previously, with transparent teleosts, it is possible to assess such multiple activities and the responses resulting from such activities in the whole teleost or in one or more tissues or organs simultaneously and at predetermined time intervals. Assays combining toxicity screening with screening for cell death activity are useful as discussed previously for identifying deleterious and lethal responses resulting from agent administration, proper dosage amounts, and in developing effective therapeutics and treatment programs.

A variety of techniques can be used together or separately to analyze multiple activities and responses, including fluorescence microscopy, light microscopy, digital image analyzing, standard microplate reader techniques (colorimetry, fluorometry, including time-resolved fluorometry, and chemiluminescence), in situ hybridization, antibody staining of specific proteins, enzymatic changes, changes in protein distribution temporally and spatially in the teleost.

In another aspect, the present invention provides a method of screening an agent for a toxic activity as described above and further including screening the agent for an effect on cell death activity by detecting a response in the teleost indicating an effect on cell death activity (as discussed supra). Tissue and organ specific patterns of cell death can be evaluated in addition to examining various markers to analyze organ toxicity. Cells undergoing cell death can be identified by a variety of means, including those discussed above (e.g., using a membrane-impermeant, nuclear-staining dye from the benzothiazolium-4-quinolium dye family, the TUNEL assay, or colorimetric or fluorometric enzymatic assay of caspase activity).

In yet another aspect, the invention provides a method of screening an agent for a toxic activity as described above and further including screening the agent for an increase or decrease in ocular activity by detecting a response in the teleost indicating an increase or decrease, in ocular activity.

Examples of methods of screening an agent for effects on toxic activity in conjunction with screening the agent for effects on other activities (e.g., angiogenesis activity and/or cell death activity) simultaneously in a teleost in vivo are described in U.S. Pat. Nos. 6,299,858 and 6,656,449, the disclosures of which are incorporated herein in their entirety for all purposes.

As previously noted, methods of screening agents for toxic activity and/or cell death activity are useful in combination with the methods disclosed herein for screening agents or an activity in an eye. The combination of such methods are particularly useful for assessing potential undesirable side effects of agents having a desired ocular activity, thereby providing in vivo data that can be used, for example, to eliminate certain agents or related structures having undesirable side effects from a drug development program or to predict a potential therapeutic window for certain agents for further in vivo testing.

In certain embodiments, screens for ocular activity and cell death or toxic activity can be performed simultaneously using methods in accordance with the present invention, as further discussed infra.

C. Screening Agents for Ocular Activity, Cell Death Activity and Toxic Activity Simultaneously The methods for screening agents for cell death activity can be combined with other methods of the present invention, including methods of screening agents for an ocular activity (Section III) and for toxic activity (see supra). Because teleosts are transparent, it is possible to assess effects on ocular activity, cell death activity, and toxic activity in teleosts in response to an agent simultaneously. Responses can be monitored in one or more tissues or organs and at predetermined time intervals.

As noted previously, these combined methods are useful in assessing multiple effects of an agent, including desired and undesired responses (such as detrimental side effects) and dose levels of the agent effective to promote one activity without promoting the other. The ability to assess multiple activities and responses in an animal due to the administration of an agent is of particular benefit in identifying potential therapeutic compounds and assessing their side effects. Pathological regulation of apoptosis, for example, is associated with a wide variety of human diseases including cancer, heart disease, neurodegenerative disorders, and immune, renal and viral-induced diseases. Essentially all cells are poised to commit suicide from the earliest stages of development. Thus, it is imperative that drugs be exactingly targeted. A balance must also be achieved during treatment with drugs such that only a negligible level of cell death and toxic effects in non-targeted tissues or organs. The combined methods of the invention are useful in assessing the specificity and extent of cell death and deleterious and toxic effects of potential drugs in particular organs and tissues or within the whole animal.

A variety of techniques can be used together or separately to analyze multiple activities/responses, including, e.g., fluorescence microscopy, light, microscopy, digital image analyzing, standard microplate reader techniques (colorimetry, fluorometry, including time-resolved fluorometry, and chemiluminescence), radiometric analysis, in situ hybridization, changes in enzymatic activity and levels in the whole teleost, or tissues, organs or cells of the teleost, antibody staining of specific proteins, changes in protein distribution temporally and spatially within the animal.

In one aspect, the present invention provides methods of screening an agent for an effect on ocular activity and cell death activity in vivo as described above which further comprise screening the agent for an increase or decrease in toxic activity by detecting a response in the teleost indicating an increase or decrease in toxic activity.

Examples of methods of screening an agent for effects on multiple activities (e.g., angiogenesis activity, cell death activity, and/or toxic activity) simultaneously in a teleost in vivo are described in U.S. Pat. Nos. 6,299,858 and 6,656,449, the disclosures of which are incorporated herein in their entirety for all purposes.

V. Automated Screening Methods

A. High Throughput Screening in Zebrafish

The multi-parametric methodology described above can be automated using standard instrumentation and computer software programs, permitting the screening of hundreds of agents per week. These methods combine the physiological advantages of the teleost and simplicity of agent addition with the ease of sample handling and detection provided by microtiter plates and associated dispensing and detection apparatus. The methods are premised, in part, on the observation that teleosts can be cultured and develop normally within the confined space of microtiter wells notwithstanding the accumulations of waste products and low availability of oxygen due to the confined space. Accordingly, large numbers of agents can be screened in parallel in the wells of a microtiter plate containing fertilized embryos. As for other screening methods discussed above, because teleost embryos develop normally in 100 µl of water, agents and dyes can easily be added to the medium. Furthermore, because transparent teleost embryos become opaque when they die, embryo lethality is comparatively straightforward to identify using a standard microtiter plate reader to calculate the LC50. In addition, a GFP transgenic fish can be monitored over time in a microplate reader.

An exemplary scheme for performing high throughput screening provided in U.S. Pat. Nos. 6,299,858 and 6,656,449, the disclosures of which are incorporated herein in their entirety for all purposes. Zebrafish embryos are contacted with agents to be screened for sufficient time for the agent to elicit a response indicative of a pharmacological activity in the zebrafish. The amount of time depends on the assay and can range from 1 hour to 7 days. Different wells can be used to test different agents, and/or to test the same agent at different concentrations. In some methods, each well contains a single zebrafish and in some methods, each well contains multiple zebrafish. After treatment, wells are analyzed to determine continued viability of zebrafish (e.g., by determining absorbance at 550 nm). Death of zebrafish results in high absorbance. Wells containing agents resulting in high lethality are not further pursued, but the identity of such agents can be stored in a computer file.

Wells containing viable zebrafish are then assayed for pharmacological activity of the agents being tested. This activity is often a change in concentration of a cellular marker or in the number of cells expressing a cellular marker. This activity can be detected using a substrate processed by the enzyme to generate an optically detectable product. After performing the assay, the plates are read for an optical signal indicating pharmacological activity. Agents showing good activity in the assay are then subjected to a confirmatory assay. This assay can be performed in a microtiter format as before, or can be performed by a different format on a teleost (e.g., a microscopic assay), or can be performed on a higher organism. In some methods, the confirmatory assay detects the same response as the primary assay but by a different means. For example, the primary assay can detect an increase in enzyme activity colorimetrically using a microplate reader, and the confirmatory assay can detect the same enzyme activity on a micrograph. Agents showing good activity are also tested for toxicity and lethality. These assays can be performed in a microtiter format or using other methods described above. Suitable enzymes whose activities are indicative of a toxicity response in the heart or liver, and substrate for detecting them are described in the Examples that follow.

The equipment used in the above assays typically includes a multiwell plate, apparatus for dispensing embryos, apparatus for dispensing small volumes to the wells, apparatus for mixing fluids in the wells, apparatus for washing the wells, a coding to label wells and the plate, a plate reader for detecting an optical signal from the wells and for reading the code and a computer for controlling the other apparatus and for storing data. For dispensing teleosts, an automated particle handling device equipped with a light scattering detection system which can contribute about 1 mm particles and distinguish dead embryos (white) from live embryos (transparent) is suitable (BD Biosciences, Bedford, Mass.). To add and remove liquid (e.g., media, washing solutions, labeling reagent solutions), an automatic microplate pipetting and washing workstation (Biomek, Beckman-Coulter, Caliper, Hopkinton, Mass.; Packard Bioscience, Groningen, The Netherlands) is suitable. The type of plate reader depends on the nature of the measurement to be made (i.e., fluorescence, chemiluminescence, colorimetric or radioactive via scintillation counting). Some commercially available plate readers can detect multiple types of signal. Multi-well plates typically have 96 wells, but larger or smaller number of wells can be used. In a standard plate, each well has a volume of about 300 µl but larger or smaller volume wells can be used. Typically, zebrafish are cultured in a volume less than 1 ml, sometimes less than 500 µl, sometimes 50-200 µl and preferably about 100 µl. Several laboratory and robotic systems have been developed for the purpose of processing microtiter plates. These devices are designed to increase laboratory throughput and many of these devices also provide positive sample identification through the use of analytical software and barcode labels. The correlation between identity of agents and wells can be referred to as a correspondence regime. Examples of suitable equipment are described below.

In accordance with the present invention, assays can be performed either on whole teleosts (e.g., to measure a second activity in at least one organ or tissue other than the eye) and/or on an isolated eye of the teleost. The teleosts can be natural or transgenic. The teleosts are living when contacted with agents. In some methods, teleosts are killed before detecting signal. In such methods, the agent being tested is typically removed. Teleosts can then be fixed or lysed to facilitate detection of signal. In some methods, the teleosts remain living throughout the assay including detection of optical activity (such as GFP). In such methods, a series of measurements of signal can be made over time on the same teleosts. In such methods, the agent being tested and the labeling reagent used to test response can be left in contact with the teleost throughout the assay. In some methods, in which an optical signal is generated within a teleost, the teleost should be sufficiently transparent that the optical signal can be detected in the whole teleosts. In other methods, the signal diffuses out of the teleost, or can be induced to do so by treatment with lysing agents. In such methods, transparency of the teleost is not necessary.

The extent or rate of appearance of a signal depends on the response of a teleost to an agent, and the response is in turn an indicator of a pharmacological activity of the agent. For example, modulation of angiogenesis is a pharmacological activity, an increase or decrease in a reporter enzyme (EC specific antigen or alkaline phosphatase) is a cellular response indicative of angiogenesis, and an $OD_{405}$ reading of HRP substrate is an optical signal that depends on the cellular response. Similarly, modulation of apoptosis is a pharmacological activity, an increase or decrease in caspases activity is a response indicative of modulation of apoptosis and various substrates of caspases are suitable labeling reagents for generating an optical signal dependent on the response.

In general, a pharmacological activity is a property of an agent that indicates that the agent is, or may be, useful for treatment and/or prevention of a disease. Thus, pharmacological activity includes prophylactic and therapeutic activities as defined herein. In general, responses indicative of pharmacological activity can include: 1) a increase or decrease in the number of cells or the concentration a cellular marker, such as an enzyme or secondary metabolite in a cell, 2) the modulation of a cellular pathway, for example, by binding of an agent to a cellular receptor, or 3) the promotion or inhibition of a physiological event such as cell growth or differentiation. Examples of cellular markers that can be detected include nucleic acids, carbohydrates, lipids, and proteins. Nucleic acids can be detected by a hybridization assay using a probe nucleic acid. Usually, the probe nucleic acid is labeled although secondary labeling schemes are also possible. Proteins can be detected using antibodies that specifically bind to the proteins. In some methods, the antibody is directly labeled and in other methods a secondary labeling scheme is used. Enzymes can be detected using a substrate processed by the enzyme to generate an optically detectable product. Modulation of cellular proliferation can be determined from corresponding modulation of component molecules, particularly constitutive expressed proteins, or nucleic acids.

Optical signals useful for monitoring cellular response include color, fluorescence, chemiluminescence, opacity, and radioactivity, the latter can be detected via scintillant induced light scattering. Responses can be detected by light scattering or photon counting or other methods. In some methods, a product having an optical signal is generated by a reaction within cells of the teleosts, and is an indication of the level of a particular enzyme catalyzing the reaction. In other methods, the labeling reagent is attached directly to an agent, such as antibody, that binds to a cellular molecule. In some methods, the labeling reagent is attached to a secondary-labeling reagent that binds.

Usually some wells of the multiwell plate are occupied by positive and negative controls. Positive controls can be agents (s) known to have the pharmacological activity being tested for and negative controls, agent(s) known to lack the pharmacological activity. In some methods, multiple positive and/or negative controls are distributed at different locations on the plate. Of course, some wells in a multi-well plate need not be used at all.

Microplate assays can also be used to monitor absorbance, excretion, metabolism or intracellular distribution of an agent in teleosts. In such methods, the wells provide a means to contain teleosts while an agent redistributes between media and the teleosts, and/or is metabolized within the teleost. Initially, the agent can be in the medium only, in the teleost only, or in both the teleost and the medium. After culturing the teleost for a period, the amount of the agent in the medium, or the teleost or both is determined. A decrease in the amount of agent in the medium over the incubation period is a measure of absorption of the agent and allows calculation of an absorption rate. An increase in the amount of agent and its metabolites in the medium over the incubation period is a measure of excretion of the agent and allows calculation of an excretion rate. An increase in amount of agent in the teleosts over the incubation period reflects a net absorption. A decrease in amount of agent in the teleost over the incubation period reflects a net excretion. By performing the assay with different initial concentrations of agent in the media and the teleosts, it is possible to calculate the rates of both of these processes. In methods in which the detection assay distinguishes between the agent and metabolic products of the agent, it is also possible to calculate a metabolism rate.

In some methods, the agent itself generates an optically detectable signal or can be labeled with a secondary labeling reagent that gives rise to such a signal. The combined amount of agent in medium and teleost is detected with microplate reader. After detection, the medium is discarded and the amount of agent within the teleosts is detected.

In some methods, when the agent is not labeled, the amount of agent in media can be determined by extracting the medium with chloroform (most small molecule agents are soluble in chloroform) or other organic solvent to isolate the agent, and quantifying the agent by HPLC/MS designed for automation. The agent within teleosts can be extracted with an organic solvent such as chloroform. The extracted agent and its metabolite can be analyzed by HPLC/MS designed for an automation system. In some methods, the teleost is fixed after culturing with the agent, and the location of agent within the teleost is determined by microscopic examination.

Examples of methods of high throughput screening of agents for effects on multiple activities (e.g., angiogenesis activity, cell death activity, and/or toxic activity) simultaneously in a teleost in vivo are described in U.S. Pat. Nos. 6,299,858 and 6,656,449, the disclosures of which are incorporated herein in their entirety for all purposes.

EXAMPLES

Example 1

Zebrafish Hypoxia-Induced Choroidal Neovascularization (CNV) Model and Use of the CNV Model to Test Effects of Anti-Angiogenic Drugs Ocular or choroidal neovascularization (CNV) occurs in age-related macular degeneration (AMD). As previously discussed, AMD is the leading cause of blindness in adults over 60 (see Klein et al., *Am, J. Ophthalmol.* 137:486, 2004). AMD, which is responsible for profound vision loss, has two forms: dry and wet. The "dry" form is an early form of AMD, thought to progress into a more advanced "wet" form. The wet form of AMD is associated with sudden vision loss due to abnormal blood vessel growth (i.e., choroidal neovascularization) under the macula.

A. Hypoxia-Induced Choroidal Neovascularization (CNV) Model

Using a low (0.1 mg/ml) concentration of $CoCl_2$, hypoxia was induced in the zebrafish eye and abnormal vessel growth was observed, specifically in the choroidal region.

To establish a reproducible animal model for choroidal neovascularization (CNV), the optimal concentration and embryo stage for $CoCl_2$ treatment was determined. Since hypoxia induced later than 24 hours post fertilization (hpf) causes lethality in zebrafish within 24 hours (Padilla and Roth, Proc. Natl. Acad. Sci. USA 98:7331-7335, 2001), zebrafish were initially treated at 6 and 24 hpf with several concentrations of $CoCl_2$, ranging from 25 mg/ml to 0.01 mg/ml. Angiogenesis in the eye was detected sing Phy-V (Phylonix, Cambridge, Mass.), a monoclonal antibody that specifically stains activated ECs in nascent vessels. Continuous treatment of 24 hpf zebrafish for 4 days with a low concentration of $CoCl_2$ (0.1 mg/ml) stimulated angiogenesis throughout the 5-day post fertilization (dpf) zebrafish; 64 of 102 treated zebrafish (63.6±11.1%) exhibited CNV specific phenotype (see Table II). Phy-V staining was strongest in: intersegmental vessels (ISVs), cranial vessels (CRVs), and eye vessels (EVs), particularly in the choroidal region. Higher magnification of the eye showed an abnormal network of new choroidal vessels, not observed in untreated control zebrafish. In some zebrafish, edema was observed in the area surrounding the region of abnormal vessel growth, similar to the CNV, a phenotype observed in advanced AMD in humans. The overall body morphology of $CoCl_2$ treated zebrafish was similar to untreated zebrafish, and other organs, including heart, intestine, and liver were intact and development appeared normal. This observation indicated that continuous treatment with a low concentration of $CoCl_2$ did not cause obvious toxicity in zebrafish, and that stimulation of angiogenesis was vessel specific and not the result of toxicity. A higher concentration of $CoCl_2$ (1 mg/ml) did not increase the frequency or severity of CNV, but did increase toxicity. After exposure to 20 mg/ml CoCl2 for two days, 100% of zebrafish began dying, apparently from general toxicity. Shorter treatment with 0.1 mg/ml $CoCl_2$ did not stimulate vessel growth. Therefore, as the method for generating the CNV disease model, treated 24 hpf zebrafish with 0.1 mg/ml $CoCl_2$ continuously for 4 days.

The CNV model was further characterized to investigate whether abnormal vessels penetrated the retina. Immunohistochemical staining of new vessel formation in the eye was performed. Under normal conditions, zebrafish do not have vessels in the retina, however, $CoCl_2$ treated zebrafish exhibited abnormal vessels formed in the retina. Edema, a phenotype seen in human CNV, and degenerated photoreceptors were also observed. This result demonstrated that a low concentration of $CoCl_2$ treatment induced abnormal CNV and that abnormal vessels penetrated deeply into the retinal layer of the zebrafish eye.

Figure 4:
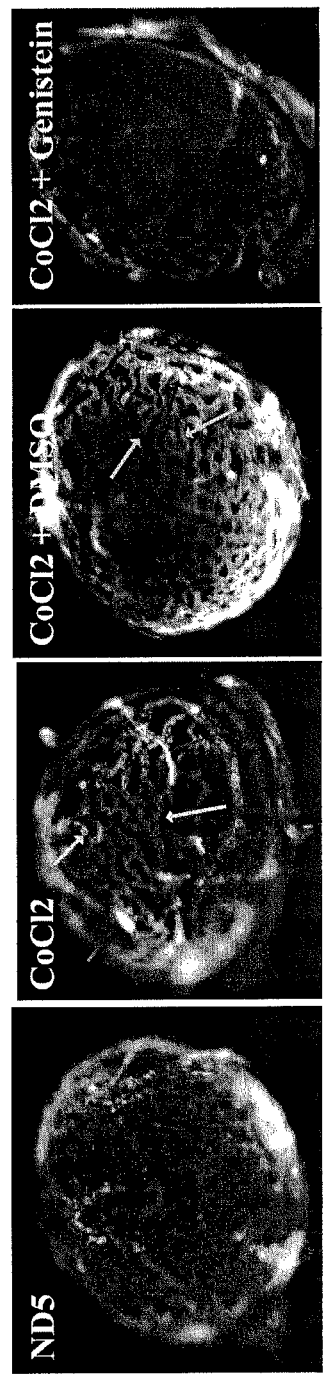
FIG. 4 shows the effects of drugs on the choroidal plexus on isolated eyes. Control and drug treated 5 dpf zebrafish were processed with whole mount immunostaining with Alexa 488 conjugated Phy-V. After extensive washing, 150 U/ml of collagenase was added to the zebrafish. After incubating at 37° C. for 45 minutes, eyes were dissociated from the body by gently pipetting the solution up and down a few times. For image capture, isolated eyes were then placed on depression slides with the choroidal plexus side facing up. NDS: from untreated 5 dpf zebrafish, $CoCl_2$: from 0.1 mg/ml. $CoCl_2$ treated zebrafish, $CoCl_2$+0.01% DMSO: from $CoCl_2$ and 0.1% DMSO co-treated zebrafish, $CoCl_2$+Genistein: from $CoCl_2$ and Genistein co-treated zebrafish. Yellow arrows indicate the individual vessels in the plexus. Red arrows indicate high fluorescence staining, implying the ECs in these vessels were highly activated.

To investigate whether a different hypoxia-inducing agent can cause severe CNV, another hypoxia-inducing agent; Penicillamine, was used to assess CNV formation. Penicillamine, a nitric oxide (NO) donor, has been shown to up-regulate HIF-1α through a different mechanism than the mechanism of $CoCl_2$, and to stimulate angiogenesis in mice. (See Jozkowicz et al., Cardiovasc. Res. 51:773-783, 2001; Sandau et al., Blood 97:1009-1015, 2001; Gallo et al., Biochem. Biophys. Res. Commun. 299:517-524, 2002; Kawasaki et al., Mol. Cell. Biol. 23:5726-5737, 2003.) FIG. 4 shows that 0.01 μM Penicillamine treatment at the 24 hpf stage also stimulated angiogenesis throughout the zebrafish. Starting at 2 dpf, abnormal choroidal vessels (eye vessels; EVs) were observed. At 5 dpf, angiogenesis in the cranial vessels (CRVs), EVs, and the trunk and tail intersegmental vessels (ISVs) increased and CNV was observed. Fewer zebrafish developed CNV with Penicillamine treatment than with $CoCl_2$ treatment, and the level of abnormal angiogenesis was also lower than results induced by $CoCl_2$ treatment. Since $CoCl_2$ and Penicillamine up-regulate HIF-1α through different mechanisms and yielded the same phenotype, these results further support the hypothesis that hypoxia is one of the major mechanisms in the $CoCl_2$ zebrafish CNV model.

B. Up-Regulation of Hypoxia Genes in the Zebrafish CNV Model

Figure 2:
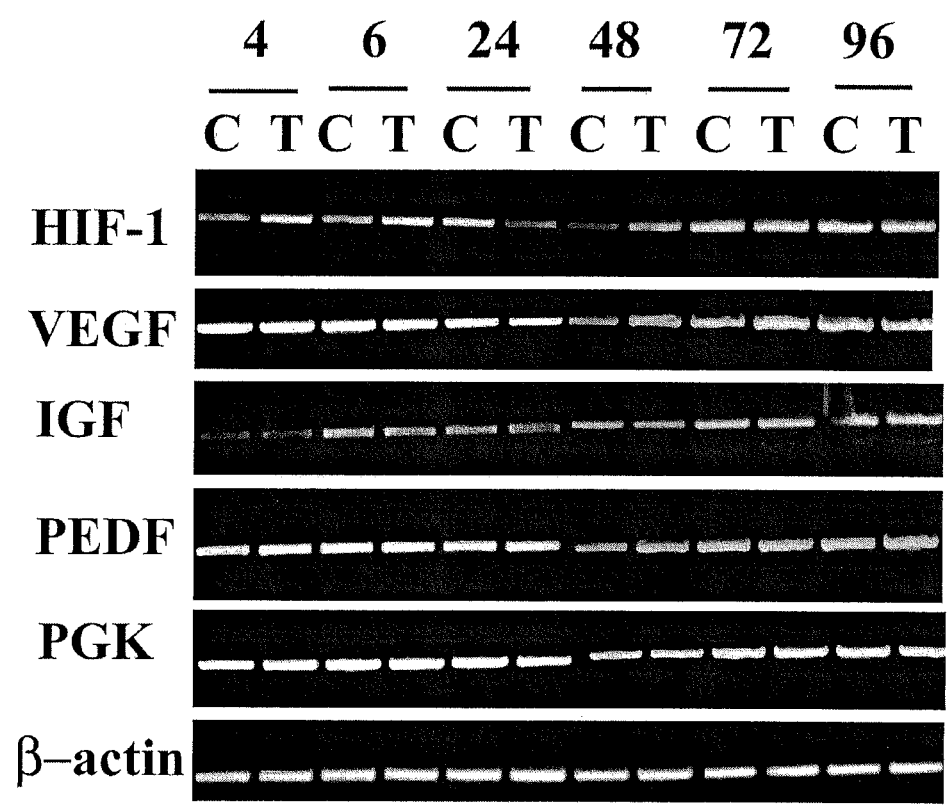
FIG. 2 shows a comparison of hypoxia related gene expression profiles in control and $CoCl_2$ treated zebrafish. 24 hpf zebrafish were treated with $CoCl_2$. At 4, 6, 24, 48, 72, and 96 hours post treatment (hpt), control and treated zebrafish were analyzed by RT-PCR. For comparison, controls were run with each treatment group. C: control group, T: $CoCl_2$ treated group. HIF-1α up-regulation was observed at 4, 6, 48 hpt; however, down-regulation of HI-1α was observed at 24 hpt. Up-regulation of VEGF was observed at 48 and 72 hpt. β-actin: loading control.

To confirm up-regulation of hypoxia genes in the $CoCl_2$ zebrafish CNV model, RT-PCR and in situ hybridization experiments were performed. Two genes, HIF-1α and VEGF, are known to be involved in hypoxia. IGF and PEDF have also been implicated in ocular neovascularization. PGK is a gene involved with energy synthesis, which is related to oxygenation. Since induction or up-regulation of genes precedes manifestation of the CNV phenotype, we assessed expression of these 5 genes by RT/PCR from 4 to 96 hours after $CoCl_2$ treatment, which began at 24 hpf. Results are summarized in FIG. 2 and Table II.

As early as 4 hours after $CoCl_2$ treatment (hpt), HIF-1α up-regulation was observed, which persisted to 48 hpt, except at 24 hpt, HIF-1α down-regulation was observed. While determining the optimum $CoCl_2$ treatment, we observed instantaneous death when $CoCl_2$ was added at the 48 hpf stage (equivalent to 24 hpt). Up-regulation of VEGF was observed starting at 48 hpt, which was later than HIF-1α up-regulation, and then gradually decreased. No change in gene expression was observed for PEDF, IGF, and PGK. This result confirms that a significant level of hypoxia is present in $CoCl_2$ treated 3 dpf zebrafish, which results in the CNV phenotype at later stages.

TABLE II

| RT-PCR results of $CoCl_2$ treated zebrafish | | | | | | | |
|---|---|---|---|---|---|---|---|
| Gene | Function | 4 | 6 | 24 | 48 | 72 | 96 |
| HIF-1α | Nuclear transcription factor | ↑ | ↑ | ↓ | ↑ | — | — |
| VEGF | Growth factor specific for EC proliferation | — | — | — | ↑ | ↑ | — |
| IGF | Insulin-like growth factor | — | — | — | — | — | — |
| PEDF | Endogenous angiogenesis inhibitor produced by pigment epithelium in retina | — | — | — | — | — | — |
| PGK | Glycolytic enzyme | — | — | — | — | — | — |

*Hours post $CoCl_2$ treatment, Up arrows indicate up-regulation; down arrows indicate down-regulation; horizontal line indicates no change.

In situ hybridization was performed to confirm that HIF-1α expression was up-regulated in the zebrafish eye in response to $CoCl_2$ treatment. At 24 hpt (48 hpf zebrafish), control zebrafish showed a slightly higher level of HIF-1α in the whole brain region, which agreed with RT-PCR results. In zebrafish at 48 hpt (72 hpf zebrafish), HIF-1α expression was higher in the liver/gut region, the brain and eye region, especially in the lens, compared to the sense control and untreated control zebrafish. At 72 hpt (96 hpf zebrafish), HIF-1α expression was present primarily in the gut region and no difference was detected in control and $CoCl_2$ treated zebrafish. These results correlated well with RT-PCR results and further confirmed that hypoxia is the likely mechanism of $CoCl_2$ induction of the CNV phenotype in zebrafish.

C. Effects of Anti-Angiogenic Drugs in the Zebrafish CNV Model

To further characterize the CNV model, $CoCl_2$ treated zebrafish were co-treated with anti-angiogenic compounds to evaluate their effect on new blood vessel formation in zebrafish and compare results with other mammalian models. Celebrex, a COX-2 inhibitor, and Genistein, an isoflavone natural product and a kinase inhibitor, were tested as they are commercially available and undergoing clinical trials as potential AMD therapeutics.

24 hpf zebrafish were treated with 0.1 mg/ml $CoCl_2$ continuously for 4 days, and various concentrations of Celebrex or Genistein were incubated with the zebrafish. At the 5 dpf stage, zebrafish were fixed and stained with zebrafish angiogenic-vessel-specific antibody, Phy-V. Several treatment strategies were assessed: (1) pre-treatment (high concentration of drug added for 4 hours and withdrawn before $CoCl_2$ induction); (2) co-treatment (drugs were co-treated with $CoCl_2$); and (3) post-treatment (drugs were added 24 hours after $CoCl_2$).

The most effective treatment regimen was found to be co-treatment. In untreated 5 dpf zebrafish, the choroidal vessel plexus includes the major vessels with a minimal network of small vessels. In $CoCl_2$ and $CoCl_2$+DMSO treated control zebrafish, an extensive region in the choroidal vessel plexus was covered by a network of small vessels. In $CoCl_2$+Celebrex treated zebrafish, the choroidal region exhibited a minimal network of small vessels with clearly visible major vessels, similar to the phenotype in untreated zebrafish. In $CoCl_2$+Genistein treated zebrafish, eyes were clear with a minimal network of small vessels and clear major vessels in the choroidal plexus region were observed. These results demonstrate that Celebrex and Genistein prevented abnormal neovascularization.

Figure 3:
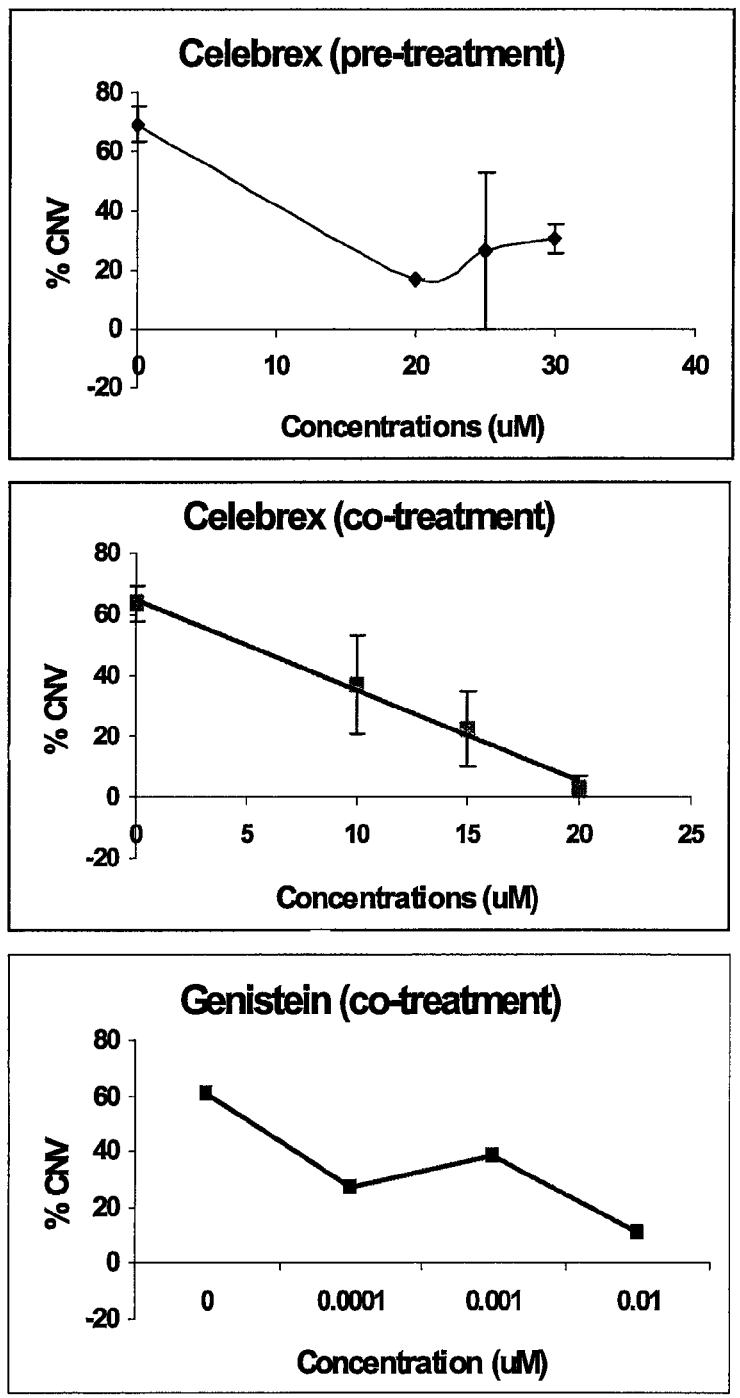
FIG. 3 shows dose response curves of drug effects as quantified by visual assessment. Tables II and III show the number of zebrafish exhibiting severe CNV; % CNV zebrafish versus drug concentration was plotted to generate a dose response curve. As the drug concentration increased, the % of CNV zebrafish decreased. Each point represents mean±SE.

The drug effects on CNV zebrafish were assessed visually using microscopic examination of Phy-V stained whole zebrafish. % CNV inhibition was calculated by dividing the total number of CNV zebrafish by the total number of zebrafish per experiment (Tables II and III). The percentage of CNV zebrafish was lowest after co-treatment with Celebrex. Pre-treatment with a high concentration of Celebrex for a shorter time generated a low percentage of CNV zebrafish, however, the CNV defects were severe, implying that pre-treatment did not completely inhibit CNV. Post-treatment with Celebrex showed limited inhibition of $CoCl_2$ induced CNV, and the experiment was discontinued. FIG. 3 shows the dose response curves based on visual observation of whole mount Phy-V stained CNV zebrafish.

TABLE III

Effect of Celebrex on $CoCl_2$ induced CNV (Co-treatment)

| Conc (μM) | Total zebrafish | CNV zebrafish | % CNV | Mean ± SE (% CNV) |
|---|---|---|---|---|
| 0 | 16 | 12 | 75.0 | 63.6 ± 5.6 |
|   | 20 | 15 | 75.0 |   |
|   | 22 | 10 | 45.0 |   |
|   | 25 | 15 | 60.0 |   |
|   | 19 | 12 | 63.2 |   |
| 10 | 17 | 9 | 52.9 | 37.0 ± 16.1 |
|    | 19 | 4 | 21.1 |   |
| 15 | 7 | 3 | 42.9 | 22.1 ± 12.4 |
|    | 15 | 0 | 0 |   |
|    | 15 | 0 | 0 |   |
|    | 17 | 4 | 23.5 |   |
| 20 | 5 | 0 | 0 | 3.3 ± 3.3 |
|    | 26 | 0 | 0 |   |
|    | 20 | 2 | 10.0 |   |

TABLE IV

Effect of Genistein on $CoCL_2$ induced CNV (Co-treatment)

| Conc (μM) | Total zebrafish | CNV zebrafish | % CNV | Mean ± SE (% CNV) |
|---|---|---|---|---|
| 0 | 18 | 8 | 44.4 | 60.4 ± 5.6 |
|   | 25 | 15 | 60.0 |   |
|   | 16 | 12 | 75.0 |   |
|   | 20 | 15 | 75.0 |   |
|   | 22 | 10 | 45.0 |   |
|   | 19 | 12 | 63.2 |   |
| 0.0001 | 18 | 2 | 11.1 | 20.8 |
|        | 23 | 7 | 30.4 |   |
| 0.001 | 19 | 7 | 36.8 | 38.0 |
|       | 23 | 9 | 39.1 |   |
| 0.01 | 17 | 4 | 23.5 | 23.5 |

D. Determination of Drug Effects on Zebrafish Eye Development

Since profound choroidal vessel plexus formation in normal zebrafish is usually observed after day 5, it is possible that the preventive effect observed after drug treatment was not due to inhibition of angiogenesis, but was due to inhibition of eye development. To rule out this possibility; immunohistochemistry to examine the structure of the zebrafish eye after Celebrex treatment was performed. Under riming conditions, 5 dpf zebrafish exhibit a distinctive 5 layer retinal structure comprised of: 1) ganglion cells (GCL); 2) inner plexiform (IPL); 3) inner nuclear (INL); 4) outer plexiform (OPL); and 5) outer nuclear 1 (ONL), and no vessels. However, in day 3 and 4 zebrafish, the nuclear and plexform layers are not yet mature and the 5 layers are not distinctively separated.

Therefore, histological differences in the retina structure can be used to easily assess eye development. 0.1 mg/ml $CoCl_2$-treated 5 dpf zebrafish exhibited an abnormal retinal structure: the INL was disrupted, the retina was degenerated, and vessel structure was abnormal. $CoCl_2$+0.8% DMSO-treated 5 dpf zebrafish showed a severely degenerated retinal structure, newly formed vessels invading the retina from the choroidal layer, and a degenerated photoreceptor layer, indicating that DMSO alone did not prevent $CoCl_2$-induced CNV. $CoCl_2$+20 μM Celebrex-treated 5 dpf zebrafish exhibited normal 5 layer structure with no vessels present in the retina. These results clearly demonstrate that Celebrex treatment did not delay eye development and prevented $CoCl_2$ induced CNV formation.

E. Conclusions

The zebrafish eZ-CNV™ model is specific for retinal and choroidal neoangiogenesis. Using a low concentration (0.1 mg/ml) of $CoCl_2$, a zebrafish model for CNV was generated. $CoCl_2$ treatment did not inhibit zebrafish development, as evidenced by normal body morphology shown in FIG. 2. Although at 5 dpf, the stimulatory effect on angiogenesis was present throughout the zebrafish body, evidenced by a high level of fluorescence in the trunk and tail ISVs after staining with Phy-V, the most striking effect was observed in the network of small vessels in the choroidal region of the eye, which was often accompanied by edema in the surrounding tissue, a phenotype also present in CNV observed in AMD patients. Using immunohistochemistry, abnormal angiogenic vessels was observed in the choroidal region penetrating the retinal layer of the zebrafish eye, which normally, does not include vessels; this result indicates that abnormal neovascularization is a pathological phenotype. In addition, the ISV pattern was unaffected, indicating that development was not affected and that toxicity was not a concern.

Hypoxia is a major mechanism of abnormal angiogenesis in the zebrafish eZ-CNV™ model. Based on the above, hypoxia is the mechanism involved in $CoCl_2$ induced CNV. To support this conclusion, an additional chemical was assessed: Pencillamine, a nitric oxide donor that up-regulates HIF-1α expression and stimulate angiogenesis in mice. Using Pencillamine, abnormal angiogenesis in the eye vessels was also observed, although the effect was not as severe as the effect in $CoCl_2$ treated zebrafish. Using RT-PCR analysis, up-regulation of HIF-1α and VEGF expression in $CoCl_2$ treated zebrafish was confirmed. The up-regulation of HIF-1α preceded the VEGF response. Since VEGF is one of the target genes of HIF-1α regulation (see Giatromanolaki et al., J. Surg. Oncol. 94:242-247, 2006), delayed up-regulation agrees with the hypothesis that hypoxia is the mechanism involved in $CoCl_2$ induced CNV. Using in situ hybridization, up-regulation of HIF-1α in the eye region was confirmed. This result further supports the theory that hypoxia is the likely mechanism of CNV in our zebrafish model.

Inflammation plays an important role in our eZ-CNV™ model. Two potential anti-angiogenic drugs, Celebrex and Genistein, both in clinical trials for CNV in AMD patients, were tested in the CNV model. Both drugs not only inhibit vascular endothelial cell (EC) proliferation/migration, but also inhibit inflammatory responses. The presence of edema in the $CoCl_2$ treated zebrafish eyes and the effectiveness of these two anti-inflammatory drugs in preventing the CNV phenotype in our model imply that, in addition to angiogenesis, inflammation plays a crucial role in our $CoCl_2$ induced zebrafish CNV model.

F. Materials and Methods

Zebrafish Collection. Albino zebrafish were generated by natural pair-wise mating according to the Zebrafish Handbook (Westerfield, 1993, supra). 4-5 pairs were set up for each mating; 100-150 embryos per pair were generated. Embryos were maintained in embryo water (5 g of Instant Ocean Salt in 25 liters of distilled water) at 28° C. Zebrafish were dechorionated by incubating with protease, 1 mg/ml, at room temperature for 3 minutes. Dechorionated embryos were then used for all studies.

Chemicals and Reagents. Chemicals and reagents were purchased from Sigma Aldrich Co. (St. Louis, Mo.). Celebrex was purchased from Sequoia Research Product Ltd. (Oxford, UK). Phy-V antibody was generated by Phylonix and labels activated endothelial cells. Rhodamine conjugated secondary antibodies were purchased from Jackson ImmunoResearch Laboratories, Inc. (West Grove, Pa.). Horseradish peroxidase (HRP) suppressor, HRP-conjugated secondary antibodies, and TMB kit, were purchased from Pierce (Rockford, Ill.).

Imaging Instrumentation. A Zeiss M2Bio fluorescence microscope (Carl Zeiss Microimaging Inc., Thornwood, N.Y.), equipped with a rhodamine cube with a green FITC filter (excitation: 488 μm, emission: 515 nm), and a chilled CCD camera (Axiocam MRM, Carl Zeiss Microimaging Inc., Thornwood, N.Y.) was used. Images were analyzed with Axiovision software Rel 4.0 (Carl Zeiss Microimaging Inc., Thornwood, N.Y.), and Adobe Photoshop 7.0 (Adobe, San Jose, Calif.).

$CoCl_2$ Treatment. $CoCl_2$ (Sigma, St Louis, Mo.) was dissolved in fish water and serially diluted to the desired concentration. Because the mortality rate significantly increases in hypoxic conditions after 24 hours of development (see Padilla and Roth, Proc. Natl. Acad. Sci. USA 98:7331-7335, 2001), zebrafish were treated at or before 24 hours post fertilization (hpf) with: 20, 10, 5, 1, 0.5, and 0.1 and 0.01 mg/ml $CoCl_2$ in fish water for varying times.

RT-PCR. Total RNA was isolated from control and drug treated zebrafish and reverse-transcribed with MMLV reverse-transcriptase (GIBCO/BRL) primed with oligo dT and subjected to PCR using zebrafish specific primers. The primers used were: HIF (left: 5'-GAC GTG GAA GGT TCT TCA CTG-3' (SEQ ID NO:1), right: 5'-TCA AGA GGT CAT CTG GCT CAT-3' (SEQ ID NO:2)), VGEF (left: 5'-GTA AAG GCT GCC CAC ATA CC-3' (SEQ ID NO:3), right: 5'-GCT TTG ACT TCT GCC TTT GG-3' (SEQ ID NO:4)), IGF (left: 5'-AGT GAT GCC CGC ATT AAA AC-3' (SEQ ID NO:5), right: 5'-TCT GTG CAA ACG ATC CTG TC-3' (SEQ ID NO:6)), PEDF (left: 5'-AGC TAT CAA TGG GAG CGT CT-3' (SEQ ID NO:7), right: 5'-CTC CAC CAG CAA GAA TCT GA-3' (SEQ ID NO:8)), and PGK (left primer: 5'-GCC TCT GTG GTT TCT CAA GG-3' (SEQ ID NO:9), right: 5'-AGG CCT CTG TGG TTT CTC AA-3' (SEQ ID NO:10)). β-actin was used as an internal control. Semi-quantitative PCR was performed using Advantage 2 Taq Polymerase (BD Biosciences, Palo Alto, Calif.) in an MJ Research PTC-100 thermocycler using the following cycling parameters: 94° C. for 2 min followed by 30 cycles of [94° C. 1 min, 59° C. 30 sec, 72° C. 1 min] followed by 72° C. for 10 min. PCR products were visualized following electrophoresis in a 2.0% agarose gel and stained with ethidium bromide.

Whole Mount In Situ Hybridization. Zebrafish were fixed with 4% paraformaldehyde in PBS and re-hydrated with PBST. TRNA probes were hybridized at 65° C. in hybridization solution (50% Formamide, 5.times.SSC, 0.1% Tween 20, 0.05 mg/ml Heparin, 0.5 mg/ml tRNA, 10 mM Sodium Citrate buffer pH 6.0). Alkaline phosphatase-conjugated anti-digoxigenin antibody was used for detection. For staining, zebrafish were equilibrated in NTMT buffer (0.1 M Tris/HCl pH 9.5, 50 mM MgCl, 0.1 M NaCl, 0.1% Tween 20) at room temperature. Once zebrafish were equilibrated, 4.5 μl of 75 mg/ml NBT (Nitro Blue Tetrazolium) and 3.5 μl of 50 mg/ml BCIP (5-Bromo-4-Chloro-3-Indolyl-Phosphate) per ml were added to the staining solution. The staining reaction was stopped by washing zebrafish with PBST. Zebrafish were then examined on a stereo-dissecting microscope.

Celebrex or Genistein Co-Treatment. Celebrex and Genistein dissolved in DMSO were added directly to fish water, the final concentration of DMSO for Celebrex and Genistein was 0.8%. For pre-treatment, 24 hpf zebrafish were incubated with high concentrations of each drug at 28° C. for 4 hours; the drugs were washed off and zebrafish were treated with 0.1 mg/ml $CoCl_2$. For co-treatment, each drug was added simultaneously with 0.1 mg/ml $CoCl_2$. For post-treatment, each drug was added 24 hours after $CoCl_2$ addition. After drug treatment, zebrafish were washed and processed for whole mount immunochemical staining Whole Mount Immunofluorescence Staining. Zebrafish were fixed by Dent's fixative (DMSO/methanol=⅓) and processed for whole mount immunochemical staining following standard procedures (Westerfield, 1993, supra). Alexa 488 conjugated Phy-V antibody (Phylonix), which specifically labels activated endothelial cells, was used to stain zebrafish, and followed by examination by fluorescence microscopy.

Immunohistochemistry and Microscopy. Zebrafish were fixed in Dent's fixative (4:1 methanol:DMSO) for 3 hours at room temperature, dehydrated stepwise into methanol and whole mount antibody labeling was performed using standard methods, as described in Westerfield, 1993. Phy-V was used as the primary antibody, followed by staining with HRP-conjugated secondary antibody (Jackson ImmunoResearch, West Grove, Pa.); DAB (Jackson ImmunoResearch). After staining, zebrafish were embedded in JB-4 (Polysciences, Inc. Warrington, Pa.), a transparent media, following manufacturer's instructions. Whole mount immunostained zebrafish were sectioned to obtain sagittal sections (5 μm thick); slides were then counter-stained by either nuclear fast red or methylene blue (Sigma-Aldrich). Because JB-4 ordinarily inhibits penetration of large molecules, e.g., antibodies, instead of using conventional immunohistochemistry, zebrafish were stained and sectioned. Sections were then used for microscopy.

Calculation of Drug Effects. To reduce the variability contributed by substrate and to compare results from different assays performed on different days, drug effects were normalized to % inhibition on EC proliferation. Chemiluminescent signal (CU) in each well (containing 4 eyes) was measured and used to calculate drug effect. For each assay, 24 $CoCl_2$ treated eyes (C) and 24 DMSO and $CoCl_2$ co-treated eyes (D) were compared to confirm that drug carrier did not cause adverse effects. In addition, to estimate non-specific background signal, 24 C were processed without antibody incubation; the mean value of which was subtracted from each CU measurement. Mean CU of D was used as 100% control. Drug effect was calculated following formula (a).

$$\%\text{Inhibition} = (1 - (CU(\text{drug treated})/CU(\text{control}))) \times 100\% \quad (a)$$

ANOVA was used to analyze significance of drug effect; * represented $P<0.1$, ** represented $P<0.05$. All calculations were performed using MS EXCEL (Microsoft Corporation, Seattle, Wash.) and GraphPad Prism 4 software (San Diego, Calif.).

Example 2

Zebrafish Ocular Scarring Model

Scar formation typically occurs during the wound healing process, such as, for example, following surgery. As previously discussed, supra, wound healing takes places in three stages: inflammation, proliferation, and maturation. During these three stages of the healing process, fibroblast cells and new vessels comprised of endothelial cells (angiogenesis) proliferate, which results in scar formation in the wounded area. Such scarring occurs, for example, following ocular surgery for glaucoma. A zebrafish model for ocular scarring was developed, as described below.

Ocular scarring was generated in the zebrafish eye 1 day after microsurgery similar to scar formation visible in mouse eye 7 days after cutting the conjunctiva. Zebrafish ocular scarring is also similar to scarring in rabbits (see Cordeiro et al., *Invest. Ophthalmol. Vis. Sci.* 40:2225-2234, 1999), however, in zebrafish it is not necessary to build a functioning filtering bleb by microsurgery and to wait for 2 weeks to observe scar formation. We used adult zebrafish for this study rather than embryos or larval stage because: 1) the eye of adult zebrafish is most similar to the eye of adult humans; 2) the majority of primary glaucoma occurs in adults over 40; and 3) adult zebrafish are fully developed and the process of wound healing in adult zebrafish should be similar to wound healing in human adult. In order to establish a simple, rapid zebrafish scarring model using microsurgery, we first surgically cut the conjunctiva and then burned the sclera using procedures that take less than 1 minute per eye. In addition, drug treatment in zebrafish is simple and shorter than treatment in other animal models. Anti-scarring agents can be screened on a large scale using a large number of animals, which increases confidence in statistical analysis. Advantages of this approach include: 1) short assay time; 2) single dosing; 3) small amount of drug required for each test; 4) statistically significant numbers of animals can be assayed for each condition; and 5) low cost (Table V).

TABLE V

Comparison of drug screening for ocular scarring in zebrafish and other animal models

| Animal Model | Surgical Time/Eye | Scarring Formation | Cost/Animal | Single Dose/Animal | Drug Treatment | Drug Screening/Month |
|---|---|---|---|---|---|---|
| Monkey | 30 minutes | 2 weeks | $700 | μM | 2-3 weeks | <3 drugs |
| Rabbit | 30 minutes | 2 weeks | $80 | μM | 2-3 weeks | <3 drugs |
| Rat | 20 minutes | 2 weeks | $30 | μM | 2-3 weeks | <3 drugs |
| Mouse | 20 minutes | 1 weeks | $20 | μM | 1-2 weeks | <3 drugs |
| Zebrafish | <1 minute | 1 day | <$1 | pM | <1 week | >10 drugs |

Example 3

Dissociation of Intact Eyes from Zebrafish and Development of Eye-Specific Angiogenesis ELISA A. Method for Dissociating Eyes from Whole Zebrafish A method to rapidly dissociate eyes from whole mount immunostained zebrafish was developed by incubating zebrafish with a collagenase enzyme (Clostridium histolyticum collagenase Type II, Gibco) at various enzyme concentrations and temperatures, and for various periods of time. The enzyme concentrations ranged from 15 U/ml up to 150 U/ml. The temperature ranged from room temperature to 37° C. The period of incubation ranged from 30 minutes up to 16 hours. It was found that the enzyme concentration, temperature and period of time have to be coordinated to dissociate intact eyes. Using this collagenase, 150 U/ml of enzyme at 37° C. for 45 minutes and dissociating eyes (see FIG. 1) by gentle pipetting was effective in dissociating intact eyes. Using this approach, the vascular structure in the choroidal vessel plexus can be easily visualized (FIG. 4). Activated EC (bright fluorescence, red arrows) were seen in $CoCl_2$ and $CoCl_2$+DMSO treated zebrafish eyes which were highly vascularized (yellow arrows) compared to untreated 5 dpf (ND5) and $CoCl_2$+Genistein treated eyes.

B. CNV Quantitation by Eye-Specific Angiogenesis ELISA

The rapid isolation method described above provides a unique opportunity to quantify CNV with no background signal contributed by vessels present in other organs and tissues in the whole zebrafish. Using this approach, an eye-specific angiogenesis ELISA (eZ-CNV™ ELISA) was developed.

Figure 5:
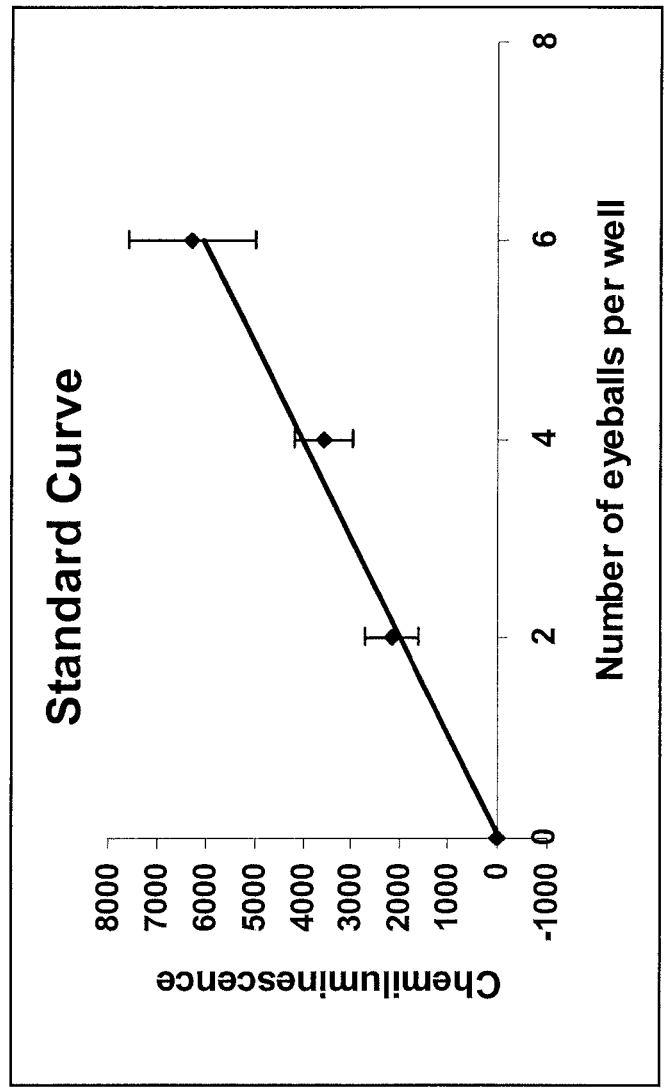
FIG. 5 shows a standard curve for eye specific angiogenesis ELISA. $CoCl_2$ treated zebrafish were stained with HRP conjugated Phy-V and eyes were isolated using collagenase treatment as described in Materials and Methods. Eyes were placed into wells of a 96-well microtiter plate. The chemiluminescence HRP substrate, PS-atto (Lumigen), was used for signal development. A linear relationship was observed between chemiluminescence signal and number of eyes in each well. Each point represents the mean±SD (5≤n≤18).

To develop a valid assay, it was necessary to determine the optimal number of eyes to detect differences in signals. $CoCl_2$ treated zebrafish were used with a chemiluminescence HRP substrate, PS-atto (Lumigen, Southfield, Mich.). $CoCl_2$ treated zebrafish were stained with HRP conjugated Phy-V, and eyes were isolated using the dissociation method described above and placed into 96-well microtitre plates. As shown in FIG. 5, a linear relationship was observed between the chemiluminescence signal and the number of eyes per well. Since the signal from 4 eyes per well was in the middle of the linear curve, this number was used as the optimal number of eyes required to distinguish signal difference in either direction for the specific angiogenesis ELISA.

C. Effects of Anti-Angiogenic Drugs in the Zebrafish CNV Model

Figure 6:
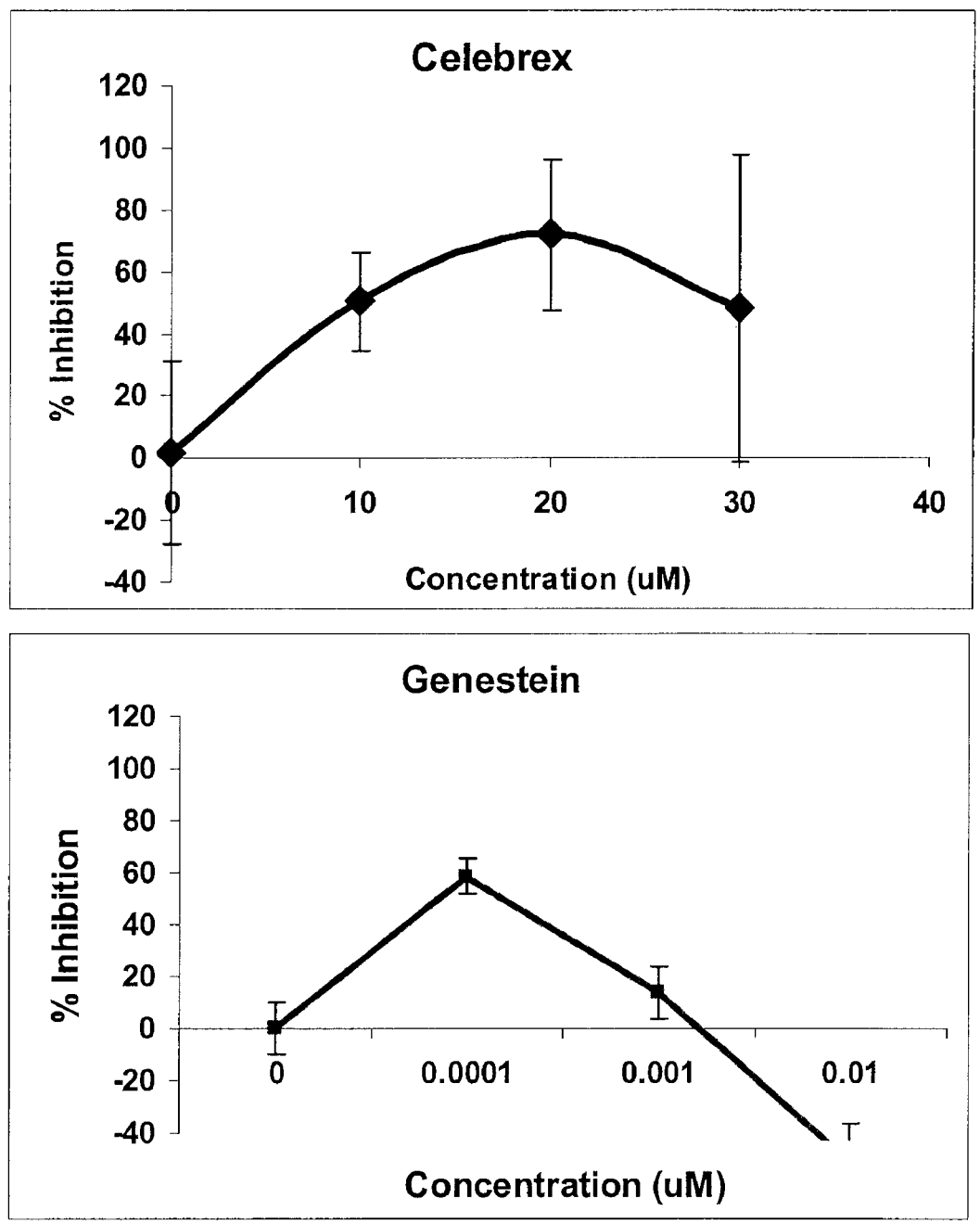
FIG. 6 shows the effects of anti-angiogenic drugs (co-treatment) on eye angiogenesis in $CoCl_2$ treated zebrafish. 1 dpf zebrafish were co-treated with 0.1 mg/ml $CoCl_2$ and various drug concentrations for 4 days. At 5 dpf stage, zebrafish were processed for the eye specific angiogenesis ELISA as described in Materials and Methods. Each point represents mean±SE (5≤n≤18). *indicated p<0.1, * *indicated p<0.05 by ANOVA.

Based on the visual assessment above, co-treatment chosen as the treatment method to investigate the effects of the anti-angiogenic drugs Celebrex and Genistein in $CoCl_2$ induced CNV in zebrafish using the eZ-CNV™ ELISA. Drug effects were calculated using the method described in Materials and Methods, infra. A typical dose response curve was observed for Celebrex (FIG. 6), whereas Genistein only showed preventative effects at a low concentration, which correlated with the results obtained by visual assessment (Table III and IV). Based on the dose response curve, the optimal concentration for Celebrex was 20 μM and for Genistein was 0.0001 μM.

D. Conclusions

Advantages of Eye Specific Angiogenesis ELISA. Taking advantage of the short assay time of this zebrafish CNV model, the eZ-CNV™ ELISA that we developed can be used to quantify the level of angiogenesis in compound treated CNV zebrafish. This assay can be used as a primary screen of a library of natural or synthetic products that contain anti-inflammatory and/or anti-oxidant compounds to identify potential AMD therapeutics. For large scale screening, knowledge of the potency of identified primary screen "hit" compounds will facilitate decision making involved in developing effective therapies. In this regard, a quantitative assay is more useful than a semi-quantitative image based assay.

E. Materials and Methods

Methods for Dissociating Eyes from Whole Zebrafish. Zebrafish were processed for whole mount immunochemical staining with either Alexa 488 or HRP conjugated Phy-V following standard procedures. After extensive washing, stained zebrafish were incubated with 150 U/ml collagenase at 37° C. for 45 minutes; eyes were then dissociated from the whole zebrafish by gentle pipetting.

Eye Specific Angiogenesis ELISA (eZ-CNV™ ELISA). Isolated eyes of whole mount Phy-V-HRP stained zebrafish were placed in 96-well microplates, 4 eyes/well; 150 µl/well PS-atto (Lumigen, Southfield, Mich.), chemiluminescence HRP substrate, was added and the chemiluminescence signal from the enzymatic product was detected by Synergy HT microplate reader (BioTeK Instruments, Inc., Winooski, Vt.).

Some of the embodiments of the invention can be expressed as follows. The invention provides a method of screening an agent for an ocular activity in an eye of a teleost, the method comprising: (a) contacting the teleost with the agent; (b) isolating an eye from the teleost; and (c) measuring a response to the agent in the isolated eye, wherein the response indicates that the agent has the ocular activity. Optionally, the ocular activity is a cell death and/or toxic activity. Optionally, step (b) comprises: contacting the teleost with an enzyme capable of dissociating the eye from the teleost; and collecting the separated eye. Optionally, the collecting step comprises filtration or density gradient centrifugation. Optionally, the enzyme is a collagenase, a dispase, a trypsin, a chymotrypsin, or a hyaluronidase. Optionally, the response to the agent is measured in the back of the isolated eye. Optionally, step (a) is performed while the teleost is contained in a first vessel and step (c) is performed while the isolated eye is contained in a second vessel. Optionally, the isolated eye is transferred to the second vessel following step (b). Optionally, a plurality of teleosts are contacted with the agent. Optionally, the plurality of teleosts are in wells of a multi-well plate. Optionally, at least some of the plurality of teleosts are contacted with a plurality of agents. Optionally, each of the least some of the plurality of teleosts is contacted with the plurality of agent simultaneously. Optionally, each of the at least some of the plurality of teleosts are contacted with the plurality of agents serially. Optionally, the agent or one of the agents is an inducer of ocular disease. Optionally, the agent or one of the agents is an inhibitor of ocular disease. Optionally, the agent or plurality of agents is administered before isolating the eye. Optionally, the response in the isolated eye is measured in the same well as that in which the eye is isolated. Optionally, the response is measured in a plurality of isolated eyes in the same well as that in which the eyes are isolated. Optionally, the plurality of eyes are from the same teleost. Optionally, the plurality of eyes are from different teleosts in the same well. Optionally, the method further comprises removing the teleost body from the well before the measuring step. Optionally, the method further comprises removing the teleost body from the well before the measuring step. Optionally, the method further comprises removing the teleost body from the well before the measuring step. Optionally, the isolated eye is transferred to a second well before measuring the response. Optionally, a plurality of eyes are isolated in a well and the plurality of eyes are transferred to a second well before measuring the response. Optionally, a plurality of teleosts are contained in the first vessel, wherein a plurality of eyes are isolated from the plurality of teleosts, and wherein at least some of the plurality of isolated eyes are transferred to the second vessel. Optionally, a plurality of teleosts are contained in a first vessel, step (a) being performed while the plurality of teleosts are contained in the first vessel, and wherein a plurality of eyes are isolated from the plurality of teleosts. Optionally, at least some of the plurality of isolated eyes are transferred to a plurality of second vessels. Optionally, the response is measured in each transferred isolated eye individually. Optionally, the teleost is contained in a well of a multi-well plate. Optionally, the contacting step comprises adding the agent to the well. Optionally, a plurality of teleosts are contacted with the agent. Optionally, the contacting step comprises adding the agent to at least one well of a plurality of wells in a multi-well plate. Optionally, the agent is added to at least some of the plurality of wells at a different concentration of the agent. Optionally, the agent is added to at least some of the plurality of wells at the same concentration of the agent. Optionally, at least some of the plurality of wells lack the agent. Optionally, the plurality of teleosts is contained within a plurality of wells of one or more multi-well plates. Optionally, at least some of the plurality of wells contains a single teleost from the plurality of teleosts. Optionally, at least some of the plurality of wells contains multiple teleosts from the plurality of teleosts. Optionally, the method further comprises contacting a plurality of teleosts with a plurality of agents such that at least some of the different teleosts are contacted with different agents. Optionally, the plurality of teleosts is contained within a plurality of wells of one or more multi-well plates. Optionally, the method further comprises transferring the isolated eyes from the plurality of wells to a second plurality of wells. Optionally, the second plurality of wells comprises corresponding wells to the wells in the plurality of wells, such that a well in the second plurality of wells receives the same eye(s) as were contained in a corresponding well in the first plurality of wells. Optionally, the response is detected using a microplate reader. Optionally, the reader is a high content imaging system. Optionally, the isolated eye is contained on a slide following isolation of the eye from the teleost. Optionally, a target biomolecule is detected, which can be a protein or mRNA. Optionally, the measuring step is performed on the isolated eye in situ, optionally by in situ mRNA hybridization. Optionally, the response is measured using a flow cytometer or a large particle dispenser. Optionally, the response is measured separately in each of a plurality of isolated eyes.

In some methods, the response to the agent comprises an increase or decrease in angiogenesis. The angiogenesis activity can be decreased or increased. In some methods, the response to the agent comprises an increase or decrease in blood vessel formation, which can be decreased or increased. Optionally, the blood vessels are visualized by staining of the eye with a vessel-specific antibody. Optionally, the blood vessels are visualized by light microscopy after enzymatic staining of the eye.

In some methods, the teleost is an embryo, larva, or adult. In some methods, the teleost is a zebrafish, medaka, Giant rerio, or puffer fish. In some methods, the teleost is a zebrafish embryo, larva or adult. Optionally, the teleost is a wild-type strain. Optionally, the teleost contains a mutation in a selected gene associated with an ocular disorder or disease. Optionally, the mutation is a vesicle glutamate transporter. Optionally, the mutation is a cloche mutation. Optionally, the mutation is a fade-out mutation. Optionally, the teleost is transgenic. Optionally, the transgene comprises a nucleic acid segment encoding a green fluorescent protein operably linked to an opsin promoter.

Optionally, the agent is administered to the teleost by dissolving the agent in media containing the teleost. Optionally, the agent is dissolved in the media before adding the teleost to the media. Optionally, the agent is administered to the teleost by injecting the agent into the teleost. Optionally, the agent is administered to the teleost by injecting the agent into the eye to be isolated. Optionally, the agent is administered to the teleost in conjunction with a carrier. Optionally, the carrier is a solvent, a lipid, or a peptide. Optionally, the agent is a small molecule. Optionally, the agent is a nucleic acid, nucleic acid analog, peptide, protein, glycoprotein, carbohydrate, lipid, or glycolipid. Optionally, the nucleic acid is DNA or RNA. Optionally, the nucleic acid is an siRNA or a morpholino. Optionally, a library of agents is screened for the activity in the isolated eye. Optionally, the library of agents is a library of small molecules. Optionally, the library of agents is a nucleic acid library or a peptide library. Optionally, measuring the response to the agent comprises assessing the isolated eye for a morphological change. Optionally, the morphological change comprises a change in size, shape, pigmentation, color, or structure of the eye. Optionally, the morphological change comprises a change in blood vessel structure. Optionally, assessing the morphological change comprises acquiring an image of the isolated eye. Optionally, the acquired image is a digital image and assessment of the morphological change comprises computer-based analysis of the digital image. Optionally, the method further comprises (d) contacting the teleost with an agent that induces a disease or disorder in the teleost, wherein the ocular activity is a therapeutic or prophylactic activity against the disorder or an activity that aggravates the disorder. Optionally, the measured response is indicative of a therapeutic or protective effect against the disease or disorder. In methods in which two agents are administered (e.g., an inducer of disease and a potential inhibitor of disease) the agents can be administered together or in either order.

Optionally, the activity in the eye of the teleost is ocular neovascularization and the method further comprises contacting the teleost with an agent that induces ocular neovascularization in the teleost. The cutting step and administering step can be performed in either order or together. Optionally, the compound that induces ocular neovascularization in the teleost is $CoCl_2$. Optionally, the compound that induces ocular neovascularization in the teleost is Penicillamine. Optionally, the teleost is contacted with the compound at 24 hours post-fertilization (hpf). Optionally, the activity in the eye of the teleost is ocular scarring, and the method further comprises surgically cutting the conjunctiva and then burning the sclera of the teleost. The cutting and administering steps can be performed in either order. Optionally, the method screens an agent for an ocular activity and a cell death and/or toxic activity in an eye of a teleost, the method further comprising: measuring a second response to the agent in the isolated eye, wherein the second response indicates that the agent has the cell death and/or toxic activity. Optionally, the presence of the second response indicates that the agent has the cell death activity or toxic activity.

Optionally, the method is a method of screening an agent for an ocular activity in an eye of a teleost and for cell death and/or toxic activity in at least one other organ or tissue of the teleost, the method further comprises measuring a second response to the agent in at least one other organ or tissue of the teleost, wherein the second response indicates that the agent has the cell death and/or toxic activity. Optionally, the presence of the second response indicates that the agent has the cell death activity. Optionally, the presence of the second response indicates that the agent has the toxic activity. Optionally, the measure of cell death and/or toxic activity is detected before isolating the eye.

Optionally, the method determines whether the agent induces a disease or disorder in the teleost and wherein the ocular activity is indicative of a disease or disorder. Optionally, a plurality of agents are screened for the ocular activity indicative of the disease or disorder.

The invention further provides a method of screening an agent for a prophylactic or therapeutic activity against a disease or disorder in an eye of a teleost, the method comprising: (a) contacting the teleost with a first agent that induces the disease or disorder in the teleost; (b) contacting the teleost with a second agent; (c) isolating an eye from the teleost; and (d) measuring a response to the agent in the isolated eye, wherein the response is indicative of whether the second agent has a prophylactic or therapeutic effect against the disease or disorder. Steps (a) and (b) can be performed in either order or together. Optionally, a plurality of agents are screened for the protective or therapeutic effect against the disease or disorder.

The invention further provides a method of isolating an eye of a teleost, comprising: (a) contacting the teleost with an enzyme that is capable of dissociating the eye from the teleost, wherein the eye is separated from the teleost; and (b) collecting the separated eye. Optionally, the enzyme is selected from the group consisting of a collagenase, a dispase, a trypsin, a chymotrypsin, and a hyaluronidase. Optionally, step (b) comprises filtration. Optionally, the enzyme is a collagenase. Optionally, the collagenase is selected from the group consisting of a bacterial collagenase and a mammalian collagenase. Optionally, the bacterial collagenase is selected from the group consisting of collagenase Type I, collagenase Type II, collagenase Type III and collagenase Type IV. Optionally, the bacterial collagenase is collagenase Type II.

Although the foregoing invention has been described in some detail for purposes of clarity and understanding, it will be clear from a reading of this disclosure that various changes in form and detail can be made without departing from the true scope of the invention. The above examples are provided to illustrate the invention, but not to limit its scope; other variants of the invention will be readily apparent and are encompassed by the claims of the invention. The scope of the invention should, therefore, be determined not with reference to the above description, but instead should be determined with reference to the appended claims along with their full scope of equivalents. Unless otherwise apparent from the context, any step, element, feature, embodiment or aspect of the invention can be used in combination with any other. All publications, references, and patent documents cited in this application are incorporated herein by reference in their entirety for all purposes to the same extent as if each individual publication or patent document were so individually denoted.

What is claimed is:

1. A method of screening an agent for a protective or therapeutic activity for an ocular disease, the method comprising: contacting a teleost with a first agent that is an inducer of ocular disease, and a second agent that is a protective or therapeutic agent for the disease; contacting the teleost with an enzyme that dissociates the eye from the teleost, wherein the enzyme is a collagenase, a dispase, a trypsin, a chymotrypsin, or a hyaluronidase; isolating the eye of the teleost; and analyzing a response to the second agent in the dissociated eye, wherein the presence of the response is indicative of the protective or therapeutic activity of the agent.

2. The method of claim 1, further comprising collecting the dissociated eye by filtration or density gradient centrifugation.

3. The method of claim 1, wherein the teleost is in a well of a multi-well plate.

4. The method of claim 1, wherein the first and second agents can be administered in either order or together.

5. The method of claim 1, wherein the response is analyzed using a microplate reader, a high content imaging system, or a microscope.

6. The method of claim 1, wherein the isolated eye is contained on a slide following isolation of the eye from the teleost.

7. The method of claim 1, wherein the analyzing step comprises detecting a target biomolecule.

8. The method of claim 7, wherein the target biomolecule is a protein or mRNA.

9. The method of claim 1, wherein the analyzing step is performed on the isolated eye in situ.

10. The method of claim 1, wherein the response to the agent comprises an increase or decrease in angiogenesis.

11. The method of claim 10, wherein the response to the agent comprises an increase or decrease in blood vessel formation.

12. The method of claim 10, wherein the blood vessels are visualized by staining of the eye with a vessel-specific antibody.

13. The method of claim 1, wherein the teleost is an embryo, larva, or adult.

14. The method of claim 1, wherein the teleost is a zebrafish, medaka, Giant rerio, or puffer fish.

15. The method of claim 1, wherein the teleost is a wildtype teleost.

16. The method of claim 1, wherein the teleost is a mutant or transgenic teleost.

17. The method of claim 1, wherein the first or the second agent, or both, is administered to the teleost by dissolving the agent in media used for culturing the teleost.

18. The method of claim 1, wherein the first or the second agent, or both, is administered to the teleost by injecting the agent into the teleost.

19. The method of claim 1, wherein the agent is a small molecule, nucleic acid, nucleic acid analog, peptide, protein, glycoprotein, carbohydrate, lipid, or glycolipid.

20. The method of claim 1, wherein the second agent is a member of a library of agents is screened for protective or therapeutic activity in the isolated eyes of a plurality of teleosts.

21. The method of claim 1, wherein analyzing the response to the agent comprises assessing the isolated eye for a morphological change.

22. The method of claim 21, wherein the morphological change comprises of a change in size, shape, pigmentation, color, or structure of the eye.

23. The method of claim 21, wherein the morphological change comprises a change in blood vessel structure.

24. The method of 21, wherein the assessing the morphological change comprises acquiring an image of the isolated eye.

25. The method of claim 24, wherein the acquired image is a digital image and assessment of the morphological change comprises computer-based analysis of the digital image.

26. A method of screening an agent for a protective or therapeutic activity for ocular scarring, the method comprising: surgically cutting conjunctiva and then burning the sclera of a teleost to include ocular scarring; contacting the teleost with an agent that is a potential protective or therapeutic agent; contacting the teleost with an enzyme that dissociates the eye from the teleost, wherein the enzyme is a collagenase, a dispase, a trypsin, a chymotrypsin, or a hyaluronidase; isolating the eye of the teleost; and analyzing a response to the agent in the dissociated eye, wherein the presence of reduced scarring of the sclera in the presence of the agent, relative to a control teleost not treated with the agent, is indicative of the protective or therapeutic activity of the agent.

27. The method of claim 26, wherein the cutting of the conjunctiva and the contacting with the agent are performed in either order, or together.

* * * * *